United States Patent
Li et al.

(10) Patent No.: US 12,195,527 B2
(45) Date of Patent: *Jan. 14, 2025

(54) ANTI-PD-1/VEGFA BIFUNCTIONAL ANTIBODY, PHARMACEUTICAL COMPOSITION THEREOF

(71) Applicant: AKESO BIOPHARMA, INC., Guangdong (CN)

(72) Inventors: Baiyong Li, Zhongshan (CN); Yu Xia, Zhongshan (CN); Zhongmin Maxwell Wang, Zhongshan (CN); Peng Zhang, Zhongshan (CN)

(73) Assignee: AKESO BIOPHARMA, INC., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,999

(22) Filed: May 12, 2023

(65) Prior Publication Data

US 2023/0340097 A1    Oct. 26, 2023

Related U.S. Application Data

(63) Continuation of application No. 17/272,121, filed as application No. PCT/CN2019/103618 on Aug. 30, 2019.

(30) Foreign Application Priority Data

Aug. 30, 2018    (CN) .......................... 201811002548.4

(51) Int. Cl.
C07K 16/22    (2006.01)
A61K 47/68    (2017.01)
(Continued)

(52) U.S. Cl.
CPC .......... *C07K 16/22* (2013.01); *A61K 47/6849* (2017.08); *A61P 35/00* (2018.01); *C07K 16/2818* (2013.01); *A61K 2039/505* (2013.01)

(58) Field of Classification Search
None
See application file for complete search history.

(56) References Cited

U.S. PATENT DOCUMENTS 6,884,879 B1    4/2005 Baca et al.
7,060,269 B1    6/2006 Baca et al.
(Continued)

FOREIGN PATENT DOCUMENTS

CN    105175544 A    12/2015
CN    105175545 A    12/2015
(Continued)

OTHER PUBLICATIONS

Uniprot, Acession P01857, IGHG1—Immunoglobulin heavy constant gamma 1—*Homo sapiens* (Human), Retrieved online :<URL: https://www.uniprot.org/uniprotkb/P01857/entry#structure>. [retrieved on Aug. 23, 2023], 2023.*

(Continued)

*Primary Examiner* — Claire Kaufman
(74) *Attorney, Agent, or Firm* — Seed IP Law Group LLP

(57) ABSTRACT

The present application relates to the fields of tumor treatment and molecular immunology, and specifically, to an anti-VEGFA/PD-1 bifunctional antibody, a pharmaceutical composition thereof and use thereof. Specifically, the anti-VEGFA/PD-1 bifunctional antibody comprises an antibody or antigen binding fragment thereof targeting VEGFA and an antibody or antigen binding fragment thereof targeting PD-1. The bifunctional antibody can specifically bind to (Continued)

VEGFA and PD-1, specifically relieve immunosuppression of VEGFA and PD-1 in an organism, and inhibit tumor-induced angiogenesis.

24 Claims, 17 Drawing Sheets

Specification includes a Sequence Listing.

(51) Int. Cl.
    *A61P 35/00*     (2006.01)
    *C07K 16/28*     (2006.01)
    *A61K 39/00*     (2006.01)

(56) References Cited

U.S. PATENT DOCUMENTS

| | | | |
|---|---|---|---|
| 7,297,334 | B2 | 11/2007 | Baca et al. |
| 9,079,953 | B2 | 7/2015 | Harding et al. |
| 9,815,893 | B2 | 11/2017 | Akamatsu |
| 11,459,405 | B2 * | 10/2022 | Sasisekharan et al. ........... C07K 16/468 |
| 11,578,128 | B2 | 2/2023 | Li et al. |
| 2012/0114649 | A1 | 5/2012 | Langermann et al. |
| 2015/0376271 | A1 | 12/2015 | Perlroth et al. |
| 2017/0275353 | A1 | 9/2017 | Sheng et al. |
| 2017/0275375 | A1 | 9/2017 | Rossi et al. |
| 2018/0305464 | A1 | 10/2018 | Li et al. |
| 2019/0016817 | A1 | 1/2019 | Taddei et al. |
| 2019/0185569 | A1 | 6/2019 | Li et al. |
| 2019/0321466 | A1 | 10/2019 | Li et al. |
| 2019/0367617 | A1 | 12/2019 | Li et al. |
| 2020/0289493 | A1 | 9/2020 | Bobilev et al. |
| 2020/0299389 | A1 | 9/2020 | Her et al. |
| 2021/0040193 | A1 | 2/2021 | Yang et al. |
| 2021/0340239 | A1 | 11/2021 | Li et al. |
| 2021/0403563 | A1 | 12/2021 | Wang et al. |
| 2021/0403575 | A1 | 12/2021 | Wang et al. |
| 2022/0267444 | A1 | 8/2022 | Wang et al. |
| 2022/0275089 | A1 | 9/2022 | Xia et al. |
| 2023/0027029 | A1 | 1/2023 | Zhang et al. |
| 2023/0235057 | A1 | 7/2023 | Zhao et al. |

FOREIGN PATENT DOCUMENTS

| | | | |
|---|---|---|---|
| CN | 106519034 A | | 3/2017 |
| CN | 106967172 A | | 7/2017 |
| CN | 106977602 A | | 7/2017 |
| CN | 20160705624 A | * | 7/2017 |
| CN | 108752476 A | | 11/2018 |
| CN | 109053895 A | | 12/2018 |
| CN | 110498857 A | | 11/2019 |
| CN | 110563849 A | | 12/2019 |
| CN | 110831580 A | | 2/2020 |
| CN | 110960543 A | | 4/2020 |
| CN | 112300286 A | | 2/2021 |
| CN | 112830972 A | | 5/2021 |
| EP | 3450460 A1 | | 3/2019 |
| EP | 3505535 A1 | | 7/2019 |
| EP | 4067387 A1 | | 10/2022 |
| EP | 4190816 A1 | * | 6/2023 ....... A61K 39/39533 |
| WO | WO 2004099249 A2 | | 11/2004 |
| WO | 2018/036472 A1 | | 3/2008 |
| WO | WO 2009058812 A1 | | 5/2009 |
| WO | 2011/109789 A2 | | 9/2011 |
| WO | WO 2012023053 A2 | | 2/2012 |
| WO | 2013/142255 A2 | | 9/2013 |
| WO | 2013/181452 A1 | | 12/2013 |
| WO | WO 2015200905 A2 | | 12/2015 |
| WO | 2017/165681 A1 | | 9/2017 |
| WO | 2017/181111 A2 | | 10/2017 |
| WO | 2017/185662 A1 | | 11/2017 |
| WO | 2018/133837 A1 | | 7/2018 |
| WO | WO 2018223923 A1 | | 12/2018 |
| WO | WO 2019152642 A1 | | 8/2019 |
| WO | WO 2019154349 A1 | | 8/2019 |
| WO | 2020/177627 A1 | | 9/2020 |
| WO | 2021/003739 A1 | | 1/2021 |
| WO | 2021/007428 A2 | | 1/2021 |
| WO | WO 2021026685 A1 | | 2/2021 |
| WO | 2021/069670 A1 | | 4/2021 |
| WO | WO 2021104302 A1 | | 6/2021 |
| WO | 2022/005100 A1 | | 1/2022 |
| WO | 2022/143801 A1 | | 7/2022 |

OTHER PUBLICATIONS

Uniprot, Acession P01834, IGKC—Immunoglobulin kappa constant—*Homo sapiens* (Human), Retrieved online :<URL:https://www.uniprot.org/uniprotkb/P01834/entry>. [retrieved on Aug. 24, 2023], 2023.*
Zhong et al., Mechanism of Action of Ivonescimab (AK112/SMT112): a First-In-Class Tetravalent FC-Silent Bispecific Antibody With Dual Blockade of PD-1 and VEGF That Promotes Cooperative Biological, Abstract 1194, J. Immunother. Canc. 11(Suppl. 1):A1316-1317, 2023.*
International Search Report, mailed Nov. 27, 2019, for International Application No. PCT/CN2019/103618, 14 pages.
Office Action, Japanese Application No. 2021-510912, mailed Jan. 24, 2023 (12 pages).
Sun et al., "A novel bispecific c-MET/PD-1 antibody with therapeutic potential in solid cancer," *Oncotarget* 8(17):29067-29079, Mar. 14, 2017.
Alfthan et al., "Properties of a single-chain antibody containing different linker peptides," *Protein Engineering* 8(7):725-731, Jul. 1995. (7 pages).
Bird et al., "Single-Chain Antigen-Binding Proteins," *Science* 242(4877):423-426, Oct. 1988. (5 pages).
Chothia et al., "Canonical Structures for the Hpervariable Regions of Immunoglobulins," *Journal of Molecular Biology* 196:901-917, Aug. 1987. (18 pages).
Chothia et al., "Conformations of immunoglobulin hypervariable regions," *Nature* 342:877-883, Dec. 1989. (7 pages).
Choi et al., "Recombinant chimeric OKT3 scFv IgM antibodies mediate immune suppression while reducing T cell activation in vitro," *European Journal of Immunology* 31:94-106, Jan. 2001. (13 pages).
Clark, "Antibody humanization: a case of the 'Emperor's new clothes'?," *Immunology Today* 21(8):397-402, Aug. 2000. (6 pages).
Cui et al., "Research Progress of PD-1/PD-L1 Inhibitors Combined with Other Immune Checkpoint Inhibitors in the Treatment of Triple Negative Breast Cancer," *Tianjin Medical Journal* 48(12):1230-1235, Dec. 2020. (6 pages).
Extended European Search Report, mailed Jul. 8, 2022, for European Patent Application No. 19853809.2-1111. (10 pages).
Fitzgerald et al., "Rational engineering of antibody therapeutics targeting multipleoncogene pathways," *mAbs* 3(3):299-309, May/Jun. 2011. (12 pages).
Ghonim et al., "Low Doses of PARP Inhibitors As A novel Therapeutic Approach to Enhance The Anti-Cancer Immunotherapy of PD-1 Immune Checkpoint Blockade," *The FASEB Journal* 33(S1):680.15, Apr. 2019 (Abstract only).
Holliger et al., ""Diabodies": Small bivalent and bispecific antibody fragments," *PNAS* N 90:6444-6448, Jul. 1993. (5 pages).
Hu et al., "Computational Design of IgG-like Tetra-specific Antibody Targeting EGFRNEGF/PD-1/CTLA-4 Against NSCLC," *Journal of Thoracic Oncology* 13(12S):S1086, Dec. 2018.
Hu et al., "Minibody: A Novel Engineered Anti-Carcinoembryonic Antigen Antibody Fragment (Single-Chain Fv-CH3) Which Exhibits Rapid, High-Level Targeting of Xenografts," *Cancer Research* 56:3055-3061, Jul. 1996. (8 pages).
International Search Report and Written Opinion of the International Searching Authority for International Application No. PCT/CN2020/131447 mailed on Jun. 3, 2021.
International Search Report, mailed Apr. 28, 2022, for International Patent Application No. PCT/CN2022/080107. (5 pages).

(56) References Cited

OTHER PUBLICATIONS

Jones et al., "Replacing the complementarity-determining regions in a human antibody Z with those from a mouse," *Nature* 321:522-525, May 1986. (4 pages).
Miller et al., "Stability engineering of scFvs for the development of bispecific and multivalent antibodies," *Protein Engineering, Design & Selection* 23(7):549-557, May 2010. (9 pages).
Müller et al., "Bispecific Antibodies for Cancer Immunotherapy," *BioDrugs* 24(2):89-98, Apr. 2010. (12 pages).
Poljak, "Production and structure of diabodies," *Structure* 2(12):1121-1123, Dec. 1994. (3 pages).
Presta, "Antibody engineering," *Current Opinion in Structural Biology* 2:593-596, Aug. 1992. (4 pages).
Riechmann et al., "Reshaping human antibodies for therapy," *Nature* 332:323-327, Mar. 1988. (5 pages).
Roovers et al., "In vitro characterisation of a monovalent and bivalent form of a fully human anti Ep-CAM phage antibody," *Cancer Immunology, Immunotherapy* 50:51-59, Mar. 2001. (9 pages).
Schlothauer et al., "Novel human IgG1 and IgG4 Fc-engineered antibodies with completely abolished immune effector functions," *Protein Engineering, Design & Selection* 29(10):457-466, 2016.
Tsuji, "The Forefront of Antibody Drugs," CMC Publishing Co., Ltd., Jul. 20, 2007 (with English translation). (20 pages).
UniProt, "RecName: Full=Immunoglobulin kappa constant; AltName: Full=Ig kappa chain C region; AltName: Full=Ig kappa chain C region AG; AltName: Full=Ig kappa chain C region CUM; AltName: Full=Ig kappa chain C region EU; AltNAme: Full=Ig kappa chain C region OU; AltName . . . " sequence ID P01834.2, Jul. 21, 1986 (annotation updated Apr. 7, 2021) (6 pages).
UniProt, "RecName: Full=Immunoglobulin heavy constant gamma 4; AltName: Full=Ig gamma-4 chain C region," sequence ID P01861.1, Jul. 21, 1986 (annotation updated Apr. 7, 2021) (6 pages).
UniProt, "RecName: Full=Immunoglobulin heavy constant gamma 1; AltName: Full=Ig gamma-1 chain C region; AltName: Full-Ig gamma-1 chain C region EU; AltName: Full=Ig gamma-1 chain C region KOL; AltName: Full=Ig gamma-1 chain C region NIE," sequence ID P01857.1, Jul. 21, 1986 (annotation updated Apr. 7, 2021) (9 pages).
Ward et al., "Binding activities of a repertoire of single immunoglobulin variable domains secreted from *Escherichia coli*," *Nature* 341:544-546, Oct. 1989. (3 pages).

Hezareh et al., "Effector Function Activities of a Panel of Mutants of a Broadly Neutralizing Antibody against Human Immunodeficiency Virus Type 1," *Journal of Virology* 75(24):12161-12168, Dec. 2001. (8 pages).
Pang et al., "Cadonilimab, a tetravalent PD-1/CTLA-4 bispecific antibody with trans-binding and enhanced target binding avidity," *MABS* 15(1)(2180794), Jan.-Dec. 2023. (10 pages).
U.S. Appl. No. 18/024,478, filed Mar. 2, 2023.
U.S. Appl. No. 18/264,242, filed Aug. 3, 2023.
*Allergan USA, Inc.* v. *MSN Laboratories Private Ltd.*, No. 24-1061, U.S. Court of Appeals, Federal Circuit, Aug. 13, 2024. (35 pages).
Buchbinder et al., "CTLA-4 and PD-1 Pathways: Similarities, Differences, and Implications of Their Inhibition," *American Journal of Clinical Oncology* 39(1):98-106, Feb. 2016. (9 pages).
Chan et al., "PARP Inhibitors in Cancer Diagnosis and Therapy," *Clinical Cancer Research* 27(6):1585-1594, Mar. 15, 2021. (28 pages).
Coloma et al., "Design and production of novel tetravalent bispecific antibodies," *Nature Biotechnology* 15:159-163, Feb. 1997. (5 pages).
Eichten et al., "Resistance to Anti-VEGF Therapy Mediated by Autocrine IL6/STAT3 Signaling and Overcome by IL6 Blockade," *Cancer Research* 76(8):2327-2329, Apr. 15, 2016. (13 pages).
Extended European Search Report and Written Opinion, dated Jul. 12, 2024, for European Patent Application No. 22766354.9. (10 pages).
Fitzgerald et al., "Rational engineering of antibody therapeutics targeting multiple oncogene pathways," *mAbs* 3(3):299-309; May/Jun. 2011. (11 pages).
Lo et al., "Effector Attenuating Substitutions That Maintain Antibody Stability and Reduce Toxicity in Mice," Journal of Biological Chemistry Papers in Press Manuscript, Jan. 11, 2017. (20 pages).
Moreno et al., "Anti-PD-1 Therapy in Melanoma," *Seminars in Oncology* 42(3):466-473, Jun. 2015. (8 pages).
Vikas et al., "Therapeutic Potential of Combining PARP Inhibitor and Immunotherapy in Solid Tumors," *Frontiers in Oncology* 10:570, Apr. 28, 2020. (10 pages).
Vinayak et al., "Open-label Clinical Trial of Niraparib Combined With Pembrolizumab for Treatment of Advanced or Metastatic Triple-Negative Breast Cancer," *JAMA Oncology* 5(8):1132-1140, Jun. 13, 2019. (9 pages).

\* cited by examiner

ANTI-PD-1/VEGFA BIFUNCTIONAL ANTIBODY, PHARMACEUTICAL COMPOSITION THEREOF

REFERENCE TO AN ELECTRONIC SEQUENCE LISTING

The contents of the electronic sequence listing 880167_401C1_SeqListing_v2.xml; Size: 39,673 bytes; and Date of Creation: Feb. 15, 2024) is herein incorporated by reference in its entirety.

TECHNICAL FIELD

The present application relates to the fields of tumor treatment and immunobiology, particularly to an anti-PD-1/VEGFA bifunctional antibody, a pharmaceutical composition thereof and use thereof. Specifically, the present application relates to an anti-human PD-1/human VEGFA bifunctional antibody, a pharmaceutical composition thereof and use thereof.

BACKGROUND

Tumor, especially a malignant tumor, is a serious health-threatening disease in the world today, and it is the second leading cause of death among various diseases. In recent years, the incidence of the disease has been increasing remarkably. Malignant tumor is characterized by poor treatment response, high late metastasis rate and poor prognosis. Although conventional treatment methods (such as radiotherapy, chemotherapy and surgical treatment) adopted clinically at present alleviate the pain to a great extent and prolong the survival time, the methods have great limitations, and it is difficult to further improve their efficacy.

There are two distinct stages of tumor growth, namely, from a slow growth stage without blood vessels to a rapid proliferation stage with blood vessels. The angiogenesis enables the tumor to acquire enough nutrition to complete the blood vessel switching stage, and if there is no angiogenesis, the primary tumor will be no more than 1-2 mm, and thus the metastasis cannot be realized.

Vascular Endothelial Growth Factor (VEGF) is a growth factor which can promote division and proliferation of endothelial cells, promote formation of new blood vessels and improve blood vessel permeability, and it binds to vascular endothelial growth factor receptors on the cell surface and plays a role by activating tyrosine kinase signal transduction pathways. In tumor tissues, tumor cells, and macrophages and mast cells invading into tumors can secrete high-level VEGF, stimulate tumor vascular endothelial cells in a paracrine form, promote proliferation and migration of endothelial cells, induce angiogenesis, promote continuous growth of tumor, improve vascular permeability, cause fibrin deposition in surrounding tissues, and promote infiltration of mononuclear cells, fibroblast and endothelial cells, which facilitates formation of tumor stroma and entry of tumor cells into new blood vessels, and promote tumor metastasis. Therefore, inhibiting tumor angiogenesis is considered to be one of the most promising tumor treatment methods at present. The VEGF family includes: VEGFA, VEGFB, VEGFC, VEGFD and PIGF. Vascular Endothelial Growth Factor Receptors (VEGFRs) include VEGFR1 (also known as Flt1), VEGFR2 (also known as KDR or Flk1), VEGFR3 (also known as Flt4), and Neuropilin-1 (NRP-1). The first three receptors are similar in structure, belong to a tyrosine kinase superfamily, and are composed of an extramembrane region, a transmembrane segment and an intramembrane region, where the extramembrane region is composed of an immunoglobulin-like domain, and the intramembrane region is a tyrosine kinase region. VEGFR1 and VEGFR2 are located primarily on the surface of vascular endothelial cells, and VEGFR3 is located primarily on the surface of lymphatic endothelial cells.

Molecules of the VEGF family have different affinities for these receptors. VEGFA mainly acts in combination with VEGFR1, VEGFR2 and NRP-1. VEGFR1 is the earliest found receptor and has a higher affinity for VEGFA than VEGFR2 under normal physiological conditions, but it has a lower tyrosinase activity in intracellular segment than VEGFR2 (Ma Li, J. *Chinese Journal of Birth Health and Heredity*, 24 (5): 146-148 (2016)).

VEGFR2 is the primary regulator of angiogenesis and vascular engineering, and has a much higher tyrosine kinase activity than VEGFR1. VEGFR2, after binding to ligand VEGFA, mediates the proliferation, differentiation and the like of vascular endothelial cells, as well as the formation process of blood vessels and the permeability of blood vessels (Roskoski R Jr. et al., *Crit Rev Oncol Hematol*, 62 (3): 179-213 (2007)). VEGFA, after binding to VEGFR2, mediates the transcriptional expression of intracellular related protein genes through the downstream PLC-γ-PKC-Raf-MEK-MAPK signaling pathway, and thus promotes the proliferation of vascular endothelial cells (Takahashi T et al., *Oncogene*, 18 (13): 2221-2230 (1999)).

VEGFR3 is one of the tyrosine kinase family members, and mainly expresses embryonic vascular endothelial cell and adult lymphatic endothelial cells, and VEGFC and VEGFD bind to VEGFR3 to stimulate proliferation and migration of lymphatic endothelial cells and promote neogenesis of lymphatic vessels; NRP-1 is a non-tyrosine kinase transmembrane protein and is incapable of independently transducing biological signals, and it is able to mediate signaling only after forming a complex with a VEGF tyrosine kinase receptor. (Ma Li, *Chinese Journal of Birth Health and Heredity*, 24 (5): 146-148 (2016)).

VEGFA and VEGFR2 are mainly involved in regulation of angiogenesis, where before and after the binding of VEGFA to VEGFR2, a cascade reaction of numerous intermediate signals in upstream and downstream pathways is formed, and finally the physiological functions are changed by proliferation, survival, migration, permeability increase and infiltration to peripheral tissues, etc. of endothelial cells (Dong Hongchao et al., September 2014, *Journal of Modern Oncology*, 22 (9): 2231-3).

Currently, there are several humanized monoclonal antibodies targeting human VEGF, particularly VEGFA, such as bevacizumab, which has been approved by the U.S. Food and Drug Administration for the treatment of various tumors such as non-small cell lung cancer, renal cell carcinoma, cervical cancer, and metastatic colorectal cancer in succession during 2004.

The programmed cell death receptor-1 (PD-1), also known as CD279, is a type I transmembrane glycoprotein membrane surface receptor, belongs to the CD28 immunoglobulin superfamily, and is commonly expressed in T cells, B cells, and myeloid cells. PD-1 has two natural ligands, PD-L1 and PD-L2. Both PD-L1 and PD-L2 belong to the B7 superfamily and are expressed constitutively or inducibly on the membrane surface a variety of cells, including nonhematopoietic cells and a variety of tumor cells. PD-L1 is mainly expressed on T cells, B cells, DC and microvascular endothelial cells and a variety of tumor cells, while PD-L2 is expressed only on antigen presenting cells such as dendritic cells and macrophages. The interaction between PD-1 and its ligands can inhibit the activation of lymph, the proliferation of T cells, and the secretion of cytokines such as IL-2 and IFN-γ.

A large number of research shows that a tumor microenvironment can protect tumor cells from being damaged by immune cells, expression of PD-1 in lymphocytes infiltrated in the tumor microenvironment is up-regulated, and various primary tumor tissues are PD-L1 positive in immunohistochemical analysis, such as lung cancer, liver cancer, ovarian cancer, skin cancer, colon cancer and glioma. Meanwhile, the expression of PD-L1 in the tumor is significantly correlated with poor prognosis of cancer patients. Blocking the interaction between PD-1 and its ligands can promote the tumor-specific T cell immunity and enhance the immune elimination efficiency of tumor cells. A large number of clinical trials show that antibodies targeting PD-1 or PD-L1 can promote infiltration of $CD8^+$ T cells into tumor tissues and up-regulate anti-tumor immune effector factors such as IL-2, IFN-γ, granzyme B and perforin, thereby effectively inhibiting the growth of tumors.

In addition, anti-PD-1 antibodies may also be used in the treatment of viral chronic infections. Viral chronic infections are often accompanied by a loss of function of virus-specific effector T cells and a reduction in its number. The interaction between PD-1 and PD-L1 can be blocked by injecting a PD-1 antibody, thereby effectively inhibiting the exhaustion of effector T cells in viral chronic infection.

Due to the broad anti-tumor prospect and surprising efficacy of PD-1 antibodies, it is widely accepted in the industry that antibodies targeting the PD-1 pathway will bring about breakthroughs in the treatment of a variety of tumors: for the treatment of non-small cell lung cancer, renal cell carcinoma, ovarian cancer and melanoma (Homet M. B., Parisi G., et al., Anti-PD-1 therapy in melanoma. *Semin Oncol.* 2015 June; 42 (3): 466-473), and lymphoma and anemia (Held S A, Heine A, et al., Advances in immunotherapy of chronic myeloid leukemia CML. *Curr Cancer Drug Targets* 2013 September; 13 (7): 768-74).

The bifunctional antibody, also known as bispecific antibody, is a specific medicament that targets two different antigens simultaneously, and can be produced by immunoselection purification. In addition, the bispecific antibody can also be produced by genetic engineering, which has certain advantages due to corresponding flexibility in aspects such as the optimization of binding sites, consideration of synthetic form, and yield. Currently, the bispecific antibody has been demonstrated to exist in over 45 forms (Müller D, Kontermann R E. Bispecific antibodies for cancer immunotherapy: current perspectives. *BioDrugs* 2010; 24:89-98). A number of bispecific antibodies have been developed in the form of IgG-ScFv, namely the Morrison form (Coloma M. J., Morrison S. L. Design and production of novel tetravalent bispecific antibodies. *Nat Biotechnol.,* 1997; 15:159-163), which has been demonstrated to be one of the ideal forms of the bispecific antibodies because of its similarity to the naturally existing IgG form and advantages in antibody engineering, expression and purification (Miller B. R., Demarest S. J., et al., Stability engineering of scFvs for the development of bispecific and multivalent antibodies. *Protein Eng Des Sel* 2010; 23:549-57; Fitzgerald J, Lugovskoy A. Rational engineering of antibody therapeutics targeting multiple oncogene pathways. *MAbs* 2011; 3:299-309).

Currently, there is a need to develop a bifunctional antibody medicament targeting both PD-1 and VEGF (e.g., VEGFA).

SUMMARY

Through in-depth research and creative efforts, and based on commercially available VEGFA monoclonal antibody AVASTIN® (bevacizumab) and 14C12H1L1 acquired before (see Chinese patent publication No. CN106977602A), the inventors have acquired a humanized bifunctional antibody named VP101, which is capable of simultaneously binding to VEGFA and PD-1, and blocking the binding of VEGFA to VEGFR2 and that of PD-1 to PD-L1.

The inventors have surprisingly found that VP101 is capable of:

effectively binding to PD-1 on the surface of human immune cells, relieving immunosuppression mediated by PD-L1 and PD-1, and promoting secretion of IFN-γ and IL-2 by human immune cells;

effectively inhibiting VEGFA-induced proliferation of vascular endothelial cells, and thereby inhibiting tumor-induced angiogenesis; and/or having the potential of being used for preparing medicaments for preventing and treating malignant tumors such as liver cancer, lung cancer, melanoma, renal tumor, ovarian cancer and lymphoma.

The subject matter of the present application is detailed below.

One aspect of the present application relates to a bispecific antibody, which comprises:

a first protein functional region targeting VEGFA, and
a second protein functional region targeting PD-1;
preferably,
the first protein functional region is an anti-VEGFA antibody or an antigen-binding fragment thereof, a heavy chain variable region of the anti-VEGFA antibody comprising HCDR1-HCDR3 with amino acid sequences set forth in SEQ ID NOs: 15-17 respectively, and a light chain variable region of the anti-VEGFA antibody comprising LCDR1-LCDR3 with amino acid sequences set forth in SEQ ID NOs: 18-20 respectively; and the second protein functional region is an anti-PD-1 antibody or an antigen-binding fragment thereof, a heavy chain variable region of the anti-PD-1 antibody comprising HCDR1-HCDR3 with amino acid sequences set forth in SEQ ID NOs: 21-23 respectively, and a light chain variable region of the anti-PD-1 antibody comprising LCDR1-LCDR3 with amino acid sequences set forth in SEQ ID NOs: 24-26 respectively.

In some embodiments of the present application, the bispecific antibody is provided, wherein, the anti-VEGFA antibody or the antigen-binding fragment thereof is selected from Fab, Fab', F(ab')$_2$, Fd, Fv, dAb, a complementarity determining region fragment, a single chain antibody, a humanized antibody, a chimeric antibody, and a diabody;

and/or, the anti-PD-1 antibody or the antigen-binding fragment thereof is selected from Fab, Fab', F(ab')$_2$, Fd, Fv, dAb, a complementarity determining region fragment, a single chain antibody, a humanized antibody, a chimeric antibody, and a diabody.

In some embodiments of the present application, the bispecific antibody is in IgG-scFv form.

In some embodiments of the present application, the first protein functional region is an immunoglobulin, a heavy chain variable region of the immunoglobulin comprising HCDR1-HCDR3 with amino acid sequences set forth in SEQ ID NOs: 15-17 respectively, and a light chain variable region of the immunoglobulin comprising LCDR1-LCDR3 with amino acid sequences set forth in SEQ ID NOs: 18-20 respectively; and the second protein functional region is a single chain antibody, a heavy chain variable region of the single chain antibody comprising HCDR1-HCDR3 with amino acid sequences set forth in SEQ ID NOs: 21-23 respectively, and a light chain variable region of the single chain antibody comprising LCDR1-LCDR3 with amino acid sequences set forth in SEQ ID NOs: 24-26 respectively;

or, the first protein functional region is a single chain antibody, a heavy chain variable region of the single chain antibody comprising HCDR1-HCDR3 with amino acid sequences set forth in SEQ ID NOs: 21-23 respectively, and a light chain variable region of the single chain antibody comprising LCDR1-LCDR3 with amino acid sequences set forth in SEQ ID NOs: 24-26 respectively; and the second protein functional region is an immunoglobulin, a heavy chain variable region of the immunoglobulin comprising HCDR1-HCDR3 with amino acid sequences set forth in SEQ ID NOs: 15-17 respectively, and a light chain variable region of the immunoglobulin comprising LCDR1-LCDR3 with amino acid sequences set forth in SEQ ID NOs: 18-20 respectively.

In a specific embodiment of the present application, a bispecific antibody is provided, which comprises:

a first protein functional region targeting VEGFA, and
a second protein functional region targeting PD-1;
wherein,
the first protein functional region is an immunoglobulin, a heavy chain variable region of the immunoglobulin comprising HCDR1-HCDR3 with amino acid sequences set forth in SEQ ID NOs: 15-17 respectively, and a light chain variable region of the immunoglobulin comprising LCDR1-LCDR3 with amino acid sequences set forth in SEQ ID NOs: 18-20 respectively; and the second protein functional region is a single chain antibody, a heavy chain variable region of the single chain antibody comprising HCDR1-HCDR3 with amino acid sequences set forth in SEQ ID NOs: 21-23 respectively, and a light chain variable region of the single chain antibody comprising LCDR1-LCDR3 with amino acid sequences set forth in SEQ ID NOs: 24-26 respectively;

or, the first protein functional region is a single chain antibody, a heavy chain variable region of the single chain antibody comprising HCDR1-HCDR3 with amino acid sequences set forth in SEQ ID NOs: 21-23 respectively, and a light chain variable region of the single chain antibody comprising LCDR1-LCDR3 with amino acid sequences set forth in SEQ ID NOs: 24-26 respectively; and the second protein functional region is an immunoglobulin, a heavy chain variable region of the immunoglobulin comprising HCDR1-HCDR3 with amino acid sequences set forth in SEQ ID NOs: 15-17 respectively, and a light chain variable region of the immunoglobulin comprising LCDR1-LCDR3 with amino acid sequences set forth in SEQ ID NOs: 18-20 respectively.

In some embodiments of the present application, the bispecific antibody is provided, wherein, the amino acid sequence of the heavy chain variable region of the immunoglobulin is set forth in SEQ ID NO: 5, and the amino acid sequence of the light chain variable region of the immunoglobulin is set forth in SEQ ID NO: 7; and the amino acid sequence of the heavy chain variable region of the single chain antibody is set forth in SEQ ID NO: 9, and the amino acid sequence of the light chain variable region of the single chain antibody is set forth in SEQ ID NO: 11;

or, the amino acid sequence of the heavy chain variable region of the single chain antibody is set forth in SEQ ID NO: 9, and the amino acid sequence of the light chain variable region of the single chain antibody is set forth in SEQ ID NO: 11; and the amino acid sequence of the heavy chain variable region of the immunoglobulin is set forth in SEQ ID NO: 5, and the amino acid sequence of the light chain variable region of the immunoglobulin is set forth in SEQ ID NO: 7.

In some embodiments of the present application, the bispecific antibody is provided, wherein, the immunoglobulin comprises a non-CDR region derived from a species other than murine, such as from a human antibody.

In some embodiments of the present application, the bispecific antibody is provided, wherein,
the immunoglobulin comprises constant regions derived from a human antibody;
preferably, the constant regions of the immunoglobulin are selected from constant regions of human IgG1, IgG2, IgG3, and IgG4.

In some embodiments of the present application, the bispecific antibody is provided, wherein,
the heavy chain constant region of the immunoglobulin is human Ig gamma-1 chain C region or human Ig gamma-4 chain C region, and its light chain constant region is human Ig kappa chain C region.

In some embodiments of the present application, the constant regions of the immunoglobulin are humanized. For example, each heavy chain constant region is Ig gamma-1 chain C region, Uniprot ACCESSION: P01857, and each light chain constant region is Ig kappa chain C region, Uniprot ACCESSION: P01834.

In some embodiments of the present application, the bispecific antibody is provided, wherein the first protein functional region and the second protein functional region are linked directly or via a linker fragment;
preferably, the linker fragment is [(GGGGS) SEQ ID NO:14]m, wherein m is a positive integer such as 1, 2, 3, 4, 5, or 6, and GGGGS (SEQ ID NO: 14) is a constituent unit of the linker.

In some embodiments of the present application, the bispecific antibody is provided, wherein the numbers of the first protein functional region and the second protein functional region are each independently 1, 2 or more.

In some embodiments of the present application, the bispecific antibody is provided, wherein 1 immunoglobulin and 2 single chain antibodies, preferably two identical single chain antibodies, are present.

In some embodiments of the present application, the bispecific antibody is provided, wherein the immunoglobulin is an IgG, IgA, IgD, IgE, or IgM, preferably an IgG, such as an IgG1, IgG2, IgG3 or IgG4.

In some embodiments of the present application, the bispecific antibody is provided, wherein the single chain antibody is linked to the C-terminus of the heavy chain of the immunoglobulin. Since an immunoglobulin has two heavy chains, two single chain antibody molecules are linked to one immunoglobulin molecule. Preferably, the two single chain antibody molecules are identical.

In some embodiments of the present application, the bispecific antibody is provided, wherein two single chain antibodies are present, and one terminus of each single chain antibody is linked to the C-terminus or the N-terminus of one of the two heavy chains of the immunoglobulin.

In some embodiments of the present application, a disulfide bond is present between the $V_H$ and the $V_L$ of the single chain antibody. Methods for introducing a disulfide bond between the VH and VL of an antibody are well known in the art, see, for example, U.S. Pat. No. 5,747,654; Rajagopal et al., *Prot. Engin.* 10 (1997) 1453-1459; Reiter et al., *Nat. Biotechnol.* 14 (1996) 1239-1245; Reiter et al., *Protein Engineering* 8 (1995) 1323-1331; Webber et al., *Molecular Immunology* 32 (1995) 249-258; Reiter et al., *Immunity* 2 (1995) 281-287; Reiter et al., *JBC* 269 (1994) 18327-18331; Reiter et al., *Inter. J. of Cancer* 58 (1994) 142-149; or Reiter et al., *Cancer Res.* 54 (1994) 2714-2718, which are incorporated herein by reference.

In some embodiments of the present application, the bispecific antibody is provided, wherein the bispecific antibody binds to a VEGFA protein and/or a PD-1 protein with a $K_D$ of less than $10^{-5}$ M, such as less than $10^{-6}$ M, $10^{-7}$ M, $10^{-8}$ M, $10^{-9}$ M or $10^{-10}$ M or less; preferably, the $K_D$ is measured by a Fortebio molecular interaction instrument.

In some embodiments of the present application, the bispecific antibody is provided, wherein,
the bispecific antibody binds to the VEGFA protein with an $EC_{50}$ of less than 1 nM, less than 0.5 nM, less than 0.2 nM, less than 0.15 nM, or less than 0.14 nM; preferably, the $EC_{50}$ is detected by indirect ELISA; and/or,
the bispecific antibody binds to the PD-1 protein with an $EC_{50}$ of less than 1 nM, less than 0.5 nM, less than 0.2 nM, less than 0.17 nM, less than 0.16 nM, or less than 0.15 nM; preferably, the $EC_{50}$ is detected by indirect ELISA.

Another aspect of the present application relates to an isolated nucleic acid molecule encoding the bispecific antibody according to any embodiment of the present application.

The present application also relates to a vector comprising the isolated nucleic acid molecule of the present application.

The present application also relates to a host cell comprising the isolated nucleic acid molecule of the present application or comprising the vector of the present application.

Another aspect of the present application relates to a method for preparing the bispecific antibody according to any embodiment of the present application, which comprises culturing the host cell of the present application in a suitable condition and isolating the bispecific antibody from the cell cultures.

Another aspect of the present application relates to a conjugate, comprising a bispecific antibody and a conjugated moiety, wherein the bispecific antibody is the bispecific antibody according to any embodiment of the present application, and the conjugated moiety is a detectable label; preferably, the conjugated moiety is a radioisotope, a fluorescent substance, a luminescent substance, a colored substance, or an enzyme.

Another aspect of the present application relates to a kit comprising the bispecific antibody according to any embodiment of the present application or comprising the conjugate of the present application;
preferably, the kit further comprises a second antibody capable of specifically binding to the bispecific antibody; optionally, the second antibody further comprises a detectable label, such as a radioisotope, a fluorescent substance, a luminescent substance, a colored substance, or an enzyme.

Another aspect of the present application relates to use of the bispecific antibody according to any embodiment of the present application in preparing a kit for detecting the presence or level of VEGFA and/or PD-1 in a sample.

Another aspect of the present application relates to a pharmaceutical composition comprising the bispecific antibody according to any embodiment of the present application or comprising the conjugate of the present application; optionally, it further comprises a pharmaceutically acceptable excipient.

The bispecific antibody of the present application or the pharmaceutical composition of the present application may be formulated into any dosage form known in the pharmaceutical field, such as tablet, pill, suspension, emulsion, solution, gel, capsule, powder, granule, elixir, troche, suppository, injection (including injection solution, sterile powder for injection and concentrated solution for injection), inhalant, and spray. The preferred dosage form depends on the intended mode of administration and therapeutic use. The pharmaceutical composition of the present application should be sterile and stable under the conditions of manufacture and storage. One preferred dosage form is an injection. Such injections may be sterile injection solutions. For example, sterile injection solutions can be prepared by the following method: a necessary amount of the bispecific antibody of the present application is added in an appropriate solvent, and optionally, other desired ingredients (including, but not limited to, pH regulators, surfactants, adjuvants, ionic strength enhancers, isotonic agents, preservatives, diluents, or any combination thereof) are added at the same time, followed by filtration and sterilization. In addition, sterile injection solutions can be prepared as sterile lyophilized powders (e.g., by vacuum drying or lyophilizing) for convenient storage and use. Such sterile lyophilized powders may be dispersed in a suitable carrier (e.g., sterile pyrogen-free water) prior to use.

In addition, the bispecific antibody of the present application may be present in a pharmaceutical composition in unit dose form for ease of administration. In some embodiments, the unit dose is at least 1 mg, at least 5 mg, at least 10 mg, at least 15 mg, at least 20 mg, at least 25 mg, at least 30 mg, at least 45 mg, at least 50 mg, at least 75 mg, or at least 100 mg. Where the pharmaceutical composition is in a liquid (e.g., injection) dosage form, it may comprise the bispecific antibody of the present application at a concentration of at least 0.1 mg/mL, such as at least 0.25 mg/mL, at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL, or at least 100 mg/mL.

The bispecific antibody or the pharmaceutical composition of the present application may be administered by any suitable method known in the art, including, but not limited to, oral, buccal, sublingual, ocular, topical, parenteral, rectal, intrathecal, intracisternal, inguinal, intravesical, topical (e.g., powder, ointment, or drop), or nasal route. However, for many therapeutic uses, the preferred route/mode of administration is parenteral (such as intravenous injection, subcutaneous injection, intraperitoneal injection, and intramuscular injection). Those skilled in the art will appreciate that the route and/or mode of administration will vary depending on the intended purpose. In a preferred embodiment, the bispecific antibody or the pharmaceutical composition of the present application is administered by intravenous infusion or injection.

The bispecific antibody or the pharmaceutical composition provided herein can be used alone or in combination, or used in combination with additional pharmaceutically active agents (e.g., a tumor chemotherapeutic drug). Such an additional pharmaceutically active agent may be administered prior to, concurrently with, or subsequent to the administration of the bispecific antibody of the present application or the pharmaceutical composition of the present application.

In the present application, the administration regimen may be adjusted to achieve the optimal desired response (e.g., a therapeutic or prophylactic response). For example, it may be a single administration, may be multiple administrations over a period of time, or may be characterized by reducing or increasing the dose proportionally with the emergency degree of the treatment.

Another aspect of the present application relates to use of the bispecific antibody according to any embodiment of the present application or the conjugate of the present application in preparing a medicament for preventing and/or treating a malignant tumor, wherein preferably, the malignant tumor is selected from colon cancer, rectal cancer, lung cancer such as non-small cell lung cancer, liver cancer, ovarian cancer, skin cancer, glioma, melanoma, renal tumor, prostate cancer, bladder cancer, gastrointestinal cancer, breast cancer, brain cancer and leukemia.

Another aspect of the present application relates to use of the bispecific antibody according to any embodiment of the present application or the conjugate of the present application in preparing:

(1)
   a medicament or an agent for detecting the level of VEGFA in a sample,
   a medicament or an agent for blocking binding of VEGFA to VEGFR2,
   a medicament or an agent for down-regulating the activity or level of VEGFA,
   a medicament or an agent for relieving the stimulation of VEGFA on vascular endothelial cell proliferation,
   a medicament or an agent for inhibiting vascular endothelial cell proliferation, or
   a medicament or an agent for blocking tumor angiogenesis;
   and/or
(2)
   a medicament or an agent for blocking the binding of PD-1 to PD-L1,
   a medicament or an agent for down-regulating the activity or level of PD-1,
   a medicament or an agent for relieving the immunosuppression of PD-1 in an organism,
   a medicament or an agent for promoting IFN-γ secretion in T lymphocytes, or
   a medicament or an agent for promoting IL-2 secretion in T lymphocytes.

In one embodiment of the present application, the use is non-therapeutic and/or non-diagnostic.

Another aspect of the present application relates to an in vivo or in vitro method comprising administering to a cell an effective amount of the bispecific antibody according to any embodiment of the present application or the conjugate of the present application, and the method is selected from:

(1)
   a method for detecting the level of VEGFA in a sample,
   a method for blocking the binding of VEGFA to VEGFR2,
   a method for down-regulating the activity or level of VEGFA,
   a method for relieving the stimulation of VEGFA on vascular endothelial cell proliferation,
   a method for inhibiting vascular endothelial cell proliferation, or
   a method for blocking tumor angiogenesis;
   and/or
(2)
   a method for blocking the binding of PD-1 to PD-L1,
   a method for down-regulating the activity or level of PD-1,
   a method for relieving the immunosuppression of PD-1 in an organism,
   a method for promoting IFN-γ secretion in T lymphocytes, or
   a method for promoting IL-2 secretion in T lymphocytes.

In one embodiment of the present application, the in vitro method is non-therapeutic and/or non-diagnostic.

In the in vitro experiment of the present application, the anti-VEGFA antibody and the anti-VEGFA/PD-1 bifunctional antibody both can inhibit HUVEC cell proliferation, and the anti-PD-1 antibody and the anti-VEGFA/PD-1 bifunctional antibody both can promote the secretion of IFN-γ and/or IL-2 and activate immune reaction.

Another aspect of the present application relates to a method for preventing and/or treating a malignant tumor, comprising administering to a subject in need an effective amount of the bispecific antibody according to any embodiment of the present application or the conjugate of the present application, wherein preferably, the malignant tumor is selected from colon cancer, rectal cancer, lung cancer such as non-small cell lung cancer, liver cancer, ovarian cancer, skin cancer, glioma, melanoma, renal tumor, prostate cancer, bladder cancer, gastrointestinal cancer, breast cancer, brain cancer and leukemia.

A typical non-limiting range of a therapeutically or prophylactically effective amount of the bispecific antibody of the present application is 0.02-50 mg/kg, such as 0.1-50 mg/kg, 0.1-25 mg/kg, or 1-10 mg/kg. It should be noted that the dose may vary with the type and severity of the symptom to be treated. Furthermore, those skilled in the art will appreciate that for any particular patient, the particular administration regimen will be adjusted over time according to the needs of the patient and the professional judgment of the physician; the dose ranges given herein are for illustrative purpose only and do not limit the use or scope of the pharmaceutical composition of the present application.

In the present application, the subject may be a mammal, such as a human.

Provided is the bispecific antibody or the conjugate according to any embodiment of the present application for use in preventing and/or treating a malignant tumor, wherein preferably, the malignant tumor is selected from colon cancer, rectal cancer, lung cancer such as non-small cell lung cancer, liver cancer, ovarian cancer, skin cancer, glioma, melanoma, renal tumor, prostate cancer, bladder cancer, gastrointestinal cancer, breast cancer, brain cancer and leukemia.

Provided is the bispecific antibody or conjugate according to any embodiment of the present application for use in:

(1)
- detecting the level of VEGFA in a sample,
- blocking the binding of VEGFA to VEGFR2,
- down-regulating the activity or level of VEGFA,
- relieving the stimulation of VEGFA on vascular endothelial cell proliferation,
- inhibiting vascular endothelial cell proliferation, or
- blocking tumor angiogenesis;

and/or (2)
- blocking the binding of PD-1 to PD-L1,
- down-regulating the activity or level of PD-1,
- relieving the immunosuppression of PD-1 in an organism,
- promoting IFN-γ secretion in T lymphocytes, or
- promoting IL-2 secretion in T lymphocytes.

Antibody drugs, especially monoclonal antibodies, have achieved good efficacy in the treatment of various diseases. Traditional experimental methods for acquiring these therapeutic antibodies are to immunize animals with the antigen and acquire antibodies targeting the antigen in the immunized animals, or to improve those antibodies with lower affinity for the antigen by affinity maturation.

The variable regions of the light chain and the heavy chain determine the binding of the antigen; the variable region of each chain contains three hypervariable regions called Complementarity Determining Regions (CDRs) (CDRs of the heavy chain (H Chain) comprise HCDR1, HCDR2, and HCDR3, and CDRs of the light chain (L Chain) comprise LCDR1, LCDR2, and LCDR3, which are named by Kabat et al., see Bethesda M.d., Sequences of Proteins of Immunological Interest, Fifth Edition, NIH Publication (1-3) 1991:91-3242).

Preferably, CDRs may also be defined by the IMGT numbering system, see Ehrenmann, Francois, Quentin Kaas, and Marie-Paule Lefranc. "IMGT/3Dstructure-DB and IMGT/DomainGapAlign: a database and a tool for immunoglobulins or antibodies, T cell receptors, MHC, IgSF and MhcSF." *Nucleic acids research* 38.suppl_1 (2009): D301-D307.

The amino acid sequences of the CDR regions of the monoclonal antibody sequences in (1) to (13) below were analyzed by technical means well known to those skilled in the art, for example by VBASE2 database and according to the IMGT definition, and the results are as follows:

(1) Bevacizumab

The amino acid sequence of the heavy chain variable region is set forth in SEQ ID NO: 5, and the amino acid sequence of the light chain variable region is set forth in SEQ ID NO: 7.

The amino acid sequences of the 3 CDR regions of its heavy chain variable region are as follows:

The amino acid sequences of the 3 CDR regions of its light chain variable region are as follows:

```
HCDR1:
                                        (SEQ ID NO: 15)
GYTFTNYG

HCDR2:
                                        (SEQ ID NO: 16)
INTYTGEP
```

```
HCDR3:
                                        (SEQ ID NO: 17)
AKYPHYYGSSHWYFDV

LCDR1:
                                        (SEQ ID NO: 18)
QDISNY

LCDR2:
FTS

LCDR3:
                                        (SEQ ID NO: 20)
QQYSTVPWT
```

(2) 14C12H1L1

The amino acid sequence of the heavy chain variable region is set forth in SEQ ID NO: 9, and the amino acid sequence of the light chain variable region is set forth in SEQ ID NO: 11.

The amino acid sequences of the 3 CDR regions of its heavy chain variable region are as follows:

```
HCDR1:
                                        (SEQ ID NO: 21)
GFAFSSYD

HCDR2:
                                        (SEQ ID NO: 22)
ISGGGRYT

HCDR3:
                                        (SEQ ID NO: 23)
ANRYGEAWFAY
```

The amino acid sequences of the 3 CDR regions of its light chain variable region are as follows:

```
LCDR1:
                                        (SEQ ID NO: 24)
QDINTY

LCDR2:
RAN

LCDR3:
                                        (SEQ ID NO: 26)
LQYDEFPLT
```

(3) VP101

The amino acid sequences of the 9 CDR regions of its heavy chains are as follows:

```
HCDR1:
                                        (SEQ ID NO: 15)
GYTFTNYG

HCDR2:
                                        (SEQ ID NO: 16)
INTYTGEP

HCDR3:
                                        (SEQ ID NO: 17)
AKYPHYYGSSHWYFDV

HCDR4:
                                        (SEQ ID NO: 21)
GFAFSSYD

HCDR5:
                                        (SEQ ID NO: 22)
ISGGGRYT
```

```
HCDR6:
                                         (SEQ ID NO: 23)
ANRYGEAWFAY

HCDR7:
                                         (SEQ ID NO: 24)
QDINTY

HCDR8:
RAN

HCDR9:
                                         (SEQ ID NO: 26)
LQYDEFPLT
```

The amino acid sequences of the 3 CDR regions of its light chain variable region are as follows:

```
LCDR1:
                                         (SEQ ID NO: 18)
QDISNY

LCDR2:
FTS

LCDR3:
                                         (SEQ ID NO: 20)
QQYSTVPWT
```

In the present application, unless otherwise defined, the scientific and technical terms used herein have the meanings generally understood by those skilled in the art. In addition, the laboratory operations of cell culture, molecular genetics, nucleic acid chemistry and immunology used herein are the routine procedures widely used in the corresponding fields. Meanwhile, in order to better understand the present application, the definitions and explanations of the relevant terms are provided below.

As used herein, when referring to the amino acid sequence of VEGFR2 protein (also known as KDR, GenBank ID: NP_002244), it includes the full length of the VEGFR2 protein, or the extracellular fragment VEGFR2-ECD of VEGFR2, or a fragment comprising VEGFR2-ECD, and it also includes a fusion protein of VEGFR2-ECD, such as a fragment fused to an Fc protein fragment of mouse or human IgG (mFc or hFc). However, those skilled in the art will appreciate that in the amino acid sequence of the VEGFR2 protein, mutations or variations (including but not limited to, substitutions, deletions and/or additions) can be naturally generated or artificially introduced without affecting biological functions thereof. Therefore, in the present application, the term "VEGFR2 protein" should include all such sequences, including their natural or artificial variants. In addition, when describing the sequence fragment of the VEGFR2 protein, it also includes the corresponding sequence fragments in its natural or artificial variants. In one embodiment of the present application, the amino acid sequence of the extracellular fragment VEGFR2-ECD of VEGFR2 is shown in amino acids 1-766 of SEQ ID NO: 3 (766 amino acids).

As used herein, when referring to the amino acid sequence of VEGFR2 protein (also known as KDR, GenBank ID: NP_002244), it includes the full length of the VEGFR2 protein, or the extracellular fragment VEGFR2-ECD of VEGFR2, or a fragment comprising VEGFR2-ECD, and it also includes a fusion protein of VEGFR2-ECD, such as a fragment fused to an Fc protein fragment of mouse or human IgG (mFc or hFc). However, those skilled in the art will appreciate that in the amino acid sequence of the VEGFR2 protein, mutations or variations (including but not limited to, substitutions, deletions and/or additions) can be naturally generated or artificially introduced without affecting biological functions thereof. Therefore, in the present application, the term "VEGFR2 protein" should include all such sequences, including their natural or artificial variants. In addition, when describing the sequence fragment of the VEGFR2 protein, it also includes the corresponding sequence fragments in its natural or artificial variants. In one embodiment of the present application, the amino acid sequence of the extracellular fragment VEGFR2-ECD of VEGFR2 is shown in amino acids 1-766 of SEQ ID NO: 4 (766 amino acids).

As used herein, unless otherwise specified, the VEGFR is VEGFR1 and/or VEGFR2; specific protein sequence thereof is a sequence known in the prior art, and reference may be made to the sequence disclosed in the existing literature or GenBank. For example, VEGFR1 (VEGFR1, NCBI Gene ID: 2321); VEGFR2 (VEGFR2, NCBI Gene ID: 3791).

As used herein, when referring to the amino acid sequence of PD-1 protein (Programmed cell death protein 1, NCBI GenBank: NM_005018), it includes the full length of the PD-1 protein, or the extracellular fragment PD-1ECD of PD-1 or a fragment comprising PD-1ECD, and it also includes a fusion protein of PD-1ECD, such as a fragment fused to an Fc protein fragment of a mouse or human IgG (mFc or hFc). However, it will be appreciated by those skilled in the art that in the amino acid sequence of PD-1 protein, mutations or variations (including but not limited to substitutions, deletions and/or additions) can be naturally generated or artificially introduced without affecting biological functions thereof. Therefore, in the present application, the term "PD-1 protein" should include all such sequences, including their natural or artificial variants. In addition, when describing the sequence fragment of the PD-1 protein, it also includes the corresponding sequence fragments in its natural or artificial variants.

As used herein, the term $EC_{50}$ refers to the concentration for 50% of maximal effect, i.e. the concentration that can cause 50% of the maximal effect.

As used herein, the term "antibody" refers to an immunoglobulin molecule that generally consists of two pairs of polypeptide chains (each pair with one "light" (L) chain and one "heavy" (H) chain). In a general sense, the heavy chain can be interpreted as a polypeptide chain with a larger molecular weight in an antibody, and the light chain refers to a polypeptide chain with a smaller molecular weight in an antibody. Light chains are classified as κ and λ light chains. Heavy chains are generally classified as μ, δ, γ, α, or ε, and isotypes of antibodies are defined as IgM, IgD, IgG, IgA, and IgE, respectively. In light chains and heavy chains, the variable region and constant region are linked by a "J" region of about 12 or more amino acids, and the heavy chain also comprises a "D" region of about 3 or more amino acids. Each heavy chain consists of a heavy chain variable region ($V_H$) and a heavy chain constant region ($C_H$). The heavy chain constant region consists of 3 domains ($C_{H1}$, $C_{H2}$, and $C_{H3}$). Each light chain consists of a light chain variable region ($V_L$) and a light chain constant region ($C_L$). The light chain constant region consists of one domain $C_L$. The constant region of the antibody can mediate the binding of immunoglobulins to host tissues or factors, including the binding of various cells of the immune system (e.g., effector cells) to the first component (C1q) of classical complement system. The $V_H$ and $V_L$ regions can be further subdivided into highly variable regions (called Complementarity Determining Regions (CDRs)), between which conservative regions called framework regions (FRs) are distributed. Each $V_H$ and $V_L$ consists of 3 CDRs and 4 FRs arranged from amino terminus to carboxyl terminus in the following order: FR1, CDR1, FR2, CDR2, FR3, CDR3, FR4. The variable regions ($V_H$ and $V_L$) of each heavy chain/light chain pair form antibody binding sites, respectively. The assignment of amino acids to the regions or domains may be based on Kabat Sequences of Proteins of Immunological Interest (National Institutes of Health, Bethesda, Md. (1987 and 1991)), or Chothia & Lesk *J. Mol. Biol.* 196 (1987): 901-917; Chothia et al. *Nature* 342 (1989): 878-883 or the definition of IMGT numbering system, see Ehrenmann, Francois, Quentin Kaas, and Marie-Paule Lefranc. "IMGT/3Dstructure-DB and IMGT/DomainGapAlign: a database and a tool for immunoglobulins or antibodies, T cell receptors, MHC, IgSF and MhcSF." *Nucleic acids research* 38.suppl_1 (2009): D301-D307. In particular, the heavy chain may also comprise more than 3 CDRs, such as 6, 9, or 12. For example, in the bispecific antibody of the present application, the heavy chain may be a ScFv with the C-terminus of the heavy chain of IgG antibody linked to another antibody, and in this case, the heavy chain comprises 9 CDRs. The term "antibody" is not limited by any specific method for producing antibody. For example, the antibody includes, in particular, a recombinant antibody, a monoclonal antibody, and a polyclonal antibody. Antibodies can be different isotypes, such as antibody IgG (e.g., subtype IgG1, IgG2, IgG3 or IgG4), IgA1, IgA2, IgD, IgE or IgM.

As used herein, the term "antigen binding fragment", also known as the "antigen binding portion", refers to a polypeptide comprising the fragment of a full-length antibody, which maintains the ability to specifically bind to the same antigen to which the full-length antibody binds, and/or competes with the full-length antibody for the specific binding to an antigen. See generally, Fundamental Immunology, Ch. 7 (Paul, W., ed., 2nd edition, Raven Press, N.Y. (1989), which is incorporated by reference herein in its entirety for all purposes. An antigen-binding fragment of an antibody can be produced by recombinant DNA technique or by enzymatic or chemical cleavage of an intact antibody. In some cases, the antigen binding fragment includes Fab, Fab', F(ab')$_2$, Fd, Fv, dAb, and complementarity determining region (CDR) fragment, single chain antibody fragment (e.g., scFv), chimeric antibody, diabody and polypeptide that comprises at least a portion of an antibody sufficient to impart specific antigen binding ability to a polypeptide.

As used herein, the term "Fd fragment" refers to an antibody fragment consisting of $V_H$ and $C_{H1}$ domains; the term "Fv fragment" refers to an antibody fragment consisting of the $V_L$ and $V_H$ domains of a single arm of an antibody; the term "dAb fragment" refers to an antibody fragment consisting of a $V_H$ domain (Ward et al., *Nature* 341 (1989): 544-546); the term "Fab fragment" refers to an antibody fragment consisting of $V_L$, $V_H$, $C_L$ and $C_{H1}$ domains; and the term "F(ab')$_2$ fragment" refers to an antibody fragment comprising two Fab fragments linked by the disulfide bridge on a hinge region.

In some cases, the antigen binding fragment of the antibody is a single chain antibody (e.g., scFv) in which the $V_L$ and $V_H$ domains are paired to form a monovalent molecule via a linker that enables them to produce a single polypeptide chain (see, e.g., Bird et al., *Science* 242 (1988):423-426 and Huston et al., *Proc. Natl. Acad. Sci. USA* 85 (1988): 5879-5883). Such scFv molecules may have a general structure: NH$_2$-V$_L$-linker-V$_H$—COOH or NH$_2$-V$_H$-linker-V$_L$-COOH. An appropriate linker in prior art consists of a repeating GGGGS (SEQ ID NO: 14) amino acid sequence or a variant thereof. For example, a linker having the amino acid sequence (GGGGS)$_4$ (SEQ ID NO:13) can be used, and variants thereof can also be used (Holliger et al., *Proc. Natl. Acad. Sci. USA* 90 (1993):6444-6448). Other linkers useful in the present application are described by Alfthan et al., *Protein Eng.* 8 (1995):725-731, Choi et al., *Eur. J. Immunol.* 31 (2001):94-106, Hu et al., *Cancer Res.* 56 (1996):3055-3061, Kipriyanov et al., *J. Mol. Biol.* 293 (1999):41-56, and Roovers et al., *Cancer Immunol.* (2001).

In some cases, the antigen binding fragment of the antibody is a diabody, that is, a bivalent antibody, in which the $V_H$ and $V_L$ domains are expressed on a single polypeptide chain. However, the linker used is too short to allow the pairing of the two domains on the same chain, thereby the domains are forced to pair with the complementary domains on the other chain and two antigen binding sites are generated (see, e.g., Holliger P. et al., *Proc. Natl. Acad. Sci. USA* 90 (1993):6444-6448, and Poljak R J et al., *Structure* 2 (1994):1121-1123).

Antigen binding fragments (e.g., the above mentioned antibody fragments) of antibodies can be obtained from given antibodies by using conventional techniques known to those skilled in the art (e.g., recombinant DNA technique or enzymatic or chemical cleavage), and the antigen binding fragments of the antibodies are screened for specificity in the same way as for intact antibodies.

As used herein, unless otherwise clearly defined in the context, when referring to the term "antibody", it includes not only intact antibodies but also antigen binding fragments of antibodies.

As used herein, the terms "mAb" and "monoclonal antibody" refer to an antibody or a fragment thereof that is derived from a group of highly homologous antibodies, i.e. from a group of identical antibody molecules, except for natural mutations that may occur spontaneously. The monoclonal antibody has a high specificity for a single epitope on an antigen. The polyclonal antibody, relative to the monoclonal antibody, generally comprises at least two or more different antibodies which generally recognize different epitopes on an antigen. Monoclonal antibodies can generally be obtained by hybridoma technique first reported by Kohler et al. (*Nature,* 256:495, 1975), and can also be obtained by recombinant DNA technique (for example, see U.S. Pat. No. 4,816,567).

As used herein, the term "chimeric antibody" refers to an antibody of which a part of the light or/and heavy chains is derived from an antibody (which may be derived from a specific species or belong to a specific antibody class or subclass), and the other part of the light or/and heavy chains are derived from another antibody (which may be derived from the same or different species or belong to the same or different antibody class or subclass). But in any case, it retains the binding activity for the target antigen (U.S. Pat. No. 4,816,567 to Cabilly et al.; Morrison et al., *Proc. Natl. Acad. Sci. USA,* 81 (1984):6851-6855).

As used herein, the term "humanized antibody" refers to an antibody or antibody fragment obtained when all or a part of CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, e.g., Jones et al., *Nature*, 321 (1986):522-525; Reichmann et al., *Nature*, 332:323 329 (1988); Presta, *Curr. Op. Struct. Biol.*, 2 (1992):593-596, and Clark, *Immunol. Today* 21 (2000):397-402.

As used herein, the term "epitope" refers to a site on the antigen that an immunoglobulin or antibody specifically binds to. "Epitope" is also called in the art as an "antigenic determinant". The epitope or antigenic determinant generally consists of chemically active surface groups of a molecule such as amino acids or carbohydrates or sugar side chains, and usually has specific three-dimensional structural characteristics and specific charge characteristics. For example, the epitope generally includes at least 3, 4, 5, 6, 7, 8, 9, 10, 11, 12, 13, 14, or 15 consecutive or non-consecutive amino acids in a unique spatial conformation, which can be "linear" or "conformational". See, for example, Epitope Mapping Protocols in Methods in Molecular Biology, Vol. 66, G. E. Morris, Ed. (1996). In a linear epitope, all interacting sites between a protein and an interacting molecule (e.g., an antibody) exist linearly along the primary amino acid sequence of the protein. In a conformational epitope, the interacting sites exist across the protein amino acid residues that are separated from each other.

As used herein, the term "isolated" refers to obtained by artificial means from natural state. If a certain "isolated" substance or component appears in nature, it may be that change occurs in its natural environment, or that it is isolated from the natural environment, or both. For example, a certain non-isolated polynucleotide or polypeptide naturally exists in a certain living animal, and the same polynucleotide or polypeptide with a high purity isolated from such a natural state is called isolated polynucleotide or polypeptide. The term "isolated" does not exclude the existence of artificial or synthetic substances or other impurities that do not affect the activity of the substance.

As used herein, the term "vector" refers to a nucleic acid vehicle into which a polynucleotide can be inserted. When a vector allows for the expression of the protein encoded by the inserted polynucleotide, the vector is called an expression vector. A vector can be introduced into a host cell by transformation, transduction, or transfection so that the genetic substance elements carried by the vector can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC), or P1-derived artificial chromosome (PAC); phages such as lambda phages or M13 phages, and animal viruses. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papovaviruses (such as SV40). A vector can contain a variety of elements that control expression, including, but not limited to, promoter sequences, transcription initiation sequences, enhancer sequences, selection elements, and reporter genes. In addition, the vector may further contain a replication initiation site.

As used herein, the term "host cell" refers to cells to which the vector can be introduced, including but not limited to prokaryotic cells such as *E. coli* or *Bacillus subtilis*, fungal cells such as yeast cells or *aspergillus*, insect cells such as S2 *drosophila* cells or Sf9, or animal cells such as fibroblast, CHO cells, COS cells, NSO cells, HeLa cells, BHK cells, HEK 293 cells, or human cells.

As used herein, the term "specifically bind" refers to a non-random binding reaction between two molecules, such as a reaction between an antibody and an antigen it targets. In some embodiments, an antibody that specifically binds to an antigen (or an antibody that is specific for an antigen) means that the antibody binds to the antigen with an affinity ($K_D$) of less than about $10^{-5}$ M, such as less than about $10^{-6}$ M, $10^{-7}$ M, $10^{-8}$ M, $10^{-9}$ M or $10^{-10}$ M or less. In some embodiments of the present application, the term "target" refers to specific binding.

As used herein, the term "$K_D$" refers to a dissociation equilibrium constant for a specific antibody-antigen interaction, which is used to describe the binding affinity between the antibody and the antigen. The smaller the equilibrium dissociation constant, the tighter the antibody-antigen binding, and the higher the affinity between the antibody and the antigen. Generally, antibodies bind to antigens with a dissociation equilibrium constant ($K_D$) of less than about $10^{-5}$ M, such as less than about $10^{-6}$ M, $10^{-7}$ M, $10^{-8}$ M, $10^{-9}$ M or $10^{-10}$ M or less, for example, as determined in a BIACORE instrument using Surface Plasmon Resonance (SPR).

As used herein, the terms "monoclonal antibody" and "mAb" have the same meaning and can be used interchangeably; the terms "polyclonal antibody" and "PcAb" have the same meaning and can be used interchangeably; the terms "polypeptide" and "protein" have the same meaning and can be used interchangeably. Besides, in the present application, amino acids are generally represented by single-letter and three-letter abbreviations known in the art. For example, alanine can be represented by A or Ala.

As used herein, the term "pharmaceutically acceptable excipient" refers to a carrier and/or vehicle that is pharmacologically and/or physiologically compatible with the subject and the active ingredient, which is well known in the art (see, e.g., Remington's Pharmaceutical Sciences. Edited by Gennaro A R, 19th ed. Pennsylvania: Mack Publishing Company, 1995) and includes, but is not limited to, pH regulators, surfactants, adjuvants, and ionic strength enhancers. For example, the pH regulators include, but are not limited to, phosphate buffer; the surfactants include, but are not limited to, cationic, anionic, or non-ionic surfactants, such as Tween-80; the ionic strength enhancers include, but are not limited to, sodium chloride.

As used herein, the term "adjuvant" refers to a non-specific immune enhancer, which can enhance the immune response of an organism to antigens or change the type of immune response when delivered into the organism together with the antigens or delivered into the organism in advance. There are various adjuvants, including but not limited to aluminum adjuvant (such as aluminum hydroxide), Freund's adjuvant (such as complete Freund's adjuvant and incomplete Freund's adjuvant), *Corynebacterium parvum*, lipopolysaccharide, cytokine, etc. The Freund's adjuvant is the most commonly used adjuvant in animal experiments. The aluminum hydroxide adjuvant is used more in clinical trials.

As used herein, the term "effective amount" refers to an amount sufficient to obtain or at least partially obtain desired effect. For example, a prophylactically effective amount (e.g., for a disease associated with PD-1 binding to PD-L1 or overexpression of VEGF, such as a tumor) is an amount sufficient to prevent, stop, or delay the onset of the disease (e.g., a disease associated with PD-L1 binding to PD-L1 or overexpression of VEGF, such as a tumor); a therapeutically effective amount is an amount sufficient to cure or at least partially stop the disease and its complications in a patient suffering from the disease. It is undoubtedly within the ability of those skilled in the art to determine such an effective amount. For example, the amount effective for therapeutic use will depend on the severity of the disease to be treated, the overall state of the immune system of the patient, the general condition of the patient such as age, weight and sex, the mode of drug administration, and other treatments administered concurrently, etc.

Advantages of the Present Application

The bispecific antibody VP101 can specifically bind to VEGFA well, effectively block the binding of VEGFA to VEGFR2, and specifically relieve the immunosuppression of VEGFA in an organism and the promoting effect of VEGFA on angiogenesis; VP101 can specifically bind to PD-1 well, effectively block the binding of PD-1 to PD-L1, and specifically relieve the immunosuppression of PD-1 in an organism, and activate the immune response.

DETAILED DESCRIPTION

Figure 1:
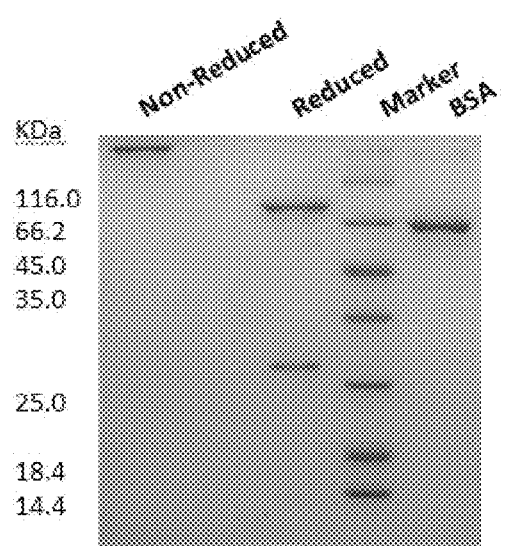
FIG. 1 shows the SDS-PAGE detection results of bifunctional antibody VP101. The samples of the four lanes from left to right and their respective loading amounts are: antibody in non-reduced protein electrophoresis loading buffer, 1 μg; antibody in reduced protein electrophoresis loading buffer, 1 μg; Marker, 5 μL; BSA, 1 μg.
Figure 2:
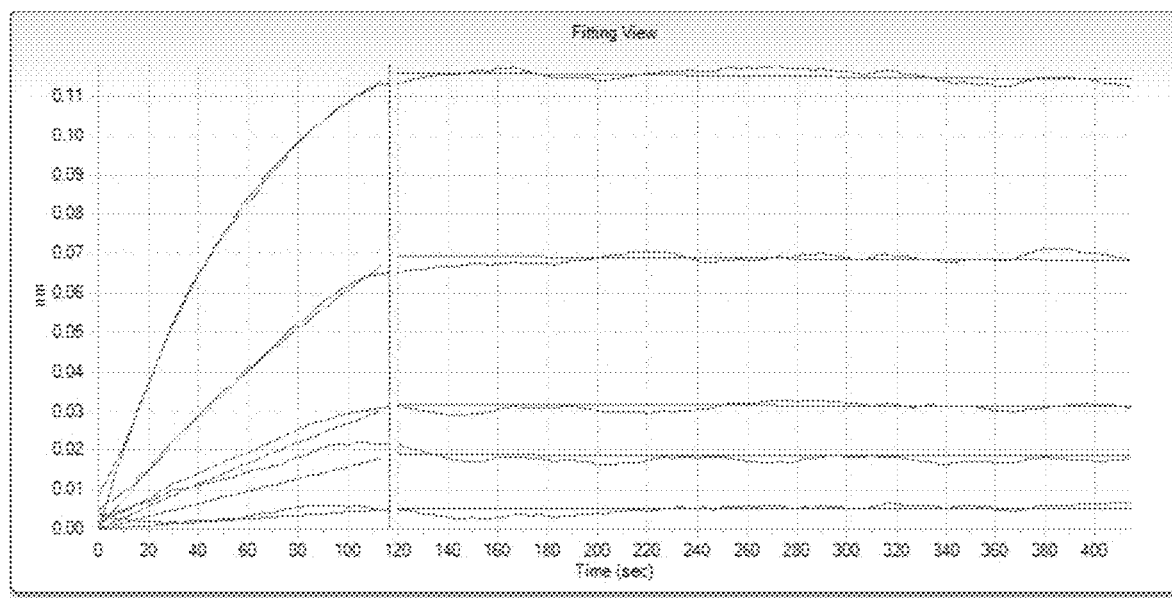
FIG. 2 shows the detection results of kinetic characteristic parameters of the binding of antibody VP101 to PD-1.
Figure 3:
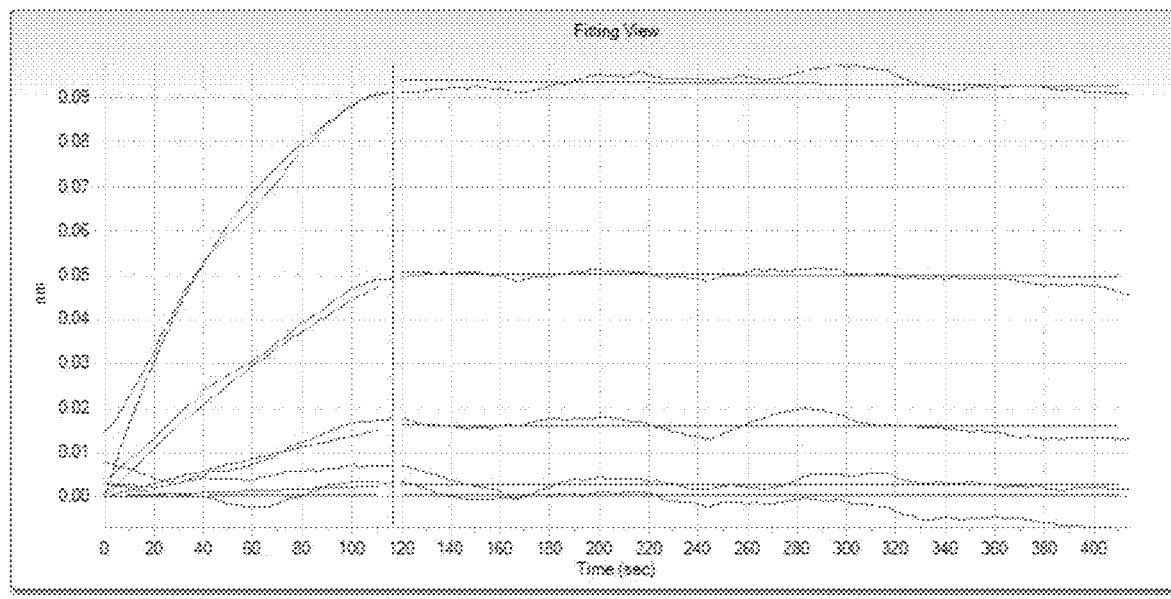
FIG. 3 shows the detection results of kinetic characteristic parameters of the binding of antibody BsAbB7 to PD-1.
Figure 4:
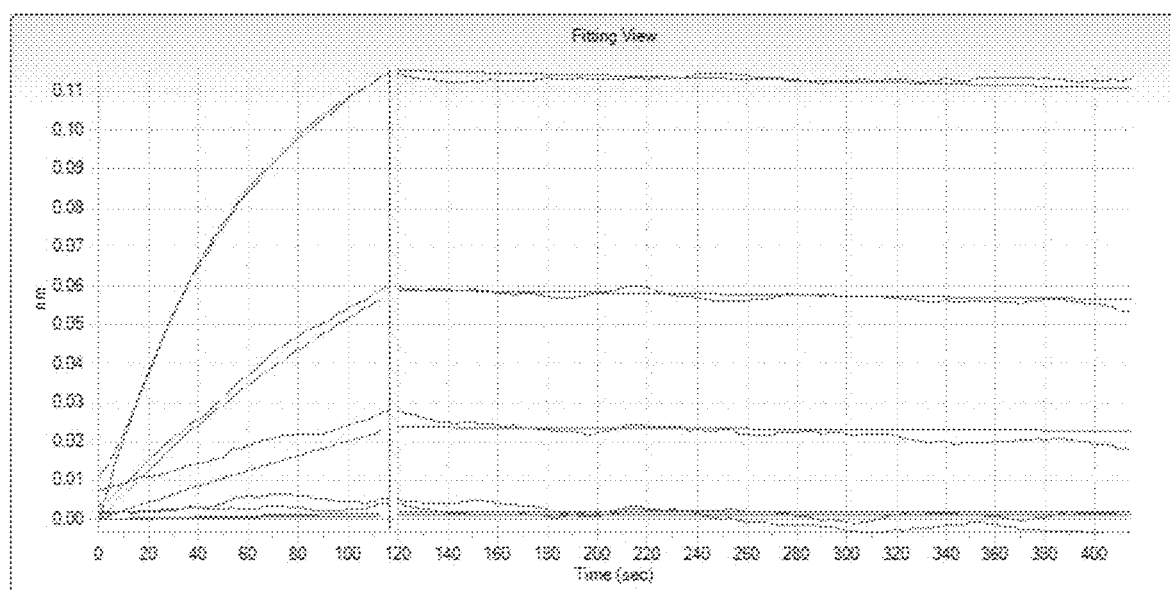
FIG. 4 shows the detection results of kinetic characteristic parameters of the binding of antibody BsAbB8 to PD-1.
Figure 5:
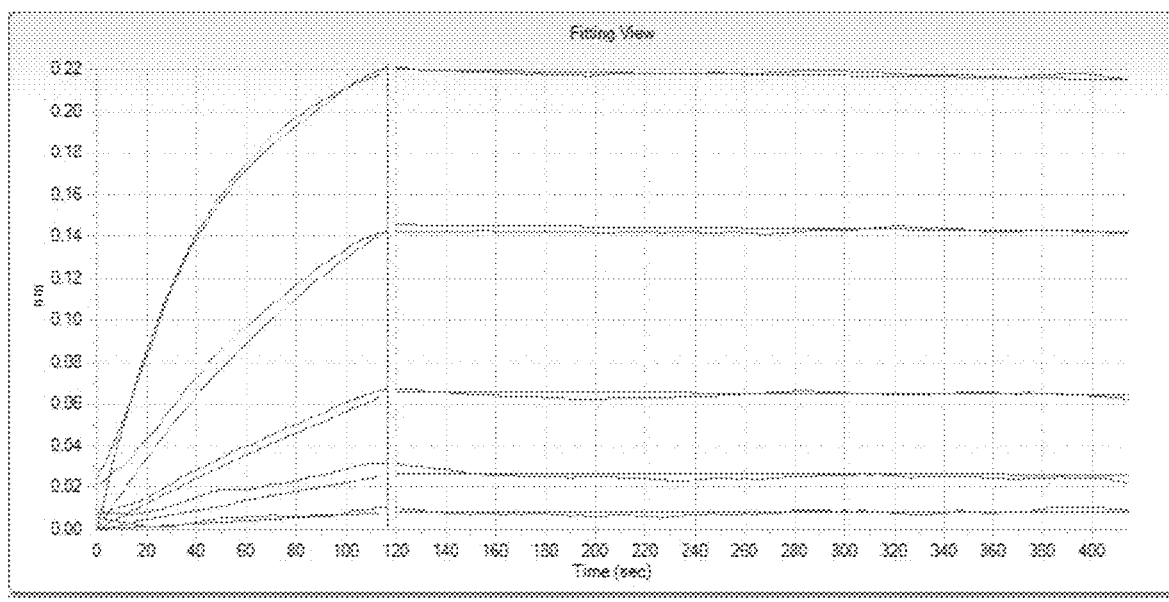
FIG. 5 shows the detection results of kinetic characteristic parameters of the binding of antibody 14C12H1L1 to PD-1.
Figure 6:
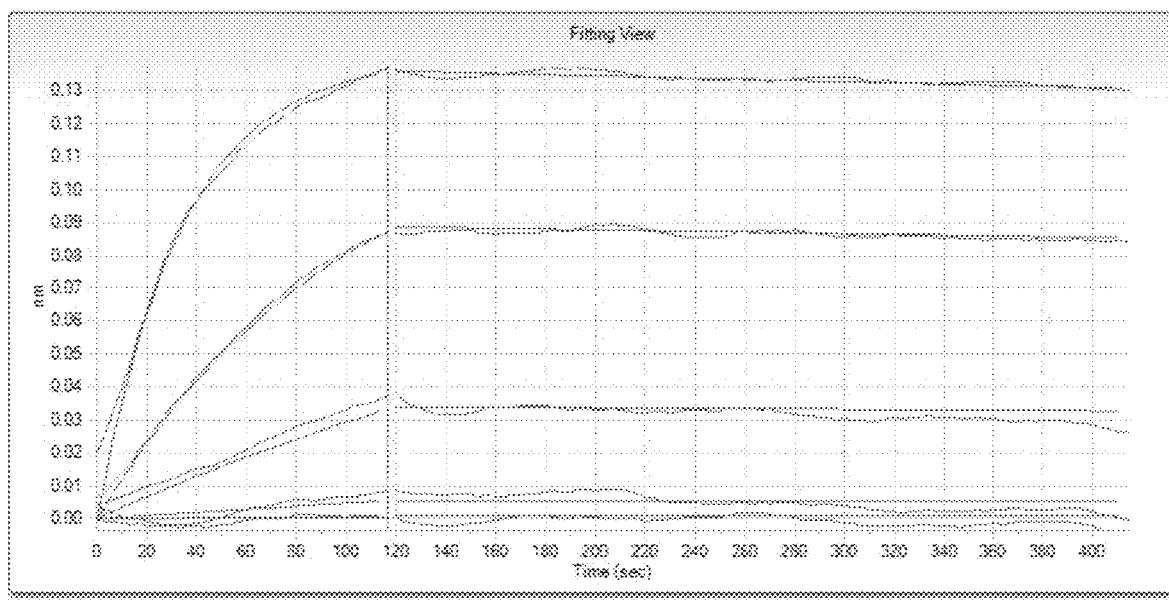
FIG. 6 shows the detection results of kinetic characteristic parameters of the binding of antibody nivolumab to PD-1.
Figure 7:
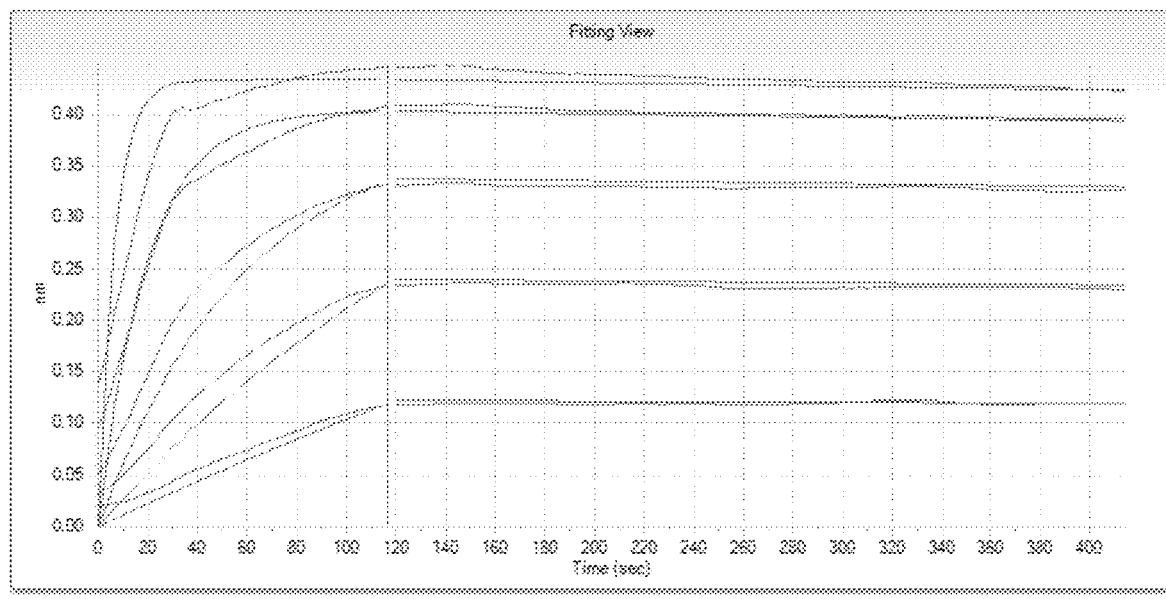
FIG. 7 shows the detection results of kinetic characteristic parameters of the binding of antibody VP101 to VEGF.
Figure 8:
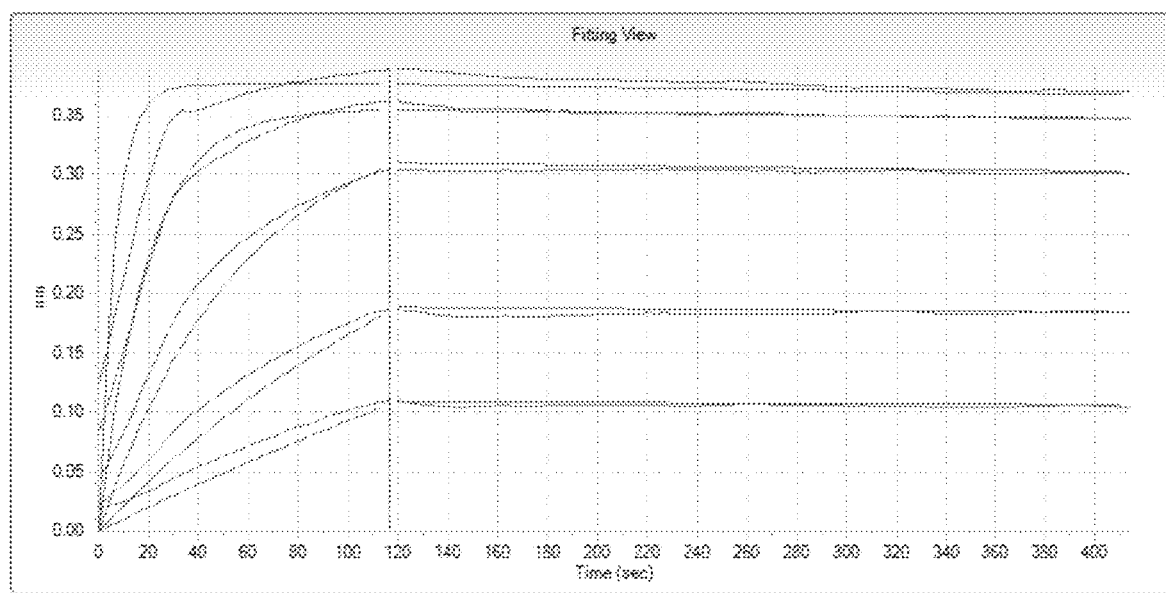
FIG. 8 shows the detection results of kinetic characteristic parameters of the binding of antibody BsAbB7 to VEGF.
Figure 9:
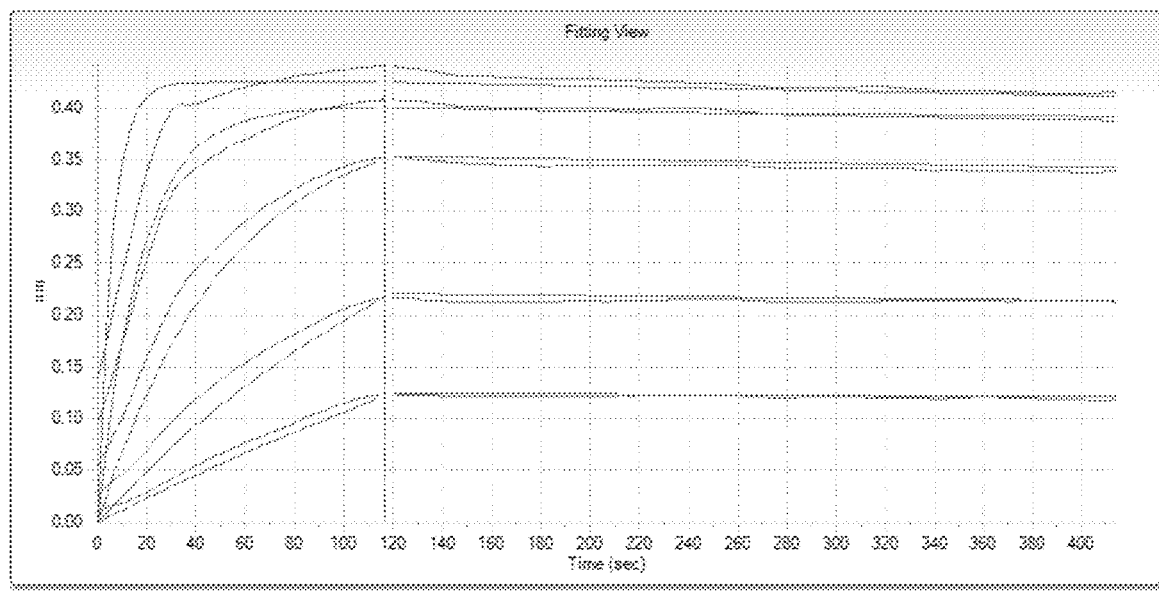
FIG. 9 shows the detection results of kinetic characteristic parameters of the binding of antibody BsAbB8 to VEGF.
Figure 10:
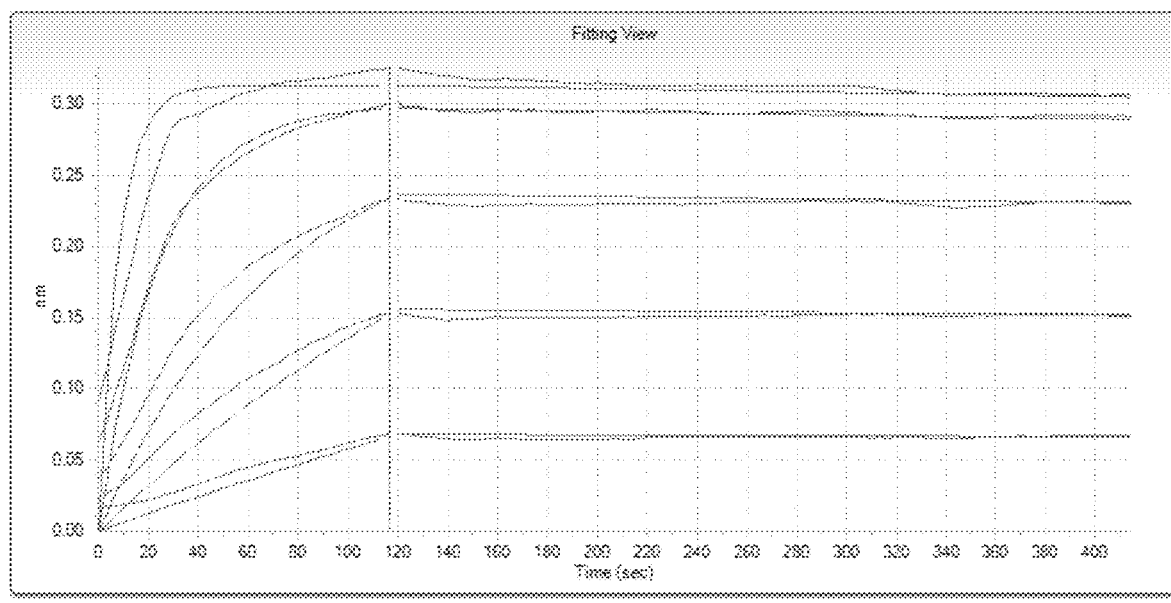
FIG. 10 shows the detection results of kinetic characteristic parameters of the binding of antibody bevacizumab to VEGF.

The embodiments of the present application will be described in detail below with reference to the examples. Those skilled in the art will understand that the following examples are only used for illustrative purposes, and should not be regarded as limiting the scope of the present invention. The cases without the specific descriptions of techniques or conditions were carried out according to the technologies or conditions described in the literature in the art (e.g., see, Guide to Molecular Cloning Experiments, authored by J. Sambrook et al., and translated by Huang Peitang et al., third edition, Science Press) or according to the product manual. Reagents or instruments used are all commercially available conventional products if the manufacturers thereof are not specified.

In the following examples, the marketed antibody bevacizumab (trade name AVASTIN®) for the same target was purchased from Roche as a control antibody, or was prepared according to Preparation Example 4.

In the following examples, the marketed antibody nivolumab for the same target (trade name OPDIVO®) was purchased from BMS as a control antibody.

In the following examples, the amino acid sequences of the control antibodies BsAbB7 and BsAbB8 were identical to the amino acid sequences of BsAbB7 and BsAbB8 respectively in Chinese Patent Publication CN105175545A.

Preparation Example 1: Preparation of Fusion Proteins PD-1-mFc, PD-1-hFc and PD-L1-hFc The preparation of fusion proteins PD-1-mFc, PD-1-hFc and PD-L1-hFc and the SDS-PAGE electrophoresis detection are carried out by fully referring to Preparation Example 1 of Chinese Patent Publication CN106632674A.

The amino acid sequences and the encoding nucleotide sequences of the fusion proteins PD-1-mFc, PD-1-hFc and PD-L1-hFc in this preparation example are the same as those of PD-1-mFc, PD-1-hFc and PDL-1-hFc respectively in the Preparation Example 1 of Chinese Patent Publication CN106632674A.

Fusion proteins PD-1-mFc, PD-1-hFc and PD-L1-hFc were thus obtained.

Preparation Example 2: Expression and Purification of Fusion Protein VEGFA-His

1. Construction of Plasmid VEGFA-His

PCR amplification was performed using VEGFA human cDNA (purchased from Origene) as a template and the hVEGFA-His fragment was purified and isolated using an ordinary DNA product purification kit. The isolated hVEGFA-His fragment and an expression vector pcDNA3.1 were enzyme-digested with XbaI&HindIII-HF, and a target gene fragment was isolated by gel extraction and ligated with a linear expression vector by T4 ligase. Then all the ligation products were transformed into DH5a chemically competent cells and coated on an Agar plate with Amp. Well separated single colonies were selected for colony PCR identification, PCR positive clones were inoculated to an LB culture medium for culture, and a bacteria solution was taken and sent to Guangzhou Invitrogen Biotechnology for sequencing verification. The alignment of the sequencing results showed that the insertion sequence of the positive recon was completely correct.

2. Expression and Purification of Fusion Protein VEGFA-His

After the recombinant plasmid VEGFA-his was transfected into 293F cells (purchased from Invitrogen) for 7 days according to the manual in lipofectamin transfection kit (purchased from Invitrogen), the culture medium was subjected to high-speed centrifugation, supernatant concentration and buffer exchange into Binding Buffer A, and then loaded onto a HisTrap column, and proteins were linearly eluted with Elution Buffer A. The primary pure sample was subjected to buffer exchange into Binding Buffer B with a HiTrap Desalting column and loaded onto a HiTrap Q column, proteins were linearly eluted with Elution Buffer B, and the target sample was isolated and buffer exchanged into PBS. The purified sample was added to a reduced protein electrophoresis loading buffer for SDS-PAGE electrophoresis detection.

The fusion protein VEGFA-His was thus obtained.

The amino acid sequence of VEGFA-His is as follows (171 aa):

(SEQ ID NO: 1)
APMAEGGGQNHHEVVKFMDVYQRSYCHPIETLVDIFQEYPDEIEYIFKPS

CVPLMRCGGCCNDEGLECVPTEESNITMQIMRIKPHQGQHIGEMSFLQHN

KCECRPKKDRARQENPCGPCSERRKHLFVQDPQTCKCSCKNTDSRCKARQ

LELNERTCRCDKPRRHHHHHH wherein, amino acids 1-165 of SEQ ID NO:1 is VEGFA.

Nucleotide sequence encoding VEGFA-His (513 bp)

(SEQ ID NO: 2)
GCACCCATGGCCGAGGGCGGCGGCCAGAACCACCACGAGGTGGTGAAGTT

CATGGACGTGTACCAGAGAAGCTACTGCCACCCCATCGAGACCCTGGTGG

ACATCTTCCAGGAGTACCCCGACGAGATCGAGTACATCTTCAAGCCCAGC

TGCGTGCCCCTGATGAGATGCGGCGGCTGCTGCAACGACGAGGGCCTGGA

GTGCGTGCCCACCGAGGAGAGCAACATCACCATGCAGATCATGAGAATCA

AGCCCCACCAGGGCCAGCACATCGGCGAGATGAGCTTCCTGCAGCACAAC

AAGTGCGAGTGCAGACCCAAGAAGGACAGAGCCAGACAGGAGAACCCCTG

CGGCCCCTGCAGCGAGAGAAGAAAGCACCTGTTCGTGCAGGACCCCCAGA

CCTGCAAGTGCAGCTGCAAGAACACCGACAGCAGATGCAAGGCCAGACAG

CTGGAGCTGAACGAGAGAACCTGCAGATGCGACAAGCCCAGAAGACATCA

TCACCATCACCAC

Preparation Example 3: Expression and Purification of Fusion Protein VEGFR2-hFc

1. Synthesis of Gene VEGFR2-hFc:

The amino acids corresponding to the extracellular fragment VEGFR2 ECD of gene VEGFR2 (Vascular Endothelial Growth Factor Receptor 2, NCBI GenBank: NP_002244) were fused with TEV and the Fc protein fragment of human IgG (hFc) respectively (SEQ ID NO: 3). Genscript was entrusted to synthesize corresponding encoding nucleotide sequence (SEQ ID NO: 4).

VEGFR2, Vascular Endothelial Growth Factor Receptor 2, NCBI GenBank NP_002244;
 hFc: Ig gamma-1 chain C region, Uniprot ACCESSION: P01857, 106-330;
 Amino acid sequence of fusion protein VEGFR2-hFc: (998 aa)

(SEQ ID NO: 3)
MQSKVLLAVALWLCVETRAASVGLPSVSLDLPRLSIQKDILTIKANTTLQITCRGQRDLD

WLWPNNQSGSEQRVEVTECSDGLFCKTLTIPKVIGNDTGAYKCFYRETDLASVIYVYVQ

DYRSPFIASVSDQHGVVYITENKNKTVVIPCLGSISNLNVSLCARYPEKRFVPDGNRISW

-continued

```
DSKKGFTIPSYMISYAGMVFCEAKINDESYQSIMYIVVVVGYRIYDVVLSPSHGIELSVGE

KLVLNCTARTELNVGIDFNWEYPSSKHQHKKLVNRDLKTQSGSEMKKFLSTLTIDGVTR

SDQGLYTCAASSGLMTKKNSTFVRVHEKPFVAFGSGMESLVEATVGERVRIPAKYLGY

PPPEIKWYKNGIPLESNHTIKAGHVLTIMEVSERDTGNYTVILTNPISKEKQSHVVSLVVY

VPPQIGEKSLISPVDSYQYGTTQTLTCTVYAIPPPHHIHWYWQLEEECANEPSQAVSVTN

PYPCEEWRSVEDFQGGNKIEVNKNQFALIEGKNKTVSTLVIQAANVSALYKCEAVNKV

GRGERVISFHVTRGPEITLQPDMQPTEQESVSLWCTADRSTFENLTWYKLGPQPLPIHVG

ELPTPVCKNLDTLWKLNATMFSNSTNDILIMELKNASLQDQGDYVCLAQDRKTKKRHC

VVRQLTVLERVAPTITGNLENQTTSIGESIEVSCTASGNPPPQIMWFKDNETLVEDSGIVL

KDGNRNLTIRRVRKEDEGLYTCQACSVLGCAKVEAFFIIEGAQEKTNLESR ENLYFQG T

HTCPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK
``` wherein, amino acids 1-766 are the ECD part of VEGFR2, amino acids 767-773 are the TEV enzyme digestion site, and amino acids 774-998 are the hFc part.

Nucleotide sequence encoding fusion protein VEGFR2-hFc: (2997 bp)

(SEQ ID NO: 4)
```
ATGCAGAGCAAGGTGCTGCTGGCCGTCGCCTTGTGGCTCTGCGTGGAGACCCGGGC

CGCCTCTGTGGGTTTGCCTAGTGTTTCTCTTGATCTGCCCAGGCTCAGCATACAAAAA

GACATACTTACAATTAAGGCTAATACAACTCTTCAAATTACTTGCAGGGGACAGAGG

GACTTGGACTGGCTTTGGCCCAATAATCAGAGTGGCAGTGAGCAAAGGGTGGAGGT

GACTGAGTGCAGCGATGGCCTCTTCTGTAAGACACTCACAATTCCAAAAGTGATCGG

AAATGACACTGGAGCCTACAAGTGCTTCTACCGGGAAACTGACTTGGCCTCGGTCAT

TTATGTCTATGTTCAAGATTACAGATCTCCATTTATTGCTTCTGTTAGTGACCAACAT

GGAGTCGTGTACATTACTGAGAACAAAAACAAAACTGTGGTGATTCCATGTCTCGG

GTCCATTTCAAATCTCAACGTGTCACTTTGTGCAAGATACCCAGAAAAGAGATTTGT

TCCTGATGGTAACAGAATTTCCTGGGACAGCAAGAAGGGCTTTACTATTCCCAGCTA

CATGATCAGCTATGCTGGCATGGTCTTCTGTGAAGCAAAAATTAATGATGAAAGTTA

CCAGTCTATTATGTACATAGTTGTCGTTGTAGGGTATAGGATTTATGATGTGGTTCTG
```

-continued
AGTCCGTCTCATGGAATTGAACTATCTGTTGGAGAAAAGCTTGTCTTAAATTGTACA

GCAAGAACTGAACTAAATGTGGGGATTGACTTCAACTGGGAATACCCTTCTTCGAAG

CATCAGCATAAGAAACTTGTAAACCGAGACCTAAAAACCCAGTCTGGGAGTGAGAT

GAAGAAATTTTTGAGCACCTTAACTATAGATGGTGTAACCCGGAGTGACCAAGGATT

GTACACCTGTGCAGCATCCAGTGGGCTGATGACCAAGAAGAACAGCACATTTGTCA

GGGTCCATGAAAAACCTTTTGTTGCTTTTGGAAGTGGCATGGAATCTCTGGTGGAAG

CCACGGTGGGGGAGCGTGTCAGAATCCCTGCGAAGTACCTTGGTTACCCACCCCCA

GAAATAAAATGGTATAAAAATGGAATACCCCTTGAGTCCAATCACACAATTAAAGC

GGGGCATGTACTGACGATTATGGAAGTGAGTGAAAGAGACACAGGAAATTACACTG

TCATCCTTACCAATCCCATTTCAAAGGAGAAGCAGAGCCATGTGGTCTCTCTGGTTG

TGTATGTCCCACCCCAGATTGGTGAGAAATCTCTAATCTCTCCTGTGGATTCCTACCA

GTACGGCACCACTCAAACGCTGACATGTACGGTCTATGCCATTCCTCCCCCGCATCA

CATCCACTGGTATTGGCAGTTGGAGGAAGAGTGCGCCAACGAGCCCAGCCAAGCTG

TCTCAGTGACAAACCCATACCCTTGTGAAGAATGGAGAAGTGTGGAGGACTTCCAG

GGAGGAAATAAAATTGAAGTTAATAAAAATCAATTTGCTCTAATTGAAGGAAAAAA

CAAAACTGTAAGTACCCTTGTTATCCAAGCGGCAAATGTGTCAGCTTTGTACAAATG

TGAAGCGGTCAACAAAGTCGGGAGAGGAGAGAGGGTGATCTCCTTCCACGTGACCA

GGGGTCCTGAAATTACTTTGCAACCTGACATGCAGCCCACTGAGCAGGAGAGCGTG

TCTTTGTGGTGCACTGCAGACAGATCTACGTTTGAGAACCTCACATGGTACAAGCTT

GGCCCACAGCCTCTGCCAATCCATGTGGGAGAGTTGCCCACACCTGTTTGCAAGAAC

TTGGATACTCTTTGGAAATTGAATGCCACCATGTTCTCTAATAGCACAAATGACATT

TTGATCATGGAGCTTAAGAATGCATCCTTGCAGGACCAAGGAGACTATGTCTGCCTT

GCTCAAGACAGGAAGACCAAGAAAAGACATTGCGTGGTCAGGCAGCTCACAGTCCT

AGAGCGTGTGGCACCCACGATCACAGGAAACCTGGAGAATCAGACGACAAGTATTG

GGGAAAGCATCGAAGTCTCATGCACGGCATCTGGGAATCCCCCTCCACAGATCATG

TGGTTTAAAGATAATGAGACCCTTGTAGAAGACTCAGGCATTGTATTGAAGGATGG

GAACCGGAACCTCACTATCCGCAGAGTGAGGAAGGAGGACGAAGGCCTCTACACCT

GCCAGGCATGCAGTGTTCTTGGCTGTGCAAAAGTGGAGGCATTTTTCATAATAGAAG

GTGCCCAGGAAAAGACGAACTTGGAATCTAGA GAAAACCTGTATTTTCAGGGC ACT

-continued
```
CACACATGCCCACCGTGCCCAGCACCTGAACTCCTGGGGGGACCGTCAGTCTTCCTC

TTCCCCCCAAAACCCAAGGACACCCTCATGATCTCCCGGACCCCTGAGGTCACATGC

GTGGTGGTGGACGTGAGCCACGAAGACCCTGAGGTCAAGTTCAACTGGTACGTGGA

CGGCGTGGAGGTGCATAATGCCAAGACAAAGCCGCGGGAGGAGCAGTACAACAGC

ACGTACCGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAAACCAT

CTCCAAAGCCAAAGGGCAGCCCCGAGAACCACAGGTGTACACCCTGCCCCCATCCC

GGGATGAGCTGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACTACA

AGACCACGCCTCCCGTGTTGGACTCCGACGGCTCCTTCTTCCTCTACAGCAAGCTCA

CCGTGGACAAGAGCAGGTGGCAGCAGGGGAACGTCTTCTCATGCTCCGTGATGCAT

GAGGCTCTGCACAACCACTACACGCAGAAGAGCCTCTCCCTGTCTCCCGGGAAATG

A
``` wherein, nucleotides 1-2298 are the ECD part of VEGFR2, nucleotides 2299-2319 are the TEV enzyme digestion site, and nucleotides 2320-2997 are the hFc part.

2. Construction of Plasmid pUC57simple-VEGFR2-hFc:

The VEGFR2-hFc encoding gene synthesized by Genscript was cloned into an expression vector pUC57simple (provided by Genscript), and a pUC57simple-VEGFR2-hFc plasmid was obtained.

3. Construction of Recombinant Plasmid pcDNA3.1-VEGFR2-hFc:

The plasmid pUC57simple-VEGFR2-hFc was enzyme-digested (Xba I and BamH I), and the fusion gene fragment VEGFR2-hFc isolated by electrophoresis was ligated with expression vector pcDNA3.1 (purchased from Invitrogen) to give pcDNA3.1-VEGFR2-hFc, which was transfected into competent E. coli cell DH5a (purchased from TIANGEN); the transfection and culture were performed according to the manual. The positive pcDNA3.1-VEGFR2-hFc colonies were screened, E. coli was amplified according to a conventional method, and a kit (purchased from Tiangen Biotech (Beijing) Co., Ltd., DP103-03) was then used and a recombinant plasmid pcDNA3.1-VEGFR2-hFc was extracted according to the manual of the kit.

4. Transfection of Recombinant Plasmid pcDNA3.1-VEGFR2-hFc into 293F Cells

The recombinant plasmid pcDNA3.1-VEGFR2-hFc was transfected into 293F cells (purchased from Invitrogen) according to the lipofectamin transfection kit (purchased from Invitrogen).

5. SDS-PAGE Electrophoresis Detection of VEGFR2-hFc Protein

After transfecting the recombinant plasmid pcDNA3.1-VEGFR2-hFc into 293F cells for 7 days, the culture medium was subjected to high-speed centrifugation, microporous membrane vacuum filtration and purification in a Mabselect SuRe column to obtain a VEGFR2-hFc fusion protein sample, and a part of the sample was added into a reduced protein electrophoresis loading buffer for SDS-PAGE electrophoresis detection.

The fusion protein VEGFR2-hFc was thus obtained.

Preparation Example 4: Preparation of Anti-VEGFA Antibody Bevacizumab

Chinese Patent Publication CN1259962A is referred to for the amino acid sequences of the heavy chain variable region and the light chain variable region of the marketed VEGFA monoclonal antibody AVASTIN® (bevacizumab). Genscript was entrusted to synthesize nucleotide sequences encoding the heavy chain variable region and the light chain variable region.

Amino Acid Sequence of the Heavy Chain Variable Region of Bevacizumab: (123 Aa)

(SEQ ID NO: 5)
EVQLVESGGGLVQPGGSLRLSCAASGYTFTNYGMNWVRQAPGKGLEWVGW

INTYTGEPTYAADFKRRFTFSLDTSKSTAYLQMNSLRAEDTAVYYCAKYP

HYYGSSHWYFDVWGQGTLVTVSS

Nucleotide Sequence Encoding the Heavy Chain Variable Region of Bevacizumab: (369 bp)

(SEQ ID NO: 6)
GAGGTGCAGCTGGTCGAGTCCGGGGGGGGCTGGTGCAGCCAGGCGGGTC

TCTGAGGCTGAGTTGCGCCGCTTCAGGGTACACCTTCACAAACTATGGAA

TGAATTGGGTGCGCCAGGCACCAGGAAAGGGACTGGAGTGGGTCGGCTGG

ATCAACACTTACACCGGGGAACCTACCTATGCAGCCGACTTTAAGCGGCG

GTTCACCTTCAGCCTGGATACAAGCAAATCCACTGCCTACCTGCAGATGA

ACAGCCTGCGAGCTGAGGACACCGCAGTCTACTATTGTGCTAAATATCCC

CACTACTATGGGAGCAGCCATTGGTATTTTGACGTGTGGGGCAGGGGAC

TCTGGTGACAGTGAGCAGC

Amino Acid Sequence of the Light Chain Variable Region of Bevacizumab: (107 Aa)

(SEQ ID NO: 7)
DIQMTQSPSSLSASVGDRVTITCSASQDISNYLNWYQQKPGKAPKVLIYF

TSSLHSGVPSRFSGSGSGTDFTLTISSLQPEDFATYYCQQYSTVPWTFGQ

GTKVEIK

Nucleotide Sequence Encoding the Light Chain Variable Region of Bevacizumab: (321 bp)

(SEQ ID NO: 8)
GATATTCAGATGACTCAGAGCCCCTCCTCCCTGTCCGCCTCTGTGGGCGA

CAGGGTCACCATCACATGCAGTGCTTCACAGGATATTTCCAACTACCTGA

ATTGGTATCAGCAGAAGCCAGGAAAAGCACCCAAGGTGCTGATCTACTTC

ACTAGCTCCCTGCACTCAGGAGTGCCAAGCCGGTTCAGCGGATCCGGATC

TGGAACCGACTTTACTCTGACCATTTCTAGTCTGCAGCCTGAGGATTTCG

CTACATACTATTGCCAGCAGTATTCTACCGTGCCATGGACATTTGGCCAG

GGGACTAAAGTCGAGATCAAG

The heavy chain constant regions were all Ig gamma-1 chain C region, Uniprot ACCESSION: P01857; the light chain constant regions were all Ig kappa chain C region, Uniprot ACCESSION: P01834.

The heavy chain cDNA and the light chain cDNA of bevacizumab were cloned into vector pcDNA3.1, and the recombinant expression plasmid of the antibody bevacizumab was obtained. The recombinant plasmid was transfected into 293F cells. The 293F cell culture medium was purified and then detected.

The anti-VEGFA monoclonal antibody AVASTIN® (bevacizumab) was thus obtained.

Preparation Example 5; Preparation and Detection of Anti-PD-1 Humanized Antibody 14C12H1L1

The preparation was carried out according to the Examples 3-4 described in Chinese Patent Publication CN106977602A.

The amino acid sequences of the heavy chain variable region and the light chain variable region of humanized antibody 14C12H1L1, and the nucleotide sequence encoding the same are also the same as those described in Examples 3-4 of Chinese Patent Publication CN106977602A, and are also provided herein as follows:

Amino acid sequence of the heavy chain variable region of humanized antibody 14C12H1L1: (118 aa)

(SEQ ID NO: 9)
EVQLVESGGGLVQPGGSLRLSCAASGFAFSSYDMSWVRQAPGKGLDWVAT

ISGGGRYTYYPDSVKGRFTISRDNSKNNLYLQMNSLRAEDTALYYCANRY

GEAWFAYWGQGTLVTVSS

Nucleotide sequence encoding the heavy chain variable region of humanized antibody 14C12H1L1: (354 bp)

(SEQ ID NO: 10)
GAAGTGCAGCTGGTCGAGTCTGGGGGAGGGCTGGTGCAGCCCGGCGGGTC

ACTGCGACTGAGCTGCGCAGCTTCCGGATTCGCCTTTAGCTCCTACGACA

TGTCCTGGGTGCGACAGGCACCAGGAAAGGGACTGGATTGGGTCGCTACT

ATCTCAGGAGGCGGGAGATACACCTACTATCCTGACAGCGTCAAGGGCCG

GTTCACAATCTCTAGAGATAACAGTAAGAACAATCTGTATCTGCAGATGA

ACAGCCTGAGGGCTGAGGACACCGCACTGTACTATTGTGCCAACCGCTAC

GGGGAAGCATGGTTTGCCTATTGGGGCAGGGAACCCTGGTGACAGTCTC

TAGT

Amino acid sequence of the light chain variable region of humanized antibody 14C12H1L1: (107 aa)

(SEQ ID NO: 11)
DIQMTQSPSSMSASVGDRVTFTCRASQDINTYLSWFQQKPGKSPKTLIYR

ANRLVSGVPSRFSGSGSGQDYTLTISSLQPEDMATYYCLQYDEFPLTFGA

GTKLELK

Nucleotide sequence encoding the light chain variable region of humanized antibody 14C12H1L1: (321 bp)

(SEQ ID NO: 12)
GACATTCAGATGACTCAGAGCCCCTCCTCCATGTCCGCCTCTGTGGGCGA

CAGGGTCACCTTCACATGCCGCGCTAGTCAGGATATCAACACCTACCTGA

GCTGGTTTCAGCAGAAGCCAGGGAAAAGCCCCAAGACACTGATCTACCGG

GCTAATAGACTGGTGTCTGGAGTCCCAAGTCGGTTCAGTGGCTCAGGGAG

CGGACAGGACTACACTCTGACCATCAGCTCCCTGCAGCCTGAGGACATGG

CAACCTACTATTGCCTGCAGTATGATGAGTTCCCACTGACCTTTGGCGCC

GGGACAAAACTGGAGCTGAAG

The anti-PD-1 humanized antibody 14C12H1L1 was thus obtained.

Preparation Example 6: Preparation and Identification of hIgG

The sequence of Human Anti-Hen Egg Lysozyme IgG (anti-HEL, i.e., human IgG, abbreviated as hIgG) is derived from a variable region sequence of the Fab F10.6.6 sequence in the research published by Acierno et al., which is entitled "Affinity maturation increases the stability and plasticity of the Fv domain of anti-protein antibodies" (Acierno et al., *J Mol Biol.* 2007; 374 (1): 130-46). The preparation method is as follows:

Nanjing Genscript Biology was entrusted to carry out codon optimization of amino acids and gene synthesis on heavy and light chain (complete sequence or variable region) genes of human IgG antibody, and by referring to the standard technologies introduced in the "Guide to Molecular Cloning Experiments (Third Edition)" and using standard molecular cloning technologies such as PCR, enzyme digestion, DNA gel extraction, ligation transformation, colony PCR or enzyme digestion identification, the heavy and light chain genes were respectively subcloned into the antibody heavy chain expression vector and antibody light chain expression vector of the mammalian expression system, and the heavy and light chain genes of the recombinant expression vector were further sequenced and analyzed. After the sequence was verified to be correct, endotoxin-free expression plasmids were prepared in a large scale, and the heavy and light chain plasmids were transiently co-transfected into HEK293 cells for expression of recombinant antibody. After 7 days of culture, the cell culture medium was collected and affinity purified using an rProtein A column (GE), and the quality of the resulting antibody sample was determined using SDS-PAGE and SEC-HPLC standard analysis techniques.

The hIgG was thus obtained, and used in Examples 8-9 below.

Example 1: Sequence Design Preparation and Detection of Heavy and Light Chains of Bifunctional Antibody VP101

1. Sequence Design

The structure of the bifunctional antibody VP101 of the present application is in the Morrison form (IgG-scFv), i.e. C-termini of two heavy chains of an IgG antibody are each linked to a scFv fragment of another antibody, and the main composition design of the heavy and light chains is as shown in Table 1 below.

TABLE 1

| Bifunctional antibody No. | Composition design of the heavy and light chains of VP101 | | | Light chain |
|---|---|---|---|---|
| | Heavy chain | | | |
| | IgG part | Linker fragment | scFv part | |
| VP101 | Bevacizumab-H | Linker1 | 14C12H1$_v$-Linker1-14C12L1$_v$ | Bevacizumab-L |

In the Table 1 above:
(1) Those with "V" labeled at lower right corner refer to the variable region of corresponding heavy chain or the variable region of corresponding light chain. For those without "V" label, the corresponding heavy or light chain is the full length comprising the constant region. The corresponding sequences described in the above preparation examples are referred to for the amino acid sequences of these variable regions or the full length and the nucleotide sequences encoding them.
(2) The amino acid sequence of Linker1 is GGGGSGGGGGGGGSGGGGS (SEQ ID NO: 13)

2. Expression and Purification of Antibody VP101

The heavy chain cDNA sequence and the light chain cDNA sequence of VP101 were each cloned into vector pUC57simple (provided by Genscript) to obtain plasmids pUC57simple-VP101H and pUC57simple-VP101L, respectively.

Plasmids pUC57simple-VP101H and pUC57simple-VP101L were enzyme-digested (HindIII&EcoRI), and heavy and light chains isolated by electrophoresis were subcloned into vector pcDNA3.1, and recombinant plasmids were extracted to co-transfect 293F cells. After 7 days of cell culture, the culture medium was centrifuged at high speed, and the supernatant was concentrated and loaded onto a HiTrap MabSelect SuRe column. The protein was further eluted in one step with Elution Buffer, and the target sample antibody VP101 was isolated and buffer exchanged into PBS.

3. Detection of Antibody VP101

The purified sample was added to both a reduced protein electrophoresis loading buffer and a non-reduced protein electrophoresis loading buffer, and then boiled for SDS-PAGE electrophoresis detection. The electropherogram of VP101 is shown in FIG. 1. The target protein of the reduced protein sample is at 75 kD and 25 kD, and the target protein of the non-reduced protein sample (single antibody) is at 200 kD.

Unless otherwise specified, the humanized antibody VP101 used in the following experiments was prepared by the method of this example.

Example 2: Detection of Kinetic Parameters of Humanized Antibody VP101

1. Detection of Kinetic Parameters of the Binding of Humanized Antibody VP101 to PD-1-mFc The sample dilution buffer was PBS (0.02% Tween-20, 0.1% BSA, pH7.4). 5 μg/mL antibody was immobilized to an AHC sensor with the immobilization height being about 0.4 nM. The sensor was equilibrated in a buffer for 60 s, and the antibody immobilized to the sensor bound to PD-1-mFc at a concentration of 0.62-50 nM (three-fold gradient dilution) for 120 s, and then the antigen and antibody dissociated in the buffer for 300 s. The data were analyzed by 1:1 model fitting to obtain affinity constants. The data acquisition software was Fortebio Data Acquisition 7.0, and the data analysis software was Fortebio Data Analysis 7.0. Kinetic parameters of the binding of antibodies VP101, BsAbB7, BsAbB8, 14C12H1L1 and the control antibody nivolumab to PD-1-mFc are shown in Table 2, and the detection results of the kinetic characteristic parameters are shown in FIG. 2, FIG. 3, FIG. 4, FIG. 5 and FIG. 6, respectively.

TABLE 2

Kinetic parameters of the binding of humanized antibody VP101, BsAbB7, BsAbB8, 14C12H1L1 and the control antibody nivolumab to PD-1-mFc

| Sample ID | $K_D$ (M) | Kon (1/Ms) | S E (kon) | Kdis (1/s) | S E (kdis) | Rmax (nm) |
|---|---|---|---|---|---|---|
| VP101 | 1.68E−10 | 3.22E+05 | 1.44E+04 | 5.40E−05 | 3.16E−05 | 0.14-0.28 |
| BsAbB7 | 1.62E−10 | 3.27E+05 | 2.60E+04 | 5.30E−05 | 6.24E−05 | 0.01-0.11 |
| BsAbB8 | 4.06E−10 | 3.39E+05 | 2.04E+04 | 1.37E−04 | 4.61E−05 | 0.01-0.13 |
| 14C12H1L1 | 1.64E−10 | 4.55E+05 | 1.61E+04 | 7.47E−05 | 2.98E−05 | 0.24-0.28 |
| Nivolumab | 2.32E−10 | 5.85E+05 | 2.03E+04 | 1.36E−04 | 3.47E−05 | 0.02-0.14 |

$K_D$ is affinity constant; kon is binding rate of antigen and antibody; kdis is dissociation rate of antigen and antibody; KD = kdis/kon.

The results show that the antibodies VP101 and BsAbB7 are equivalent in terms of affinity for PD-1-mFc; the affinity constant of VP101 for PD-1-mFc is significantly smaller than that of BsAbB8, suggesting that VP101 has better binding activity; the dissociation rate constant for VP101 and PD-1-mFc was significantly smaller than BsAbB8 and 14C12H1L1, suggesting that VP101 binds to antigen more stably with a dissociation rate slower than that of 14C12H1L1 and BsAbB8.

2. Detection of Kinetic Parameters of the Binding of Humanized Antibody VP101 to VEGF-his The sample dilution buffer was PBS (0.02% Tween-20, 0.1% BSA, pH7.4). 1 μg/mL VEGF-His was immobilized to the HIS1K sensor for 20 s, then the sensor was equilibrated in a buffer for 60 s, and the VEGF immobilized on the sensor bound to the antibody at a concentration of 12.34-1000 nM (three-fold gradient dilution) for 120 s, and then the antigen and antibody dissociated in the buffer for 300 s. The data were analyzed by 1:1 model fitting to obtain affinity constants. The data acquisition software was Fortebio Data Acquisition 7.0, and the data analysis software was Fortebio Data Analysis 7.0.

Kinetic parameters of the binding of antibodies VP101, BsAbB7, BsAbB8 and the control antibody bevacizumab to VEGF-His are shown in Table 3, and the detection results of kinetic characteristic parameters are shown in FIG. 7, FIG. 8, FIG. 9 and FIG. 10 respectively.

TABLE 3

Kinetic parameters of the binding of antibodies VP101, BsAbB7, BsAbB8 and the control antibody bevacizumab to VEGF-His

| Sample ID | $K_D$ (M) | Kon (1/Ms) | S E (kon) | Kdis (1/s) | S E (kdis) | Rmax (nm) |
|---|---|---|---|---|---|---|
| VP101 | 5.21E−10 | 1.55E+05 | 9.67E+03 | 8.05E−05 | 4.66E−05 | 0.39-0.60 |
| BsAbB7 | 5.14E−10 | 1.57E+05 | 9.67E+03 | 8.05E−05 | 4.83E−05 | 0.36-0.53 |
| BsAbB8 | 6.33E−10 | 1.71E+05 | 1.07E+04 | 1.08E−04 | 4.64E−05 | 0.39-0.56 |
| Bevacizumab | 7.24E−10 | 1.23E+05 | 7.09E+03 | 8.90E−05 | 4.53E−05 | 0.29-0.41 |

The results show that the antibodies VP101 and BsAbB7 are equivalent in terms of affinity for the antigen, and the affinity constant of VP101 is significantly smaller than that of BsAbB8 and the control antibody bevacizumab, suggesting that VP101 has better binding activity; the dissociation rate constant of VP101 for VEGF-His is significantly smaller than that of BsAbB8, suggesting that VP101 binds to antigen more stably with a slower dissociation rate than that of BsAbB8.

Example 3: Detection of Binding Activity of Antibody VP101 to Antigen by ELISA

1. Detection of Binding Activity of Antibody VP101 to Antigen VEGFA-his by Indirect ELISA The method is specified as follows:

The microplate was coated with VEGFA-His and incubated at 37° C. for 2 hours. After being washed, the microplate was blocked with 1% BSA for 2 hours. After being washed, the microplate was added with the gradiently diluted antibody and incubated at 37° C. for 30 minutes. After being washed, the microplate was added with the enzyme-labeled goat anti-human IgG secondary antibody working solution and incubated for 30 minutes at 37° C. After being washed, the microplate was added with TMB chromogenic solution for color developing for 5 minutes in the absence of light, and then stop solution was added to terminate the chromogenic reaction. Then the microplate was put into a microplate reader immediately, and the OD value of each well in the microplate was read at 450 nm. SoftMax Pro 6.2.1 was used to analyze and process the data.

Figure 11:
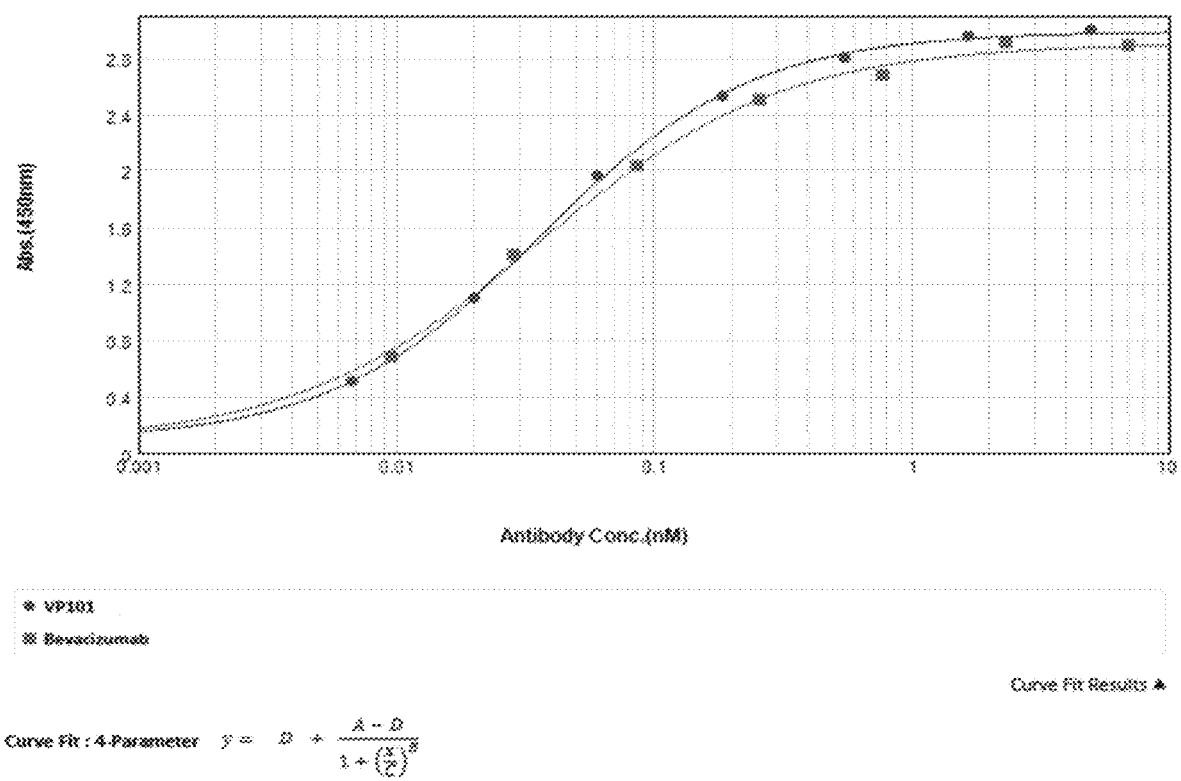
FIG. 11 shows the binding activity of antibody VP101 to VEGFA detected by indirect ELISA.

The detection result of the binding of antibody VP101 to antigen VEGFA-His is shown in FIG. 11. The absorbance intensities at each dose are shown in Table 4. The binding $EC_{50}$ of antibody was calculated by curve fitting using antibody concentration as the abscissa and absorbance value as the ordinate, and the results are shown in Table 4 below.

TABLE 4

Binding of bifunctional antibody to VEGFA-his (Indirect ELISA)

| Antibody concentration (μg/mL) | Coating: VEGFA-His (1 μg/mL) | | | |
|---|---|---|---|---|
| | VP101 | | Bevacizumab | |
| 1.0000 | 3.045 | 2.943 | 2.798 | 2.974 |
| 0.3333 | 3.037 | 2.861 | 2.816 | 2.993 |
| 0.1111 | 2.901 | 2.689 | 2.653 | 2.700 |
| 0.0370 | 2.597 | 2.460 | 2.445 | 2.555 |
| 0.0123 | 2.013 | 1.914 | 1.998 | 2.074 |
| 0.0041 | 1.115 | 1.086 | 1.446 | 1.363 |
| 0.0014 | 0.524 | 0.496 | 0.640 | 0.729 |
| 0.0000 | 0.099 | 0.091 | 0.094 | 0.083 |
| Secondary antibody | Goat anti-human IgG (H + L), HRP (1:5000) | | | |
| $EC_{50}$ (nM) | 0.036 | | 0.035 | |

The results show that antibody VP101 is able to bind to VEGFA protein efficiently and its binding efficiency is dose-dependent, and the two antibodies are equivalent in terms of binding activity to human VEGFA.

2. Detection of Respective Binding Activities of Antibodies VP101, BsAbB7 and BsAbB8 to Antigen VEGFA-his by Indirect ELISA The method is specified as follows:

The microplate was coated with VEGFA-His and incubated overnight at 4° C. After being washed, the microplate was blocked with 1% BSA (dissolved in PBS) for 2 hours. After being washed, the microplate was added with the gradiently diluted antibody and incubated at 37° C. for 30 minutes. After being washed, the microplate was added with the horseradish peroxidase-labeled goat anti-human IgG Fc (Jackson, 109-035-098) working solution and incubated for 30 minutes at 37° C. After being washed, the microplate was added with TMB (Neogen, 308177) for color developing for 5 minutes in the absence of light, and then stop solution was added to terminate the chromogenic reaction. Then the microplate was put into a microplate reader immediately, and the OD value of each well in the microplate was read at 450 nm. SoftMax Pro 6.2.1 was used to analyze and process the data.

Figure 12:
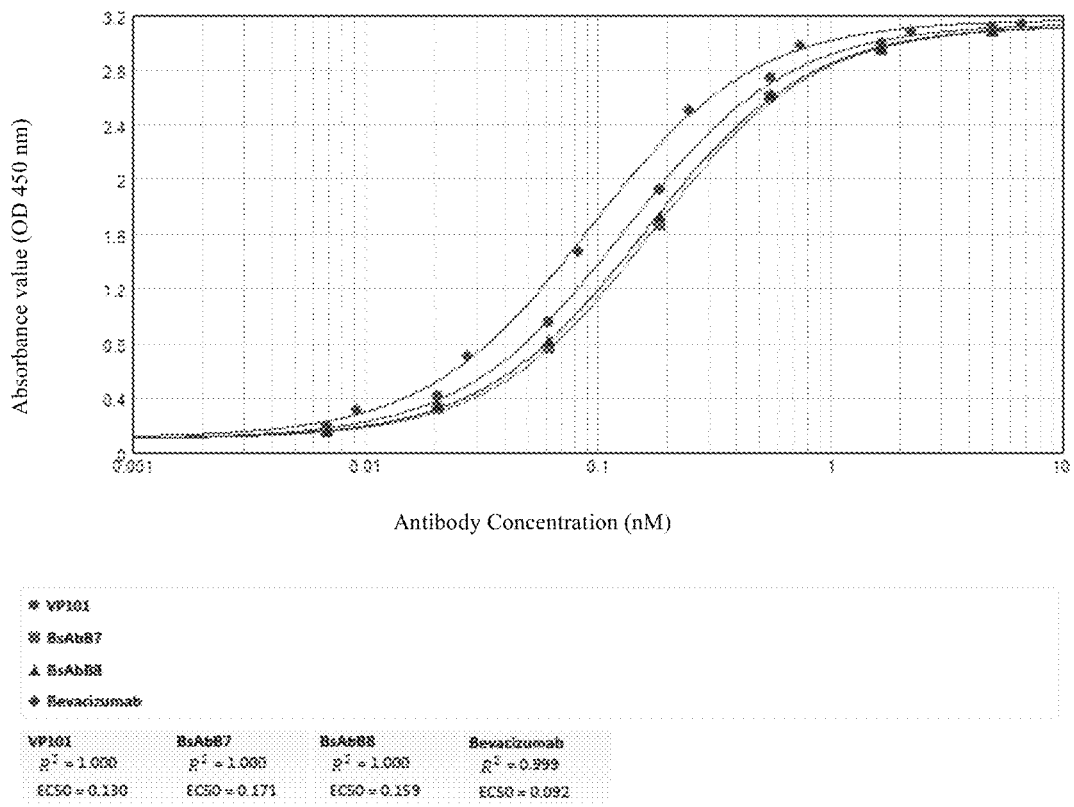
FIG. 12 shows the respective binding activities of antibodies VP101, BsAbB7, BsAbB8 and bevacizumab to VEGFA-his detected by indirect ELISA.

The result of the binding of antibody VP101 to antigen VEGFA-His is shown in FIG. 12. The absorbance intensities at each dose are shown in Table 5. The binding $EC_{50}$ of antibody was calculated by curve fitting using antibody concentration as the abscissa and absorbance value as the ordinate, and the results are shown in Table 5 below.

TABLE 5

Respective binding activities of VP101, BsAbB7, BsAbB8 and bevacizumab to VEGFA-His (Indirect ELISA)

| Antibody concentration | Antibody coating: VEGFA-His 1 µg/mL | | | | | | | |
|---|---|---|---|---|---|---|---|---|
| (µg/mL) | VP101 | | BsAbB7 | | BsAbB8 | | Bevacizumab | |
| 1.000 | 3.112 | 3.090 | 3.074 | 3.081 | 3.070 | 3.093 | 3.137 | 3.138 |
| 0.333 | 3.026 | 2.961 | 2.954 | 2.941 | 2.946 | 2.968 | 3.075 | 3.086 |
| 0.111 | 2.802 | 2.684 | 2.575 | 2.621 | 2.631 | 2.618 | 2.965 | 2.999 |
| 0.037 | 1.972 | 1.876 | 1.656 | 1.668 | 1.756 | 1.709 | 2.504 | 2.503 |
| 0.012 | 0.994 | 0.915 | 0.754 | 0.764 | 0.809 | 0.814 | 1.476 | 1.454 |
| 0.004 | 0.436 | 0.391 | 0.317 | 0.332 | 0.347 | 0.339 | 0.711 | 0.700 |
| 0.001 | 0.197 | 0.177 | 0.151 | 0.155 | 0.159 | 0.155 | 0.318 | 0.311 |
| 0 | 0.083 | 0.063 | 0.086 | 0.076 | 0.095 | 0.072 | 0.066 | 0.064 |
| Secondary antibody | Horseradish peroxidase-labeled goat anti-human IgG Fc, HRP (1:5000) | | | | | | | |
| $EC_{50}$(nM) | 0.130 | | 0.171 | | 0.159 | | 0.092 | |

The results show that the antibodies VP101, BsAbB7, BsAbB8 and bevacizumab all can bind to the VEGF protein efficiently and their binding efficiency is dose-dependent, and antibody VP101 has a higher binding activity to human VEGF than BsAbB7 and BsAbB8.

3. Detection of Binding Activity of Antibody VP101 to Antigen PD-1 by Indirect ELISA The method is specified as follows:

The microplate was coated with human PD-1-mFc and incubated overnight at 4° C. After being blocked with 1% BSA at 37° C. for 2 hours, the microplate was added with antibody, and then incubated at 37° C. for 30 minutes. After the microplate was washed and patted dry, the HRP-labeled goat anti-human IgG (H+L) secondary antibody (Jackson, 109-035-088) was added, and the microplate was incubated at 37° C. for 30 minutes. After the microplate was washed and patted dry, TMB (Neogen, 308177) was added for color developing for 5 minutes, and then stop solution was added to terminate the color development. Then the microplate was put into a microplate reader immediately, and the OD value of each well in the microplate was read at 450 nm. SoftMax Pro 6.2.1 was used to analyze and process the data.

Figure 13:
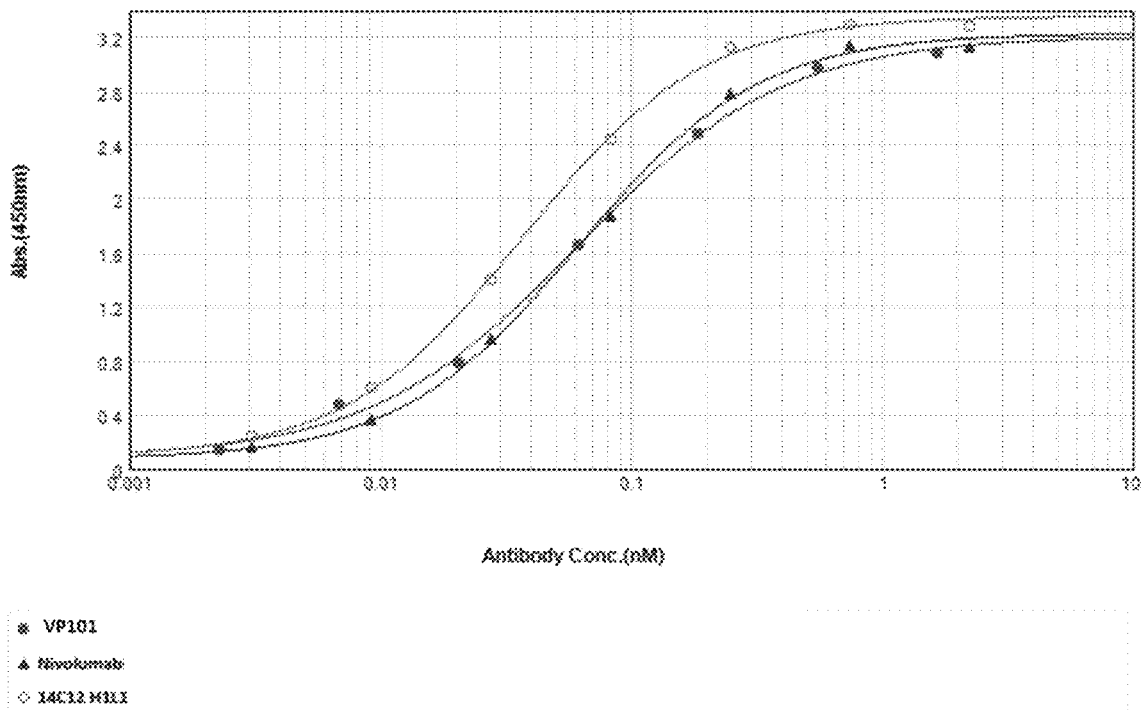
FIG. 13 shows the binding activity of antibody VP101 to PD-1 detected by indirect ELISA.

The detection result of the binding of antibody VP101 to antigen PD-1 is shown in FIG. 13. The absorbance intensities at each dose are shown in Table 6. By quantitative analysis of the bound antibody VP101, the curve simulation was performed to obtain the binding efficiency $EC_{50}$ of the antibody, which is shown in Table 6 below.

TABLE 6

Binding of bifunctional antibody to PD-1 (Indirect ELISA)

| Antibody dilution | Antibody coating: PD-1-mFc 0.5 µg/mL | | | | | |
|---|---|---|---|---|---|---|
| gradient | VP101 | | Nivolumab | | 14C12H1L1 | |
| 0.333 µg/ml | 3.109 | 3.063 | 3.137 | 3.130 | 3.298 | 3.278 |
| 1:3 | 3.016 | 2.926 | 3.139 | 3.140 | 3.245 | 3.352 |
| 1:9 | 2.461 | 2.513 | 2.802 | 2.758 | 3.104 | 3.155 |
| 1:27 | 1.638 | 1.675 | 1.949 | 1.810 | 2.352 | 2.549 |
| 1:81 | 0.787 | 0.791 | 0.933 | 0.990 | 1.382 | 1.421 |
| 1:243 | 0.301 | 0.656 | 0.348 | 0.375 | 0.612 | 0.596 |
| 1:729 | 0.136 | 0.145 | 0.159 | 0.162 | 0.253 | 0.247 |
| 0 | 0.068 | 0.056 | 0.053 | 0.053 | 0.053 | 0.053 |
| $EC_{50}$(nM) | 0.06 | | 0.061 | | 0.037 | |

The results show that antibody VP101 is able to bind to PD-1 protein efficiently and its binding efficiency is dose-dependent.

4. Detection of Respective Binding Activities of Antibodies VP101, BsAbB7 and BsAbB8 to Antigen PD-1 by Indirect ELISA The method is specified as follows:

The microplate was coated with human PD-1-mFc and incubated overnight at 4° C. After being blocked with 1% BSA at 37° C. for 2 hours, the microplate was added with antibody, and then incubated at 37° C. for 30 minutes. After the microplate was washed and patted dry, the horseradish peroxidase-labeled goat anti-human IgG Fc (Jackson, 109-035-098) was added, and the microplate was incubated at 37° C. for 30 minutes. After the microplate was washed and patted dry, TMB (Neogen, 308177) was added for color developing for 5 minutes, and then stop solution was added to terminate the color development. Then the microplate was put into a microplate reader immediately, and the OD value of each well in the microplate was read at 450 nm. SoftMax Pro 6.2.1 was used to analyze and process the data.

Figure 14:
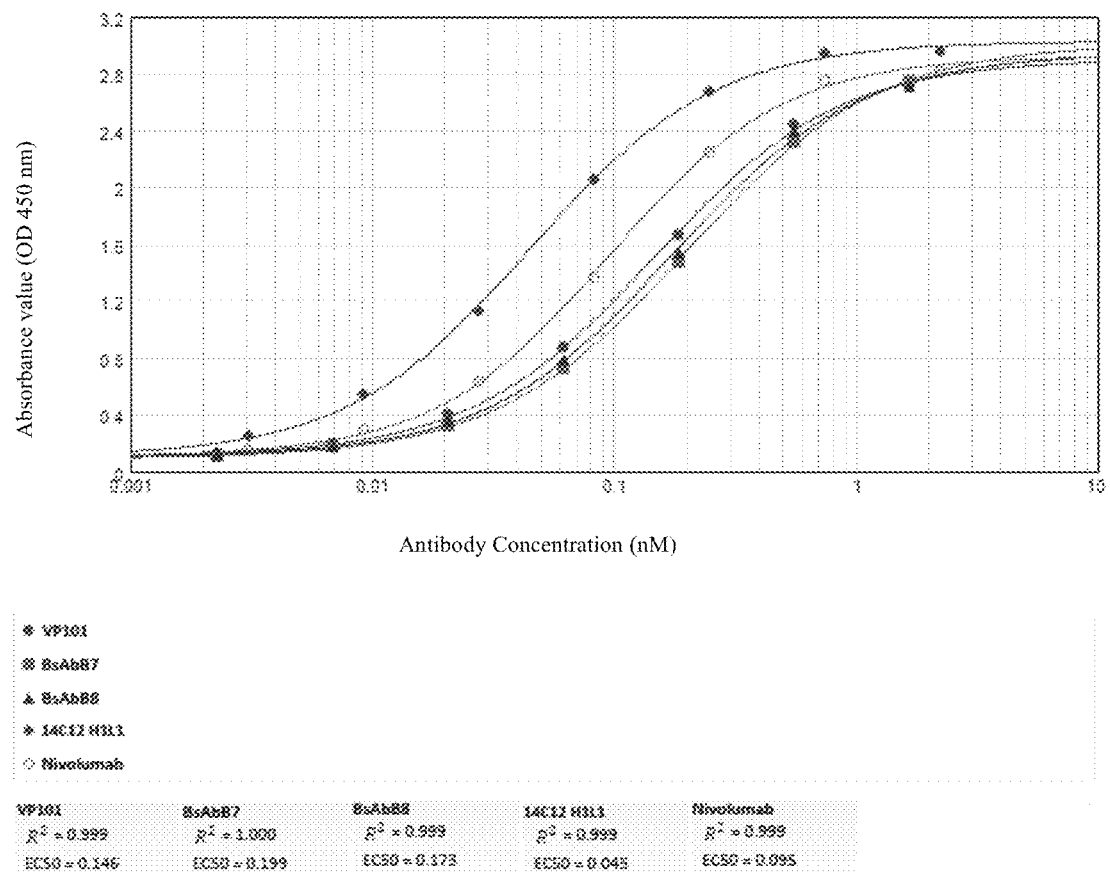
FIG. 14 shows the respective binding activities of antibodies VP101, BsAbB7, BsAbB8, 14C12H1L1 and nivolumab to PD-1 detected by indirect ELISA.

The detection result of the binding of antibody VP101 to antigen PD-1 is shown in FIG. 14. The absorbance intensities at each dose are shown in Table 7. By quantitative analysis of the bound antibody VP101, the curve simulation was performed to give the binding efficiency $EC_{50}$ of the antibody, which is shown in Table 7 below.

TABLE 7

Respective binding activities of antibodies VP101, BsAbB7, BsAbB8, 14C12H1L1 and nivolumab to PD-1 (Indirect ELISA)

| Antibody concentration | Antigen coating: PD-1-mFc 0.5 µg/mL | | | | | | | | | |
|---|---|---|---|---|---|---|---|---|---|---|
| (µg/mL) | VP101 | | BsAbB7 | | BsAbB8 | | 14C12 H1L1 | | Nivolumab | |
| 0.333 | 2.717 | 2.709 | 2.732 | 2.755 | 2.716 | 2.715 | 2.947 | 2.966 | 2.823 | 2.824 |
| 0.111 | 2.507 | 2.381 | 2.318 | 2.321 | 2.377 | 2.409 | 2.923 | 2.967 | 2.747 | 2.758 |
| 0.037 | 1.709 | 1.616 | 1.491 | 1.457 | 1.522 | 1.549 | 2.656 | 2.694 | 2.208 | 2.293 |
| 0.012 | 0.916 | 0.822 | 0.732 | 0.711 | 0.797 | 0.775 | 2.049 | 2.060 | 1.348 | 1.389 |
| 0.004 | 0.413 | 0.394 | 0.333 | 0.321 | 0.368 | 0.351 | 1.139 | 1.132 | 0.629 | 0.638 |
| 0.001 | 0.195 | 0.191 | 0.167 | 0.174 | 0.181 | 0.174 | 0.552 | 0.541 | 0.295 | 0.295 |
| 0.000 | 0.140 | 0.123 | 0.110 | 0.103 | 0.117 | 0.118 | 0.254 | 0.248 | 0.152 | 0.157 |
| 0.000 | 0.099 | 0.095 | 0.089 | 0.074 | 0.100 | 0.081 | 0.083 | 0.075 | 0.078 | 0.084 |
| Secondary antibody | Horseradish peroxidase-labeled goat anti-human IgG Fc, HRP (1:5000) | | | | | | | | | |
| $EC_{50}$(nM) | 0.146 | | 0.199 | | 0.173 | | 0.045 | | 0.095 | |

The results show that the antibody VP101 can bind to the PD-1 protein efficiently and its binding efficiency is dose-dependent, and antibody VP101 has a higher binding activity to human PD-1 than BsAbB7 and BsAbB8.

5. Detection of Activity of Antibody VP101 in Competing with VEGFR2 for Binding to Antigen VEGFA by Competitive ELISA The method is specifically as follows:

The microplate was coated with VEGF-His and incubated at 37° C. for 2 hours. After being washed, the microplate was blocked with 1% BSA for 1 hour at 37° C. After being washed, the microplate was added with the gradiently diluted antibodies and human VEGFR2 ECD-mFc-bio (final concentration: 0.02 µg/mL) and incubated at room temperature for 2 hours. After being washed, the microplate was added with HRP-labeled streptavidin SA-HRP (1:4000) working solution and incubated at 37° C. for 30 minutes. After being washed, the microplate was added with TMB chromogenic solution for color developing for 5 minutes in the absence of light, and then stop solution was added to terminate the chromogenic reaction. Then the microplate was put into a microplate reader immediately, and the OD value of each well in the microplate was read at 450 nm. SoftMax Pro 6.2.1 was used to analyze and process the data.

Figure 15:
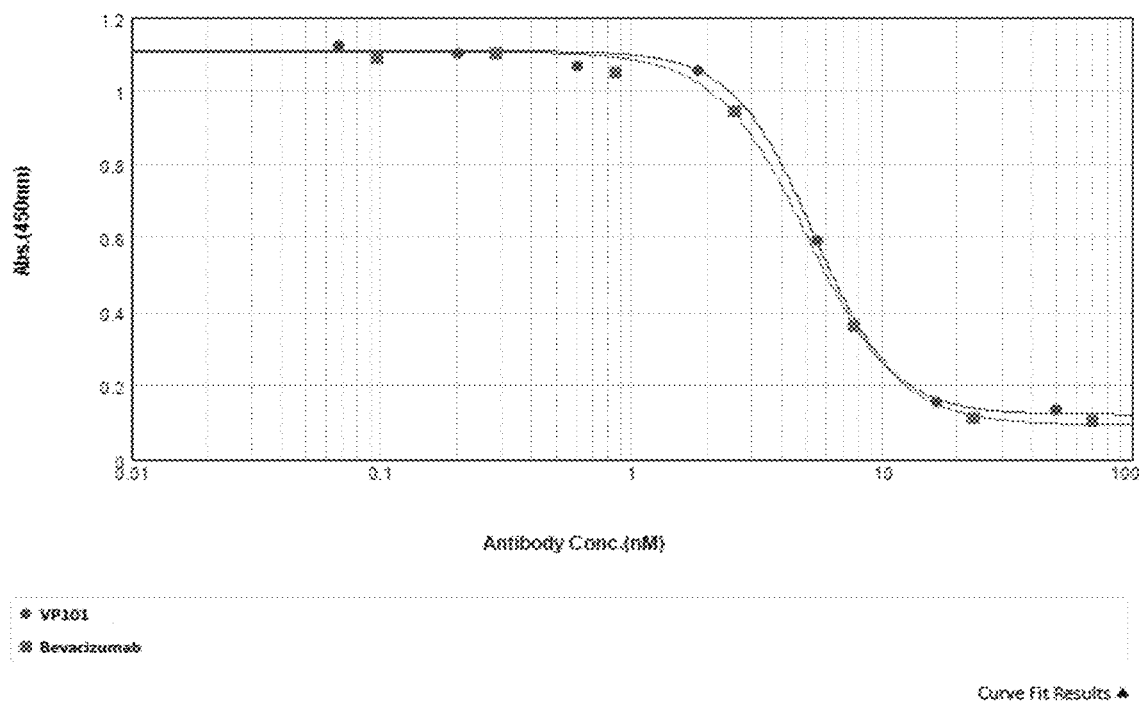
FIG. 15 shows the activity of antibody VP101 in competing with VEGFR2 for binding to VEGFA detected by competitive ELISA.

The detection results are shown in FIG. 15. The absorbance intensities at each dose are shown in Table 8. By quantitative analysis of the absorbance intensities of the bound antibodies, the curve simulation was performed to give the binding efficiency $EC_{50}$ of the antibodies (Table 8).

TABLE 8

Detection of antibody in competing with VEGFR2-mFc for binding to the antigen VEGFA-His by competitive ELISA
Coating: VEGF-His (2 µg/mL)

| Antibody concentration (µg/mL) | VP101 | | Bevacizumab | |
|---|---|---|---|---|
| 10.000 | 0.133 | 0.133 | 0.103 | 0.104 |
| 3.333 | 0.161 | 0.149 | 0.114 | 0.109 |
| 1.111 | 0.624 | 0.563 | 0.374 | 0.351 |
| 0.370 | 1.055 | 1.051 | 0.905 | 0.982 |
| 0.123 | 1.059 | 1.075 | 0.964 | 1.049 |
| 0.041 | 1.137 | 1.068 | 1.062 | 1.141 |
| 0.014 | 1.106 | 1.138 | 1.010 | 1.169 |
| 0.000 | 1.155 | 1.131 | 1.173 | 1.153 |
| Receptor | VEGFR2 ECD-mFc-bio, 0.02 µg/ml | | | |
| Secondary antibody | SA-HRP (1:4000) | | | |
| $EC_{50}$ (nM) | 5.324 | | 5.086 | |

The results show that the antibody VP101 can effectively bind to the antigen VEGFA and inhibit the binding of VEGFR2 to VEGFA, and its efficiency in inhibiting the binding of VEGFR2 to VEGFA is dose-dependent.

6. Detection of Antibody VP101 in Competing with PD-L1 for Binding to Antigen PD-1 by Competitive ELISA The method is specifically as follows:

The microplate was coated with PD-1-hFc and incubated overnight at 4° C. After the microplate was blocked with 1% BSA for 2 hours, antibodies at different concentrations were each mixed with PD-L1-hFc for 10 minutes (see Table 10 for the dilution concentrations). After incubation at 37° C. for 30 minutes, the microplate was washed and patted dry. Then enzyme-labeled secondary antibody was added, and the microplate was incubated at 37° C. for 30 minutes. After the microplate was washed and patted dry, TMB was added for color developing for 5 minutes, and then stop solution was added to terminate the color development. Then the microplate was put into a microplate reader immediately, and the OD value of each well in the microplate was read at 450 nm (see Table 10). SoftMax Pro 6.2.1 was used to analyze and process the data.

Figure 16:
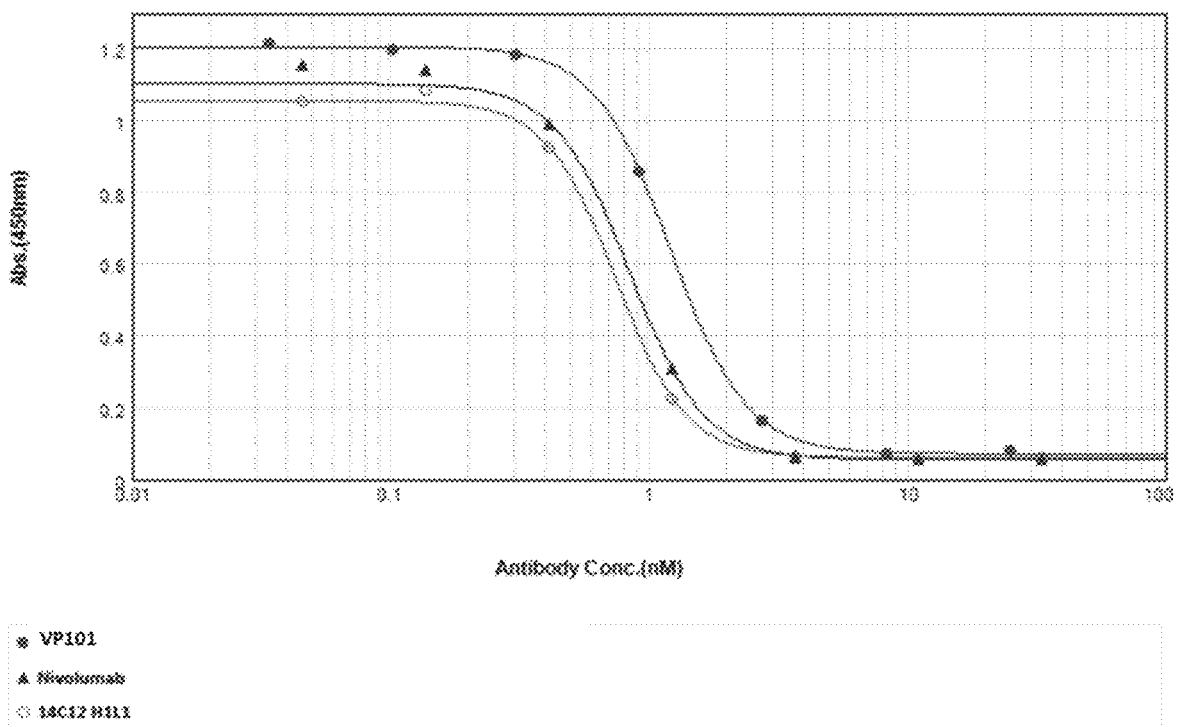
FIG. 16 shows the activity of antibody VP101 in competing with PD-L1 for binding to PD-1 detected by competitive ELISA.

The detection results are shown in FIG. 16. The absorbance intensities at each dose are shown in Table 9. By quantitative analysis of the bound antibody VP101, the curve simulation was performed to give the binding efficiency $EC_{50}$ of the antibody (Table 9).

TABLE 9

Detection of bifunctional antibody competing with PD-L1 for binding to PD-1 by competitive ELISA

| Antibody dilution gradient | Antigen coating: PD-1-hFc 0.5 µg/mL | | | | | |
|---|---|---|---|---|---|---|
| | VP101 | | Nivolumab | | 14C12H1L1 | |
| 5 µg/ml | 0.096 | 0.063 | 0.058 | 0.058 | 0.062 | 0.063 |
| 1:3 | 0.064 | 0.077 | 0.059 | 0.059 | 0.061 | 0.064 |
| 1:9 | 0.166 | 0.160 | 0.061 | 0.062 | 0.066 | 0.071 |
| 1:27 | 0.867 | 0.848 | 0.284 | 0.335 | 0.262 | 0.193 |
| 1:81 | 1.217 | 1.149 | 0.973 | 1.007 | 0.968 | 0.882 |
| 1:243 | 1.196 | 1.949 | 1.139 | 1.144 | 1.122 | 1.051 |
| 1:729 | 1.183 | 1.250 | 1.127 | 1.185 | 1.052 | 1.059 |
| 0 | 1.153 | 1.276 | 0.960 | 1.071 | 1.027 | 1.024 |
| Receptor | PD-L1-mFc 0.3 µg/ml | | | | | |
| Secondary antibody | Goat anti-mouse IgG (H + L), HRP conjugated (1:5000) | | | | | |
| $EC_{50}$(nM) | 1.216 | | 0.842 | | 0.745 | |

The results show that antibody VP101 can effectively bind to antigen PD-1 and inhibit the binding of ligand PD-L1 to PD-1, and its efficiency in inhibiting the binding of PD-L1 to PD-1 is dose-dependent.

Example 4: Binding of Antibody VP101 to Cell Membrane Surface Antigen

Firstly, 293T cells expressing PD-1 antigen was constructed, and then the specific binding capacity of the antibody to the cell membrane surface antigen was analyzed and verified by flow cytometry.

1. Construction of 293T Cells Expressing PD-1 Antigen

The vector pLenti6.3-PD-1 of PD-1 (the vector pLenti6.3 was purchased from Invitrogen) was transfected into 293T cells, and clone group 293T-PD-1 cells which stably express PD-1 were obtained by screening.

2. Detection of Binding of Antibody to Cell Surface Antigen

The 293T-PD-1 expressing antigen obtained in the previous step was digested with pancreatin by a conventional pancreatin digestion method, and the number of cells in each collection tube was made to be 2×10⁵. Antibody diluting solutions with concentration gradiently diluted with PBSA (1% BSA) were each incubated with 293T-PD-1 cells on ice for 2 hours, and then each tube was added with 100 µL of FITC goat anti-human IgG (1:500) and incubated on ice for 1 hour. Then PBS was used for washing, and 300 µL of PBSA was used to resuspend the cells, and fluorescence signals (MFI) were detected with FITC channel on a flow cytometer.

Figure 17:
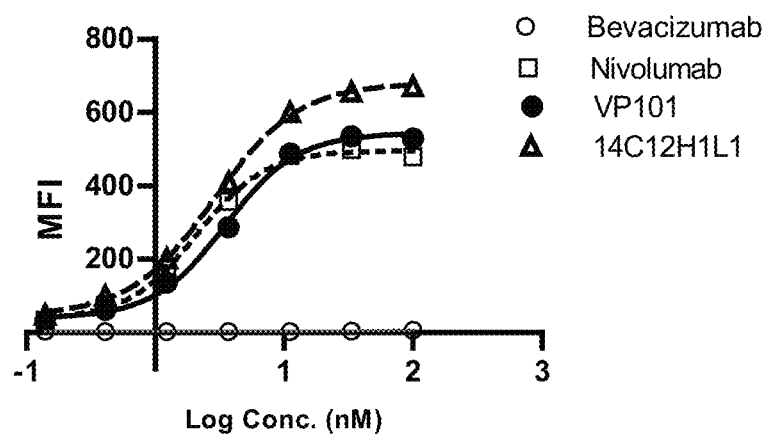
FIG. 17 shows the binding $EC_{50}$ of antibodies 14C12H1L1 and VP101 to 293T-PD-1 cell surface protein PD-1 detected by FACS.

The results are shown in FIG. 17, and the MFI values at each concentration are shown in Table 10. By fluorescence quantification analysis and curve fitting of the bound 14C12H1L1 antibody, the binding $EC_{50}$ of the VP101 antibody was calculated to be 3.5 nM.

TABLE 10

Analysis of fluorescence intensity of the binding of VP101 to 293T-PD-1 surface antigen detected by FACS

| Antibody (nM) | 0.14 | 0.41 | 1.23 | 3.70 | 11.11 | 33.33 | 100 | EC$_{50}$ |
|---|---|---|---|---|---|---|---|---|
| Bevacizumab | 3.2 | 2.2 | 2.0 | 2.3 | 2.7 | 3.8 | 5.7 | — |
| Nivolumab | 33.3 | 74.9 | 171.9 | 357.9 | 481.9 | 498.3 | 478.4 | 2.1 |
| 14C12H1L1 | 48.1 | 99.7 | 201.5 | 409.0 | 600.2 | 655.4 | 670.8 | 2.9 |
| VP101 | 30.8 | 61.8 | 135.7 | 286.9 | 487.7 | 534.0 | 528.6 | 3.5 |

The results show that the VP101 antibody can effectively bind to the PD-1 antigen on the 293T-PD-1 host cell surface, and its binding efficiency is dose-dependent, and bevacizumab has no binding activity to 293T-PD-1, which indicates that the binding of VP101 to 293T-PD-1 is specific.

3. The Binding of Antibodies VP101, BsAbB7 and BsAbB8 to the Cell Surface Antigen was Detected by Referring to the Experimental Procedure Described in Step 2 of this Example.

Figure 18:
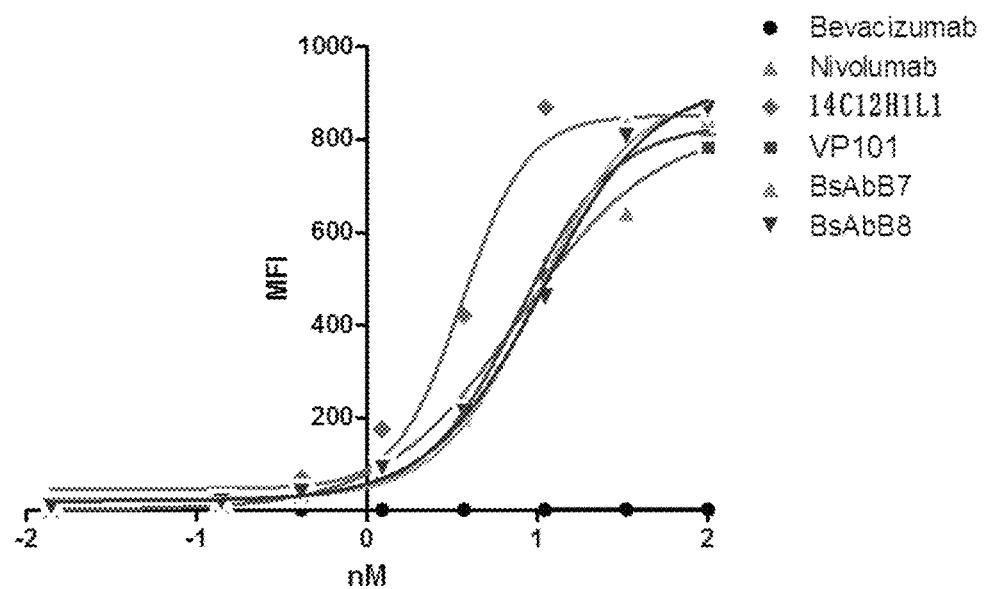
FIG. 18 shows the binding $EC_{50}$ of antibodies VP101, BsAbB7 and BsAbB8 to 293T-PD-1 cell surface protein PD-1 detected by FACS.

The results are shown in FIG. 18, and the MFI values at each concentration are shown in Table 11. By fluorescence quantification analysis and curve fitting of the bound antibody, the binding EC$_{50}$ values of nivolumab, 14C12H1L1, VP101, BsAbB7 and BsAbB8 were calculated to be 7.853 nM, 3.607 nM, 7.896 nM, 9.943 nM and 10.610 nM, respectively.

TABLE 11

Analysis of fluorescence intensities of the binding of VP101, BsAbB7 and BsAbB8 to 293T-PD-1 surface antigen detected by FACS

| Antibody (nM) | 0.014 | 0.14 | 0.41 | 1.23 | 3.7 | 11 | 30 | 100 | EC50(nM) |
|---|---|---|---|---|---|---|---|---|---|
| Bevacizumab | 1.89 | 1.90 | 2.20 | 1.92 | 2.04 | 2.48 | 2.80 | 2.43 | — |
| Nivolumab | 3.91 | 15.30 | 34.69 | 94.04 | 234.34 | 533.63 | 640.15 | 804.69 | 7.853 |
| 14C12H1L1 | 7.40 | 29.55 | 69.16 | 175.54 | 422.53 | 868.45 | 831.27 | 813.58 | 3.607 |
| VP101 | 3.47 | 16.16 | 38.75 | 93.08 | 216.76 | 509.23 | 810.37 | 783.58 | 7.896 |
| BsAbB7 | 3.85 | 14.86 | 37.45 | 83.78 | 202.40 | 465.10 | 837.61 | 846.80 | 9.943 |
| BsAbB8 | 4.41 | 16.77 | 36.86 | 89.89 | 210.40 | 457.91 | 804.43 | 863.35 | 10.610 |

The results show that the VP101 antibody can bind to the membrane surface PD-1 of 293T-PD1 in a dose-dependent manner. Bevacizumab has no binding activity to 293T-PD-1, which indicates that the binding of VP101 to 293T-PD-1 is specific.

Example 5; Competitive Binding of Antibody VP101 to Cell Membrane Surface Antigen 1. A competitive flow cytometry method was adopted to detect the EC$_{50}$ of the VP101 in competing with PD-L1 for binding to the cell membrane surface antigen PD-1, and the method is specified as follows:

The 293T-PD-1 cells was digested in a conventional way, and divided into several samples with 300,000 cells for each, which were then subjected to centrifugation and washing. Then each tube was added with 100 μL of corresponding gradiently diluted antibody and incubated on ice for 30 minutes; 100 μL of PD-L1-mFc was then added to each tube, and the mixture was mixed well to reach a final concentration of 20 nM, and then incubated on ice for 1 hour. Then 500 μL of 1% PBSA was added, and the mixture was centrifuged at 5600 rpm for 5 minutes to remove the supernatant. 100 μL of FITC coat anti mouse antibody diluted at a ratio of 1:500 was then added into each tube, and the mixture was incubated on ice for 40 minutes in the absence of light after being mixed well. Then the mixture was centrifuged, washed and resuspended, and then transferred to a loading tube for testing.

Figure 19:
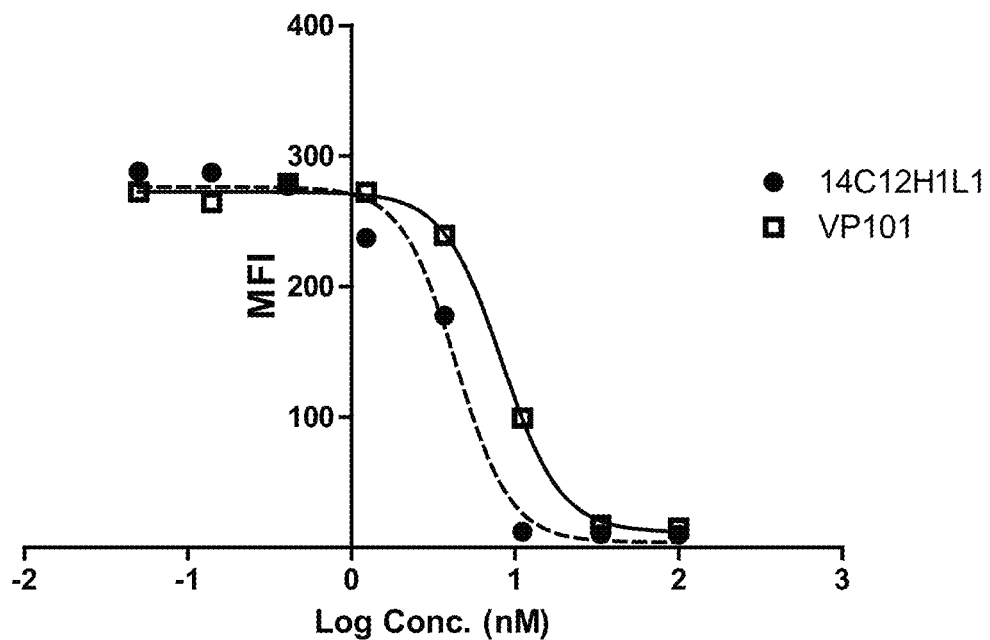
FIG. 19 shows the activity of antibodies VP101 and 14C12H1L1 in competing with PD-L1 for binding to 293T-PD-1 cell surface protein PD-1 detected by FACS.

The results are shown in FIG. 19, and the MFI values at each concentration are shown in Table 12. By fluorescence quantification analysis and curve fitting, the binding EC$_{50}$ values of the antibodies VP101 and 14C12H1L1 were calculated to be 8.33 nM and 4.37 nM, respectively.

TABLE 12

Analysis of fluorescence intensities of 14C12H1L1 and VP101 in competing for binding to 293T-PD-1 surface antigen detected by FACS

| Antibody (nM) | 0.05 | 0.14 | 0.41 | 1.23 | 3.70 | 11.11 | 33.33 | 100.00 | EC$_{50}$ | R$^2$ |
|---|---|---|---|---|---|---|---|---|---|---|
| 14C12H1L1 | 288.17 | 287.29 | 277.09 | 237.22 | 177.80 | 12.04 | 10.32 | 9.87 | 4.37 | 0.988 |
| VP101 | 272.66 | 264.39 | 279.11 | 272.26 | 239.18 | 99.29 | 17.05 | 14.91 | 8.33 | 0.999 |

The results show that the VP101 antibody can effectively block the binding of PDL-1 to PD-1 on the surface of 293T-PD-1 host cells in a dose-dependent manner.

2. $EC_{50}$ values of VP101, BsAbB7, BsAbB8, 14C12H1L1 and nivolumab in competing with PD-L1 for binding to the cell membrane surface antigen PD-1 were detected by using competitive flow cytometry and referring to the experimental procedure described in step 1 of this example.

Figure 20:
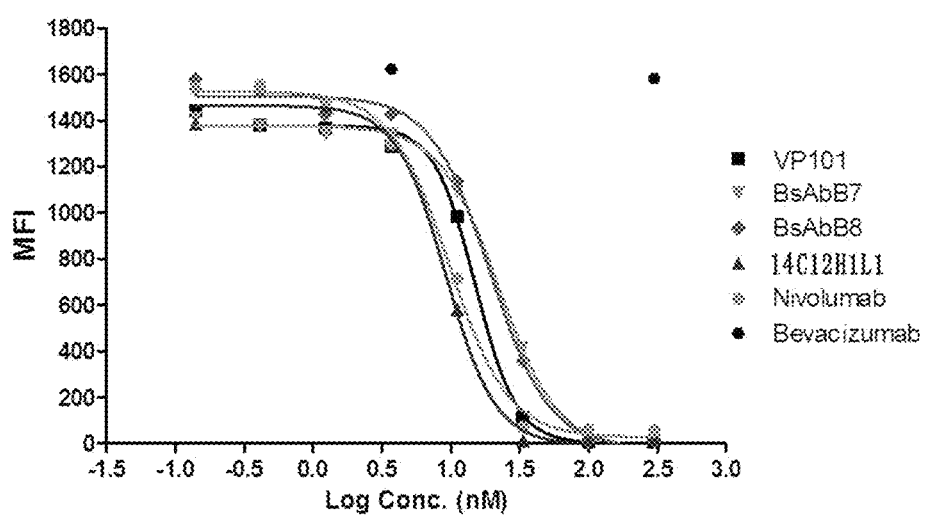
FIG. 20 shows the activity of antibodies 14C12H1L1, VP101, BsAbB7, BsAbB8, 14C12H1L and nivolumab in competing with PD-L1 for binding to 293T-PD-1 cell surface protein PD-1 detected by FACS.

The results are shown in FIG. 20, and the MFI values at each concentration are shown in Table 13. By fluorescence quantification analysis and curve fitting, the competitive binding $EC_{50}$ values of antibodies VP101, BsAbB7, BsAbB8, 14C12H1L1 and nivolumab were calculated to be 15.04 nM, 22.25 nM, 19.25 nM, 9.21 nM and 9.72 nM, respectively.

Figure 21:
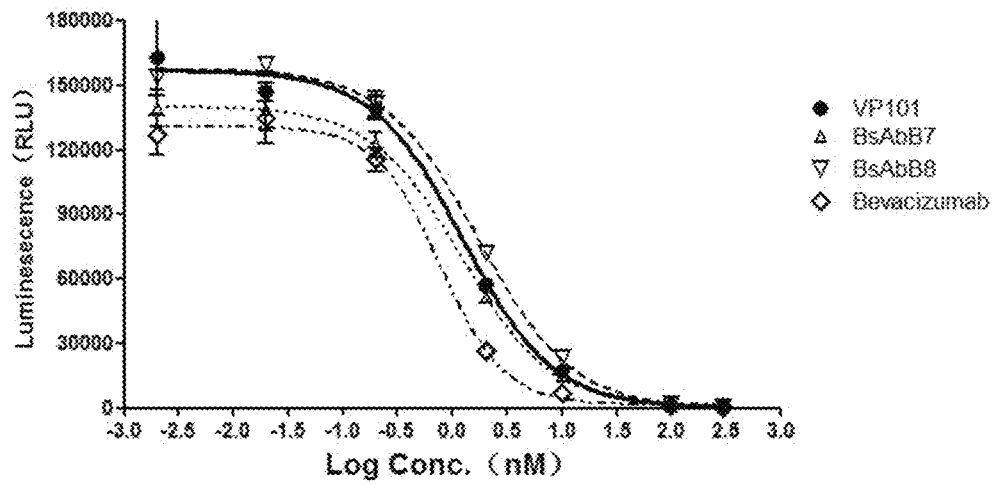
FIG. 21 shows the neutralization bioactivity of antibodies VP101, BsAbB7 and BsAbB8 in blocking VEGF to activate NFAT signaling pathway.

The experimental results are shown in FIG. 21, and the $EC_{50}$ values for each antibody are shown in Table 14.

TABLE 14

Detection of neutralization bioactivity of antibodies VP101, BsAbB7 and BsAbB8 in blocking VEGF to activate NFAT signaling pathway by reporter assay

| Sample | VP101 | BsAbB7 | BsAbB8 | Bevacizumab |
|---|---|---|---|---|
| $EC_{50}$ (nM) | 1.2400 | 1.2170 | 1.7280 | 0.7730 |

The results show that the $EC_{50}$ of VP101 is 1.240 nM, the $EC_{50}$ of BsAbB7 is 1.217 nM, the $EC_{50}$ of BsAbB8 is 1.728 nM, and the $EC_{50}$ of bevacizumab is 0.773 nM, and the

TABLE 13

Analysis of fluorescence intensities of VP101, BsAbB7, BsAbB8, 14C12H1L1 and nivolumab in competing for binding to 293T-PD-1 surface antigen detected by FACS

| Antibody (nM) | 0.14 | 0.41 | 1.23 | 3.7 | 11.11 | 33.33 | 100 | 300 | $EC_{50}$ | $R^2$ |
|---|---|---|---|---|---|---|---|---|---|---|
| VP101 | 1441.94 | 1380.62 | 1368.15 | 1288.34 | 982.69 | 112.90 | 8.49 | 8.21 | 15.04 | 0.9971 |
| BsAbB7 | 1412.62 | 1377.27 | 1339.60 | 1341.27 | 1094.35 | 417.70 | 9.23 | 9.18 | 22.25 | 0.9985 |
| BsAbB8 | 1578.36 | 1521.50 | 1427.20 | 1429.85 | 1137.74 | 359.69 | 9.73 | 9.68 | 19.25 | 0.9962 |
| 14C12H1L1 | 1384.08 | 1551.05 | 1462.85 | 1296.64 | 580.45 | 12.93 | 13.37 | 14.99 | 9.21 | 0.9950 |
| Nivolumab | 1539.58 | 1552.37 | 1483.84 | 1300.81 | 713.56 | 70.92 | 60.77 | 56.92 | 9.72 | 0.9969 |

The results show that the activity of the antibody 14C12H1L1 is equivalent to that of the marketed antibody nivolumab targeting PD-1, and is superior to that of the bifunctional antibody VP101. The activity of the antibody VP101 is superior that of to BsAbB7 and BsAbB8.

Example 6: Detection of Neutralization Bioactivity of Antibodies VP101, BsAbB7 and BsAbB8 in Blocking VEGF to Activate NFAT Signaling Pathway 1. Construction of 293T-NFAT-(opv)KDR(C7) Cells KDR (VEGFR2) vector pCDH-KDRFL(OPV)-GFP-Puro (Vector pCDH-GFP-Puro is purchased from Youbio) and NFAT vector pNFAT-luc-hygro (vector pGL4-luc2P-hygro is purchased from Promega) were transfected into 293T cells, and a clone group 293T-NFAT-(opv)KDR(C7) cells stably expressing KDR and NFAT luciferase reporter genes were obtained by screening.

2. 293T-NFAT-(opv)KDR(C7) cells were collected and centrifuged for 5 minutes to remove the supernatant; DMEM+10% FBS medium was used to resuspend the cells, and the cell number was counted and the cell viability was detected; then the cell concentration was adjusted to be in a proper range, and 50000 cells/50 μL cell suspension was added into each well of a black 96-well plate;

Corresponding antibodies (final concentrations being 300, 100, 10, 2, 0.2, 0.02, 0.002 nM) and VEGF (final concentration being 30 ng/mL) were diluted according to the experimental design, and the antibodies targeting VEGF were preincubated with VEGF for 1 hour at room temperature before being added into the cells. Blank and isotype controls (final volume of each well being 100 μL) were designed and incubated in a carbon dioxide incubator at 37° C., 5% $CO_2$ for 4 hours; 50 μL of Luciferase Assay System was added to each well, and Relative Fluorescence Units (RLUs) were detected by a multi-label microplate tester within 5 minutes.

experimental results show that the activity of VP101 and BsAbB7 in blocking VEGF to activate NFAT signaling pathway is better than that of BsAbB8.

Example 7: Experiment of VP101 Antibody Inhibiting VEGFA-Induced HUVEC Cell Proliferation HUVEC cells (purchased from Allcell) in a good growth state, after the cell concentration was adjusted to be 1.5× $10^4$/mL, were inoculated into a 96-well plate at 200 μL/well, and then incubated in an incubator at 37° C., 5% $CO_2$ for 24 hours. Then it was observed that the cells adhered well, and then culture medium was discarded. 20 nM VEGFA prepared by using 1640 containing 2% FBS was then added into the 96-well plate at 200 L/well, and antibodies at different concentrations were added, followed by incubation for 72 hours. 72 hours later, the culture medium was discarded and MTT was added. 4 hours later, the MTT was discarded and DMSO was added, and then a microplate reader was used to measure the OD value at 490 nm.

Figure 22:
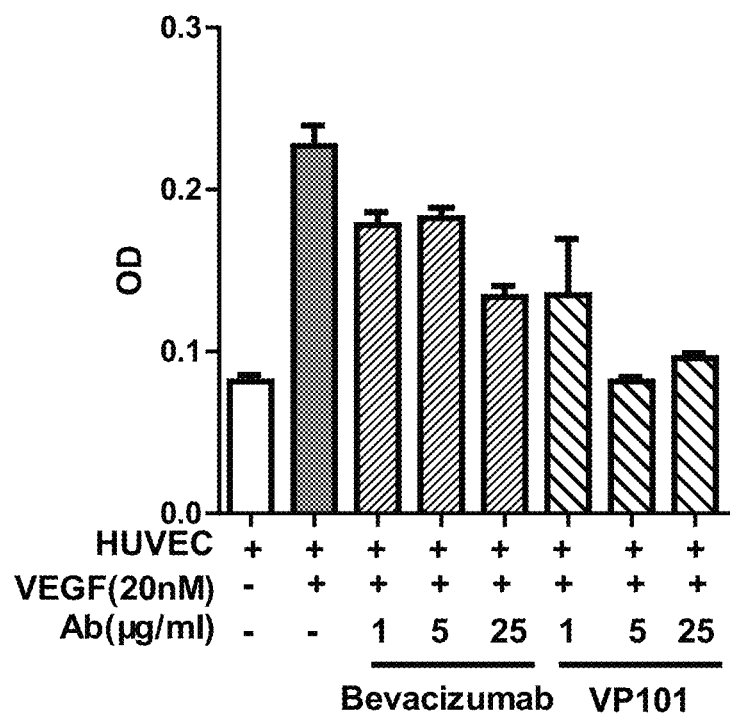
FIG. 22 shows the effect of bevacizumab and VP101 on HUVEC cell proliferation.

The results are shown in FIG. 22. The results show that the humanized antibodies VP101 and bevacizumab both can effectively inhibit VEGFA-induced HUVEC cell proliferation in a dose-dependent manner, and the pharmacological activity of VP101 in inhibiting VEGFA-induced HUVEC cell proliferation is higher than that of bevacizumab at the same dose.

Example 8: Promotion of Secretion of Cytokines IFN-γ and IL-2 in Mixed Lymphocyte Reaction 1. Promotion of Secretion of IFN-γ by VP101, 14C12H1L1 and Nivolumab in Mixed Culture System of DC and PBMC Cells PBMCs were isolated by Ficoll-Paque Plus (GE Healthcare) and added to IL-4 (Peprotech 200-04, 1000 U/mL) and GM-CSF (Peprotech 300-03, 1000 U/mL) for 6 days of induction, and then TNF-α (Peprotech 300-01A, 200 U/mL) was additionally added for 3 days of induction to obtain mature DC cells.

On the day of co-culture, fresh PBMCs were isolated from peripheral blood of another donor, and the obtained mature DC cells were mixed with the freshly isolated PBMCs of another donor at a ratio of 1:10, and meanwhile antibodies at different concentrations (hIgG as a control) were added. After co-culture for 5-6 days, cell supernatant was collected and assayed for IFN-γ content using an ELISA kit (purchased from Dakewe).

Figure 23:
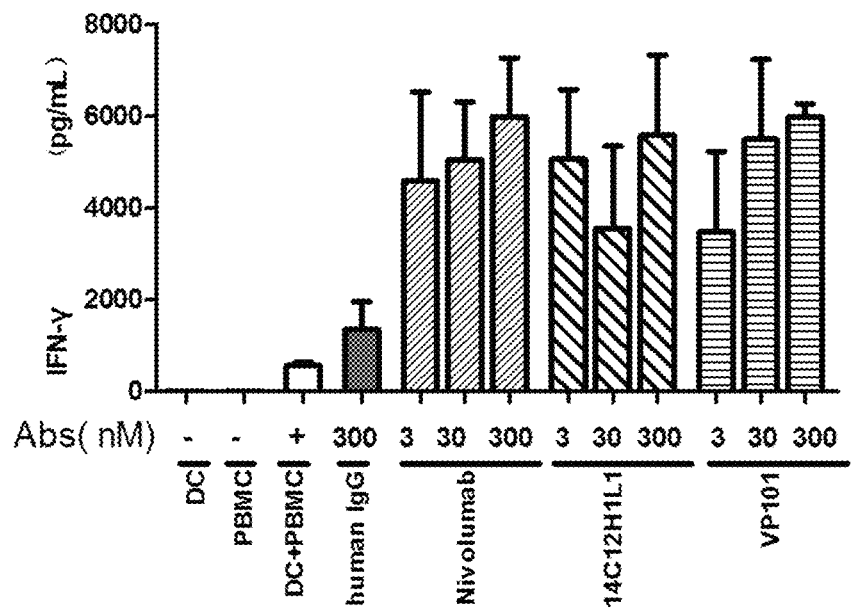
FIG. 23 shows the effect of VP101 on secretion of IFN-γ in mixed culture system of DC and PBMC cells.

The effect of VP101 on secretion of IFN-γ in mixed culture system of DC and PBMC cells is shown in FIG. 23. As can be seen in FIG. 23, VP101 can effectively promote secretion of IFN-γ in a dose-dependent manner. In addition, at doses of 30 nM and 300 nM, VP101 has greater activity in promoting secretion of IFN-γ than equivalent 14C12H1L1, and at dose level of 30 nM, it has greater activity in promoting secretion of IFN-γ than equivalent nivolumab.

2. Promotion of Secretion of IL-2 and IFN-γ by VP101, BsAbB7 and BsAbB8b in Mixed Culture System of DC and PBMC Cells Step 1 in this example was referred to for the experimental method, namely PBMCs were isolated by Ficoll-Paque Plus (GE Healthcare) and added to IL-4 (Peprotech 200-04, 1000 U/mL) and GM-CSF (Peprotech 300-03, 1000 U/mL) for 6 days of induction, and then TNF-α (Peprotech 300-01A, 200 U/mL) was additionally added for 3 days of induction to obtain mature DC cell.

On the day of co-culture, fresh PBMCs were isolated from peripheral blood of another donor, and the obtained mature DC cells were mixed with the freshly isolated PBMCs of another donor at a ratio of 1:10, and meanwhile antibodies at different concentrations (hIgG as a control) were added; after co-culture for 5-6 days, cell supernatant was collected and assayed for IL-2 and IFN-γ content using an ELISA kit (purchased from Dakewe).

Figure 24:
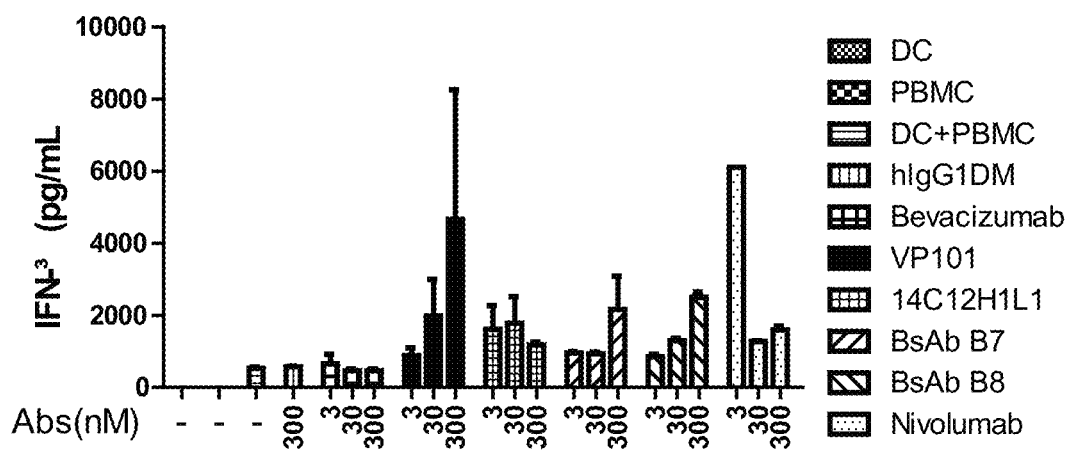
FIG. 24 shows the effect of VP101, BsAbB7 and BsAbB8 on secretion of IFN-γ in mixed culture system of DC and PBMC cells.

The effect of VP101 on secretion of IFN-γ in mixed culture system of DC and PBMC cells is shown in FIG. 24. As can be seen from FIG. 24, VP101 can effectively promote secretion of IFN-γ in a dose-dependent manner. The pharmacological activity of VP101 in promoting secretion of IFN-γ is significantly better than that of BsAbB7 and BsAbB8.

Figure 25:
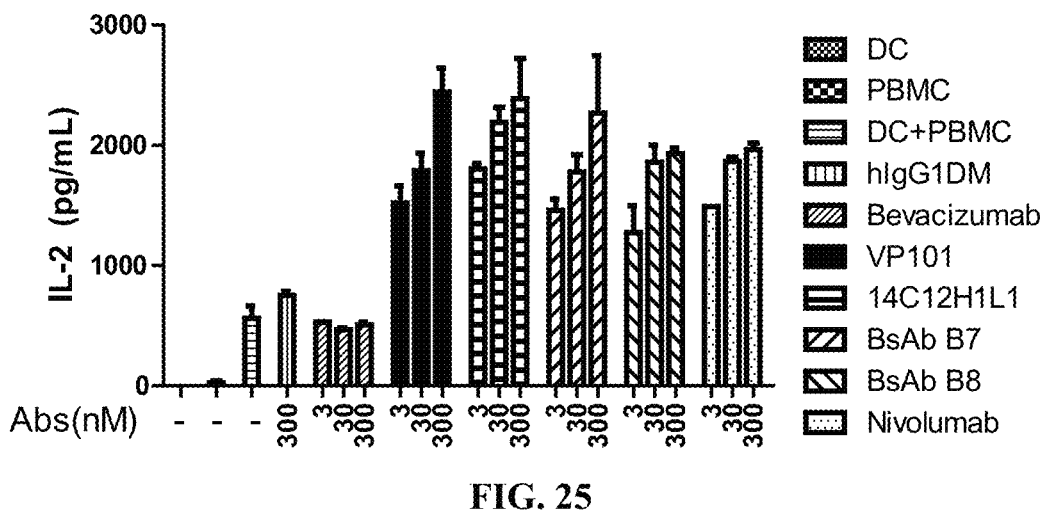
FIG. 25 shows the effect of VP101, BsAbB7 and BsAbB8 on secretion of IL-2 in mixed culture system of DC and PBMC cells.

The effect of VP101 on secretion of IL-2 in mixed culture system of DC and PBMC cells is shown in FIG. 25. As can be seen from FIG. 25, VP101 can effectively promote secretion of IL-2 in a dose-dependent manner, and the pharmacological activity of VP101 in promoting secretion of IL-2 is better than that of BsAbB7 and BsAbB8.

3. Promotion of Secretion of IL-2 and IFN-γ by VP101, 14C12H1L1 and Nivolumab in Mixed Culture System of PBMC and Raji-PD-L1 Cells PD-L1 was stably transfected into Raji cells through lentivirus infection, and Raji-PD-L1 cells stably expressing PD-L1 were obtained after dosing and screening; PBMCs, after two days of stimulation by SEB, were cultured in together with mitomycin C-treated Raji-PD-L1.

Figure 26:
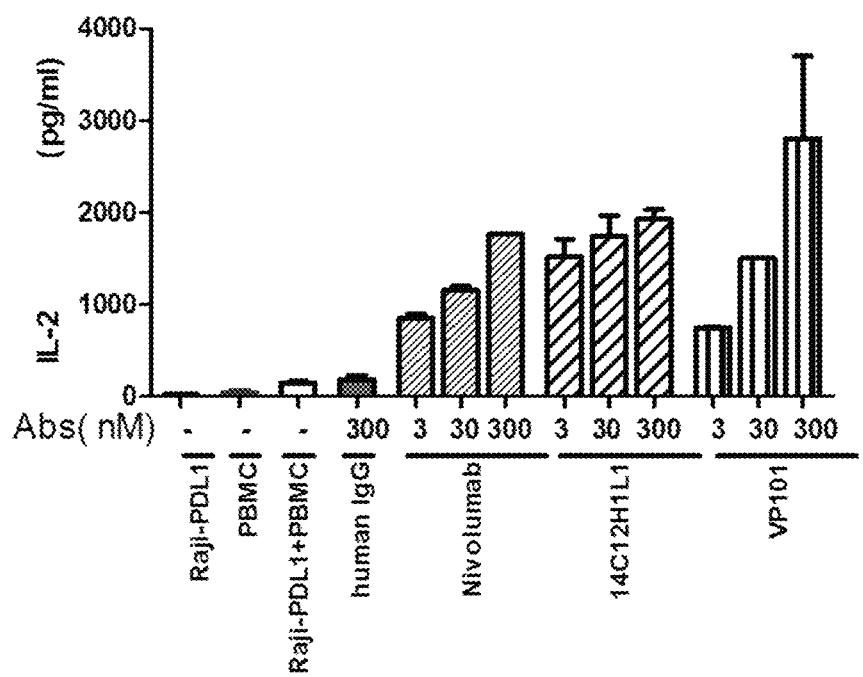
FIG. 26 shows the effect of antibodies 14C12H1L1 and VP101 on secretion of the cytokine IL-2 induced by mixed culture of PBMC and Raji-PD-L1 cells detected by ELISA.
Figure 27:
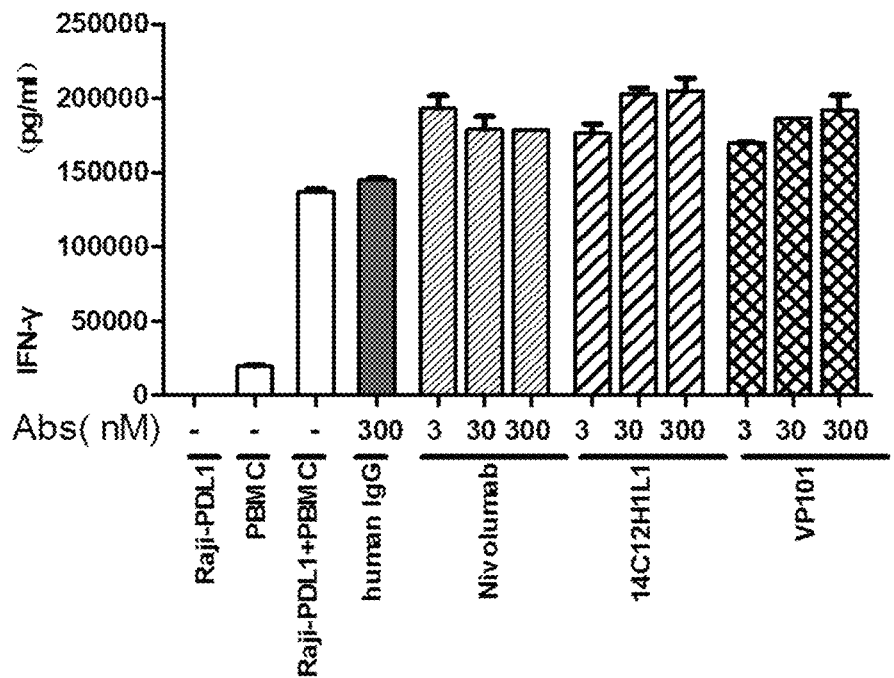
FIG. 27 shows effect of antibodies 14C12H1L1 and VP101 on secretion of the cytokine IFN-γ induced by mixed culture of PBMC and Raji-PD-L1 cells detected by ELISA.

The results are shown in FIGS. 26 and 27. The results show that VP101 can effectively promote secretion of IL-2 and IFN-γ, and at dose level of 300 nM, the activity of VP101 in promoting secretion of IL-2 is significantly better than that of equivalent 14C12H1L1 and nivolumab.

The isotype control antibody to be studied was Human Anti-Hen Lysozyme (anti-HEL, i.e., human IgG, abbreviated as hIgG), and it was prepared as described in Preparation Example 6 above.

4. The Promotion of Secretion of IL-2 and IFN-γ by VP101, BsAbB7 and BsAbB8 in Mixed Culture System of PBMC and Raji-PD-L1 Cells was Studied by Referring to the Experimental Method Described in Step 3 of this Example.

Figure 28:
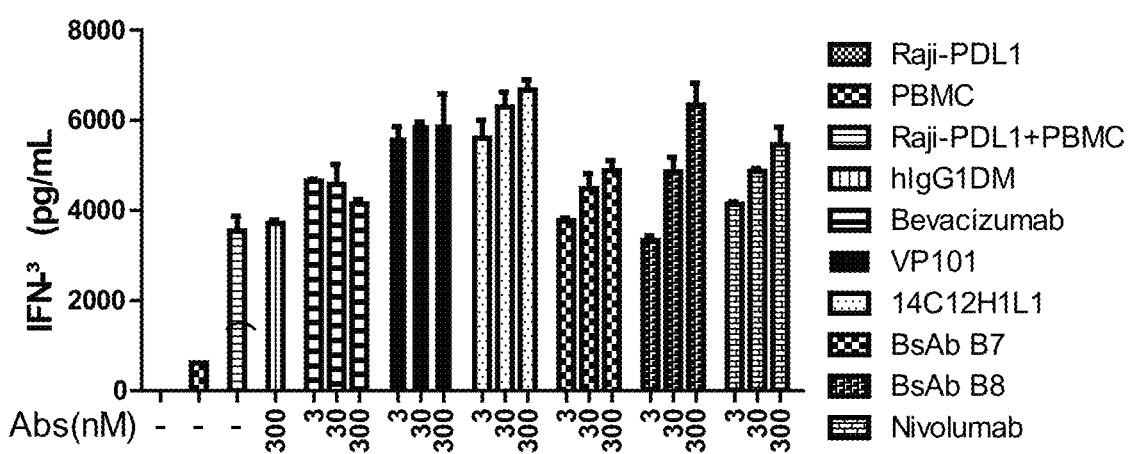
FIG. 28 shows effect of antibodies 14C12H1L1, VP101, BsAbB7 and BsAbB8 on secretion of the cytokine IFN-γ induced by mixed culture of PBMC and Raji-PD-L1 cells detected by ELISA.

The results of secretion of IFN-γ are shown in FIG. 28. The results show that VP101 can effectively promote secretion of IFN-γ in a dose-dependent manner. At the same time, VP101 is significantly better than BsAbB7 at the same dose, while the pharmacological activity of VP101 is significantly better than that of BsAbB8 at dose levels of 3 nM and 30 nM.

Figure 29:
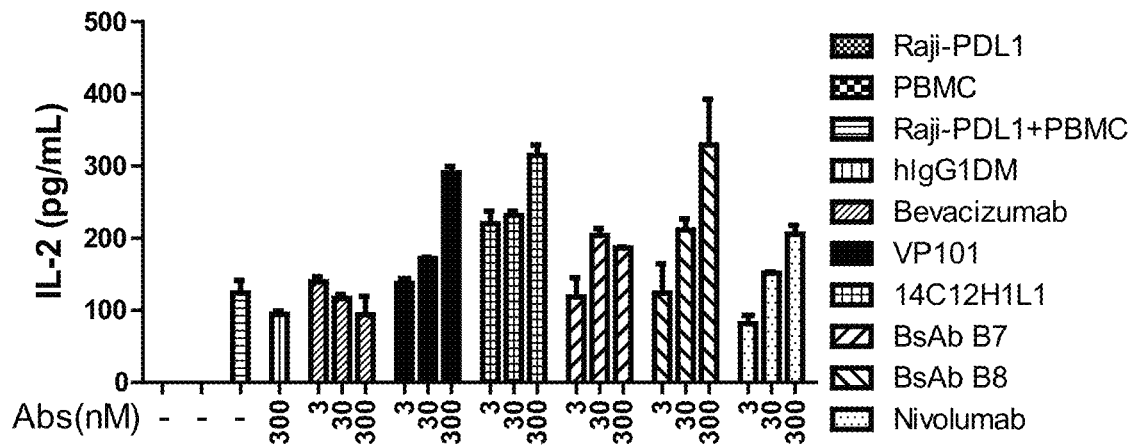
FIG. 29 shows effect of antibodies 14C12H1L1, VP101, BsAbB7 and BsAbB8 on secretion of the cytokine IL-2 induced by mixed culture of PBMC and Raji-PD-L1 cells detected by ELISA.

The results of secretion of IL-2 are shown in FIG. 29. The results show that VP101 can effectively promote secretion of IL-2 in a dose-dependent manner. At the same time, the pharmacological activity of VP101 is significantly better than that of BsAbB7 at doses of 3 nM and 300 nM, while VP101 is equivalent to BsAbB8 at the same dose.

Example 9; Experiment of Inhibition of Tumor Growth In Vivo by VP101

To detect the in vivo tumor-inhibiting activity of VP101, U87MG cells (human glioma cells, purchased from ATCC) were first inoculated subcutaneously into 5-7 week old female Scid Beige mice (purchased from Vital River), and the modeling and specific mode of administration were shown in Table 15. After the administration, the length and width of each group of tumors were measured, and the tumor volume was calculated.

TABLE 15

Dosing regimen of treating U87MG tumor xenograft Scid Beige mouse model with VP101

| Grouping | n | Tumor xenograft | Condition of administration |
|---|---|---|---|
| Isotype control 40 mg/kg | 7 | U-87MG, 5 million cells/mouse subcutaneously | Isotype control antibody, hIgG, 40 mg/kg, injected intravenously on days 0, 7 and 13 |
| Bevacizumab 30 mg/kg | 8 | | Bevacizumab 30 mg/kg, injected intravenously on days 0, 7 and 13 |
| VP101 40 mg/kg | 7 | | VP101 40 mg/kg, injected intravenously on days 0, 7 and 13 |
| VP101 4 mg/kg | 7 | | VP101 4 mg/kg, injected intravenously on days 0, 7 and 13 |

Figure 30:
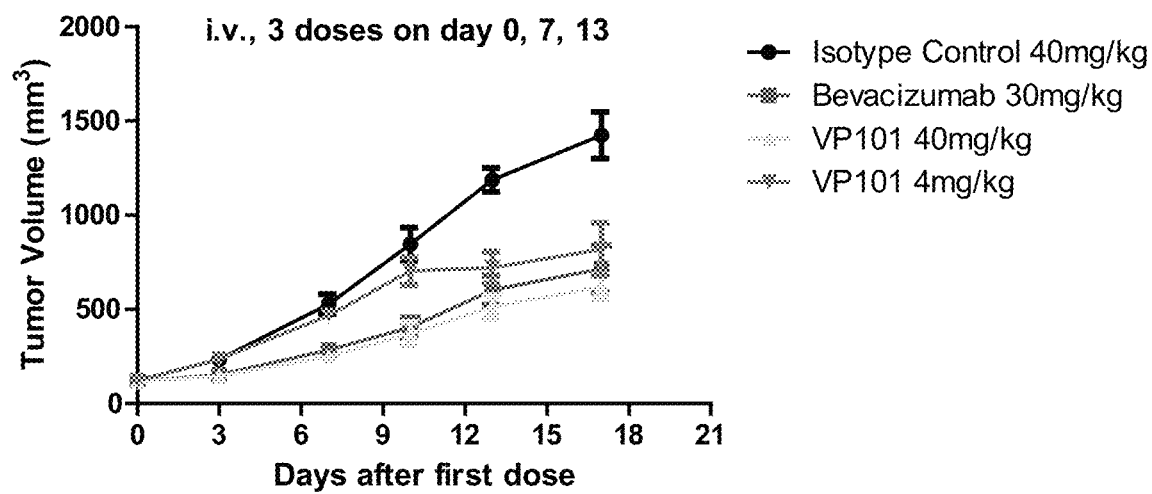
FIG. 30 shows the inhibition of tumor growth by VP101 at different concentrations.

The results are shown in FIG. 30. The results show that compared with an isotype control antibody hIgG (the preparation method is the same as that of the Preparation Example 6), bevacizumab and VP101 at different doses can effectively inhibit the growth of mouse tumors, and the high-dose VP101 is better than that of low-dose VP 101 in inhibiting tumors.

Figure 31:
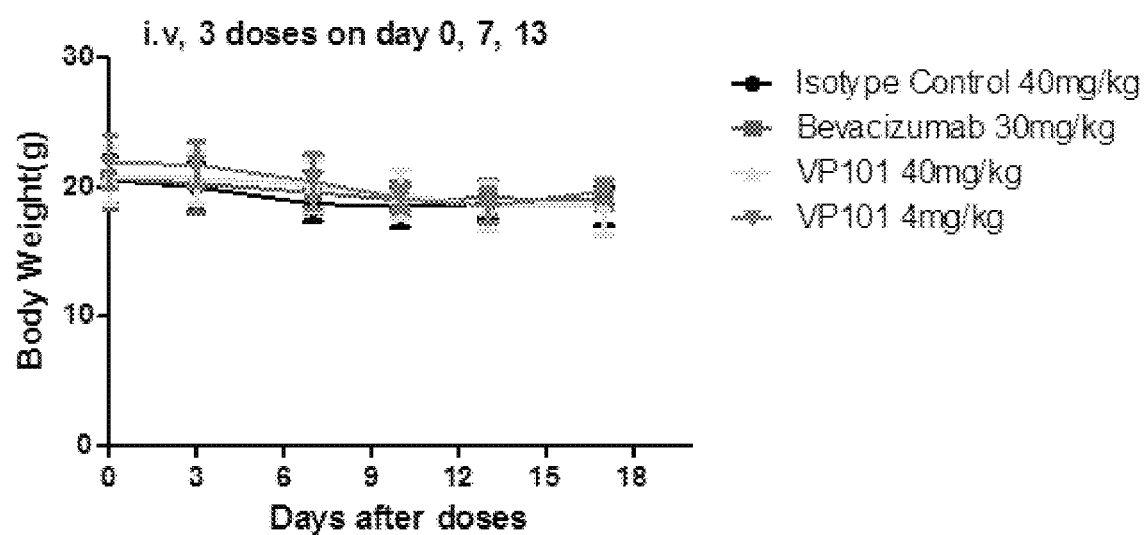
FIG. 31 shows effect of VP101 at different concentrations on body weight of mouse.

Furthermore, as shown in FIG. 31, VP101 does not affect the body weight of tumor-bearing mouse.

While the content of the present application has provided complete and clear description of its disclosed embodiments, it is not limited thereto. For those skilled in the art, modifications and replacements to the present invention are possible with the guidance of these descriptions, and such modifications and replacements are included within the scope of the present invention. The full scope of the present application is given by the appended claims and any equivalent thereof.

SEQUENCE LISTING

```
Sequence total quantity: 27
SEQ ID NO: 1                 moltype = AA  length = 171
FEATURE                      Location/Qualifiers
REGION                       1..171
                             note = The amino acid sequence of VEGFA-His
source                       1..171
                             mol_type = protein
                             organism = synthetic construct
SEQUENCE: 1
APMAEGGGQN HHEVVKFMDV YQRSYCHPIE TLVDIFQEYP DEIEYIFKPS CVPLMRCGGC    60
CNDEGLECVP TEESNITMQI MRIKPHQGQH IGEMSFLQHN KCECRPKKDR ARQENPCGPC   120
SERRKHLFVQ DPQTCKCSCK NTDSRCKARQ LELNERTCRC DKPRRHHHHH H            171

SEQ ID NO: 2                 moltype = DNA  length = 513
FEATURE                      Location/Qualifiers
misc_feature                 1..513
                             note = Nucleotide sequence of VEGFA-His
source                       1..513
                             mol_type = other DNA
                             organism = synthetic construct
SEQUENCE: 2
gcacccatgg ccgagggcgg cggccagaac caccacgagg tggtgaagtt catggacgtg    60
taccagagaa gctactgcca ccccatcgag accctggtgg acatcttcca ggagtacccc   120
gacgagatcg agtacatctt caagcccagc tgcgtgcccc tgatgagatg cggcggctgc   180
tgcaacgacg agggcctgga gtgcgtgccc accgaggaga gcaacatcac catgcagatc   240
atgagaatca agccccacca gggccagcac atcggcgaga tgagcttcct gcagcacaac   300
aagtgcgagt gcagacccaa gaaggacaga gccagacagg agaaccctg cggcccctgc    360
agcgagagaa gaaagcacct gttcgtgcag gaccccaga cctgcaagtg cagctgcaag   420
aacaccgaca gcagatgcaa ggccagacag ctggagctga acgagagaac ctgcagatgc   480
gacaagccca agagacatca tcaccatcac cac                                513

SEQ ID NO: 3                 moltype = AA  length = 998
FEATURE                      Location/Qualifiers
REGION                       1..998
                             note = The amino acid sequence of Fusion protein VEGFR2- hFc
source                       1..998
                             mol_type = protein
                             organism = synthetic construct
SEQUENCE: 3
MQSKVLLAVA LWLCVETRAA SVGLPSVSLD LPRLSIQKDI LTIKANTTLQ ITCRGQRDLD    60
WLWPNNQSGS EQRVEVTECS DGLFCKTLTI PKVIGNDTGA YKCFYRETDL ASVIYVYVQD   120
YRSPFIASVS DQHGVVYITE NKNKTVVIPC LGSISNLNVS LCARYPEKRF VPDGNRISWD   180
SKKGFTIPSY MISYAGMVFC EAKINDESYQ SIMYIVVVG YRIYDVVLSP SHGIELSVGE    240
KLVLNCTART ELNVGIDFNW EYPSSKHQHK KLVNRDLKTG SGSEMKKFLS TLTIDGVTRS   300
DQGLYTCAAS SGLMTKKNST FVRVHEKPFV AFGSGMESLV EATVGERVRI PAKYLGYPPP   360
EIKWYKNGIP LESNHTIKAG HVLTIMEVSE RDTGNYTVIL TNPISKEKQS HVVSLVVYVP   420
PQIGEKSLIS PVDSYQYGTT QTLTCTVYAI PPPHHIHWYW QLEEECANEP SQAVSVTNPY   480
PCEEWRSVED FQGGNKIEVN KNQFALIEGK NKTVSTLVIQ AANVSALYKC EAVNKVGRGE   540
RVISFHVTRG PEITLQPDMQ PTEQESVSLW CTADRSTFEN LTWYKLGPQP LPIHVGELPT   600
PVCKNLDTLW KLNATMFSNS TNDILIMELK NASLQDQGDY VCLAQDRKTK KRHCVVRQLT   660
VLERVAPTIT GNLENQTTSI GESIEVSCTA SGNPPPQIMW FKDNETLVED SGIVLKDGNR   720
NLTIRRVRKE DEGLYTCQAC SVLGCAKVEA FFIIEGAQEK TNLESRENLY FQGTHTCPPC   780
PAPELLGGPS VFLFPPKPKD TLMISRTPEV TCVVVDVSHE DPEVKFNWYV DGVEVHNAKT   840
KPREEQYNST YRVVSVLTVL HQDWLNGKEY KCKVSNKALP APIEKTISKA KGQPREPQVY   900
TLPPSRDELT KNQVSLTCLV KGFYPSDIAV EWESNGQPEN NYKTTPPVLD SDGSFFLYSK   960
LTVDKSRWQQ GNVFSCSVMH EALHNHYTQK SLSLSPGK                           998

SEQ ID NO: 4                 moltype = DNA  length = 2997
FEATURE                      Location/Qualifiers
misc_feature                 1..2997
                             note = Nucleotide sequence of Fusion protein VEGFR2- hFc
source                       1..2997
                             mol_type = other DNA
                             organism = synthetic construct
SEQUENCE: 4
atgcagagca aggtgctgct ggccgtcgcc ctgtggctct gcgtggagac ccggccgcc     60
tctgtgggtt tgcctagtgt ttctcttgat ctgcccaggc tcagcataca aaaagacata   120
cttacaatta aggctaatac aactcttcaa attacttgca ggggacagag ggacttggac   180
tggctttggc ccaataatca gagtggcagt gagcaaaggg tggaggtgac tgagtgcagc   240
gatggcctct ctgtaagac actcacaatt ccaaaagtga tcggaaatga cactggagcc    300
tacaagtgct ctaccgggga aactgacttg gcctcggtca tttatgtcta tgttcaagat   360
tacagatctc catttattgc ttctgttagt gaccaacatg gagtcgtgta cattactgag   420
aacaaaaaca aaactgtggt gattccatgt ctcgggtcca tttcaaatct caacgtgtca   480
ctttgtgcaa gataccagaa aagagattt gttcctgatg gtaacagaat ttcctgggac   540
agcaagaagg gctttactat tccagctac atgatcagct atgctggcat ggtcttctgt   600
gaagcaaaaa ttaatgatga agttaccag tctattatgt acatagttgt cgttgtaggg   660
tataggattt atgatgtggt tctgagtccg tctcatggaa ttgaactatc tgttggagaa   720
aagcttgtct taaattgtac agcaagaact gaactaaatg tggggattga cttcaactgg   780
```

-continued

```
gaatacccct tcttcgaagca tcagcataag aaacttgtaa accgagacct aaaaacccag    840
tctgggagtg agatgaagaa attttttgagc accttaacta tagatggtgt aacccggagt    900
gaccaaggat tgtacacctg tgcagcatcc agtgggctga tgaccaagaa gaacagcaca    960
tttgtcaggt ccatgaaaaa accttttgtt gcttttggaa gtggcatgga atctctggtg   1020
gaagccacgg tgggggacg tgtcagaatc cctgcgaagt accttggtta cccacccca    1080
gaaataaaat ggtataaaaa tggaataccc cttgagtcca atcacacaat taaagcgggg   1140
catgtactga cgattatgga agtgagtgaa agagacacag gaattacac tgtcatcctt    1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcgtca acaaagtcgg gagaggagag   1620
agggtgatct ccttccacgt gaccaggggg cctgaaatta ctttgcaacc tgacatgcag   1680
cccactgagc aggagagcgt gtcttttgtgg tgcactgcag acagatctac gtttgagaac   1740
ctcacatggt acaagcttgg cccacagcct ctgccaatcc atgtgggaga gttgcccaca   1800
cctgtttgca agaacttgga tactcttttgg aaattgaatg ccaccatgtt tctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
gggaaagca tcgaagtctc atgcacggca tctgggaatc cccctccaca gatcatgtgg   2100
tttaaagata tgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttcataa tagaaggtgc ccaggaaaag   2280
acgaacttgg aatctagaga aaacctgtat tttcaggcg ctcacacatg cccaccgtcc   2340
ccagcacctg aactcctggg gggaccgtca gtcttcctct tccccccaaa acccaaggac   2400
accctcatga tctcccggac ccctgaggtc acatgcgtgg tggtggacgt gagccacgaa   2460
gaccctgagg tcaagttcaa ctggtacgtg acggcgtgg aggtgcataa tgccaagaca   2520
aagccgcggg aggagcagta caacagcacg taccgtgtg tcagcgtcct caccgtcctg   2580
caccaggact ggctgaatgg caaggagtac aagtgcaagg tctccaacaa agccctccca   2640
gcccccatcg agaaaaccat ctccaaagcc aaagggcagc cccgagaacc acaggtgtac   2700
accctgccc catcccggga tgagctgacc aagaaccagg tcagcctgac ctgcctggtc   2760
aaaggcttct atcccagcga catcgccgtg gagtgggaga gcaatgggca gccggagaac   2820
aactacaaga ccacgcctcc cgtgttggac tccgacggct ccttcttcct ctacagcaag   2880
ctcaccgtgg acaagagcag gtggcagcag gggaacgtct tctcatgctc cgtgatgcat   2940
gaggctctgc acaaccacta cacgcagaag agcctctccc tgtctcccgg gaaatga     2997

SEQ ID NO: 5              moltype = AA   length = 123
FEATURE                   Location/Qualifiers
REGION                    1..123
                          note = The amino acid sequence of Bevacizumab heavy chain
                           variable region
source                    1..123
                          mol_type = protein
                          organism = synthetic construct
SEQUENCE: 5
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSS                                                                 123

SEQ ID NO: 6              moltype = DNA   length = 369
FEATURE                   Location/Qualifiers
misc_feature              1..369
                          note = Nucleotide sequence of Bevacizumab heavy chain
                           variable region
source                    1..369
                          mol_type = other DNA
                          organism = synthetic construct
SEQUENCE: 6
gaggtgcagc tggtcgagtc cggggggggg ctggtcagc caggcgggtc tctgaggctg     60
agttgcgccg cttcagggta caccttcaca aactatggaa tgaattgggt gcgccaggca   120
ccaggaaagg gactggagtg ggtcggctgg atcaacactt acaccgggga acctacctat   180
gcagccgact ttaagcggcg gttcaccttc agcctggata caagcaaatc cactgcctac   240
ctgcagatga acagcctgcg agctgaggac accgcagtct actattgc taaatatccc     300
cactactatg ggagcagcca ttggtatttt gacgtgtggg gcaggggac tctggtgaca   360
gtgagcagc                                                           369

SEQ ID NO: 7              moltype = AA   length = 107
FEATURE                   Location/Qualifiers
REGION                    1..107
                          note = The amino acid sequence of Bevacizumab light chain
                           variable region
source                    1..107
                          mol_type = protein
                          organism = synthetic construct
SEQUENCE: 7
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIK                 107
```

```
SEQ ID NO: 8              moltype = DNA  length = 321
FEATURE                   Location/Qualifiers
misc_feature              1..321
                          note = Nucleotide sequence of Bevacizumab light chain
                           variable region
source                    1..321
                          mol_type = other DNA
                          organism = synthetic construct
SEQUENCE: 8
gatattcaga tgactcagag cccctcctcc ctgtccgcct ctgtgggcga cagggtcacc   60
atcacatgca gtgcttcaca ggatatttcc aactacctga ttggtatca gcagaagcca  120
ggaaaagcac ccaaggtgct gatctacttc actagctccc tgcactcagg agtgccaagc  180
cggttcagcg gatccggatc tggaaccgac tttactctga ccatttctag tctgcagcct  240
gaggatttcg ctacatacta ttgccagcag tattctaccg tgccatggac atttggccag  300
gggactaaag tcgagatcaa g                                            321

SEQ ID NO: 9              moltype = AA   length = 118
FEATURE                   Location/Qualifiers
REGION                    1..118
                          note = The amino acid sequence of humanized antibody
                           14C12H1L1 heavy chain variable region
source                    1..118
                          mol_type = protein
                          organism = synthetic construct
SEQUENCE: 9
EVQLVESGGG LVQPGGSLRL SCAASGFAFS SYDMSWVRQA PGKGLDWVAT ISGGGRYTYY   60
PDSVKGRFTI SRDNSKNNLY LQMNSLRAED TALYYCANRY GEAWFAYWGQ GTLVTVSS   118

SEQ ID NO: 10             moltype = DNA  length = 354
FEATURE                   Location/Qualifiers
misc_feature              1..354
                          note = Nucleotide sequence of humanized antibody 14C12H1L1
                           heavy chain variable region
source                    1..354
                          mol_type = other DNA
                          organism = synthetic construct
SEQUENCE: 10
gaagtgcagc tggtcgagtc tgggggaggg ctggtgcagc ccggcgggtc actgcgactg   60
agctgcgcag cttccggatt cgcctttagc tcctacgaca tgtcctgggt gcgacaggca  120
ccaggaaagg gactgactg gtcgctact atctcaggag gcgggagata cacctactat  180
cctgacagc tcaaggccg gttcacaatc tctagagata cagtaagaa caatctgtat  240
ctgcagatga acagcctgag ggctgaggac accgcactgt actattgtgc aaccgctac  300
ggggaagcat ggtttgccta ttgggggcag ggaaccctgg tgacagtctc tagt        354

SEQ ID NO: 11             moltype = AA   length = 107
FEATURE                   Location/Qualifiers
REGION                    1..107
                          note = The amino acid sequence of humanized antibody
                           14C12H1L1 light chain variable region
source                    1..107
                          mol_type = protein
                          organism = synthetic construct
SEQUENCE: 11
DIQMTQSPSS MSASVGDRVT FTCRASQDIN TYLSWFQQKP GKSPKTLIYR ANRLVSGVPS   60
RFSGSGSGQD YTLTISSLQP EDMATYYCLQ YDEFPLTFGA GTKLELK                107

SEQ ID NO: 12             moltype = DNA  length = 321
FEATURE                   Location/Qualifiers
misc_feature              1..321
                          note = Nucleotide sequence of humanized antibody 14C12H1L1
                           light chain variable region
source                    1..321
                          mol_type = other DNA
                          organism = synthetic construct
SEQUENCE: 12
gacattcaga tgactcagag cccctcctcc atgtccgcct ctgtgggcga cagggtcacc   60
ttcacatgcc gcgctagtca ggatatcaac acctaccga gctggtttca gcagaagcca  120
gggaaaagcc ccaagacact gatctaccgg gctaataagc tggtctctgg agtcccaagt  180
cggttcagtg gctcagggag cggacaggac tacactctga ccatcagctc cctgcagcct  240
gaggacatgg caacctacta ttgcctgcag tatgatgagt tcccactgac ctttggcgcc  300
gggacaaaac tggagctgaa g                                            321

SEQ ID NO: 13             moltype = AA   length = 20
FEATURE                   Location/Qualifiers
REGION                    1..20
                          note = The amino acid sequence of Linker 1
source                    1..20
                          mol_type = protein
```

```
                        organism = synthetic construct
SEQUENCE: 13
GGGGSGGGGS GGGGSGGGGS                                                           20

SEQ ID NO: 14           moltype = AA   length = 5
FEATURE                 Location/Qualifiers
REGION                  1..5
                        note = linker fragment
source                  1..5
                        mol_type = protein
                        organism = synthetic construct
SEQUENCE: 14
GGGGS                                                                            5

SEQ ID NO: 15           moltype = AA   length = 8
FEATURE                 Location/Qualifiers
REGION                  1..8
                        note = HCDR1 of Antibody Bevacizumab
source                  1..8
                        mol_type = protein
                        organism = synthetic construct
SEQUENCE: 15
GYTFTNYG                                                                         8

SEQ ID NO: 16           moltype = AA   length = 8
FEATURE                 Location/Qualifiers
REGION                  1..8
                        note = HCDR2 of Antibody Bevacizumab
source                  1..8
                        mol_type = protein
                        organism = synthetic construct
SEQUENCE: 16
INTYTGEP                                                                         8

SEQ ID NO: 17           moltype = AA   length = 16
FEATURE                 Location/Qualifiers
REGION                  1..16
                        note = HCDR3 of Antibody Bevacizumab
source                  1..16
                        mol_type = protein
                        organism = synthetic construct
SEQUENCE: 17
AKYPHYYGSS HWYFDV                                                               16

SEQ ID NO: 18           moltype = AA   length = 6
FEATURE                 Location/Qualifiers
REGION                  1..6
                        note = LCDR1 of Antibody Bevacizumab
source                  1..6
                        mol_type = protein
                        organism = synthetic construct
SEQUENCE: 18
QDISNY                                                                           6

SEQ ID NO: 19           moltype =    length =
SEQUENCE: 19
000

SEQ ID NO: 20           moltype = AA   length = 9
FEATURE                 Location/Qualifiers
REGION                  1..9
                        note = LCDR3 of Antibody Bevacizumab
source                  1..9
                        mol_type = protein
                        organism = synthetic construct
SEQUENCE: 20
QQYSTVPWT                                                                        9

SEQ ID NO: 21           moltype = AA   length = 8
FEATURE                 Location/Qualifiers
REGION                  1..8
                        note = HCDR1 of Antibody 14C12H1L1
source                  1..8
                        mol_type = protein
                        organism = synthetic construct
SEQUENCE: 21
GFAFSSYD                                                                         8

SEQ ID NO: 22           moltype = AA   length = 8
```

```
FEATURE                 Location/Qualifiers
REGION                  1..8
                        note = HCDR2 of Antibody 14C12H1L1
source                  1..8
                        mol_type = protein
                        organism = synthetic construct
SEQUENCE: 22
ISGGGRYT                                                                    8

SEQ ID NO: 23           moltype = AA  length = 11
FEATURE                 Location/Qualifiers
REGION                  1..11
                        note = HCDR3 of Antibody 14C12H1L1
source                  1..11
                        mol_type = protein
                        organism = synthetic construct
SEQUENCE: 23
ANRYGEAWFA Y                                                               11

SEQ ID NO: 24           moltype = AA  length = 6
FEATURE                 Location/Qualifiers
REGION                  1..6
                        note = LCDR1 of Antibody 14C12H1L1
source                  1..6
                        mol_type = protein
                        organism = synthetic construct
SEQUENCE: 24
QDINTY                                                                      6

SEQ ID NO: 25           moltype =   length =
SEQUENCE: 25
000

SEQ ID NO: 26           moltype = AA  length = 9
FEATURE                 Location/Qualifiers
REGION                  1..9
                        note = LCDR3 of Antibody 14C12H1L1
source                  1..9
                        mol_type = protein
                        organism = synthetic construct
SEQUENCE: 26
LQYDEFPLT                                                                   9

SEQ ID NO: 27           moltype = AA  length = 245
FEATURE                 Location/Qualifiers
source                  1..245
                        mol_type = protein
                        note = 14C12H1V- Linker1-14C12L1V scFv
                        organism = synthetic construct
SEQUENCE: 27
EVQLVESGGG LVQPGGSLRL SCAASGFAFS SYDMSWVRQA PGKGLDWVAT ISGGGRYTYY     60
PDSVKGRFTI SRDNSKNNLY LQMNSLRAED TALYYCANRY GEAWFAYWGQ GTLVTVSSGG    120
GGSGGGGSGG GGSGGGGSDI QMTQSPSSMS ASVGDRVTFT CRASQDINTY LSWFQQKPGK    180
SPKTLIYRAN RLVSGVPSRF SGSGSGQDYT LTISSLQPED MATYYCLQYD EFPLTFGAGT    240
KLELK                                                                245
```

The invention claimed is:

1. A bispecific antibody, wherein the bispecific antibody comprises:
   (a) an anti-VEGFA IgG1 immunoglobulin that binds to human VEGFA, wherein the anti-VEGFA IgG1 immunoglobulin comprises two pairs of polypeptide chains, wherein each of the two pairs of polypeptide chains comprises a heavy chain polypeptide and a light chain polypeptide, wherein:
      (i) the heavy chain polypeptide comprises:
      a heavy chain variable region (VH region), wherein the amino acid sequence of the VH region is set forth in SEQ ID NO:5, and
      a human Ig gamma-1 chain constant region; and
      (ii) the light chain polypeptide comprises:
      a light chain variable region (VL region), wherein the amino acid sequence of the VL region is set forth in SEQ ID NO:7, and
      a human Ig kappa constant region; and
   (b) two anti-PD-1 single chain antibodies that bind to human PD-1, wherein each of the two anti-PD-1 single chain antibodies comprises:
      (i) a VH region, wherein the amino acid sequence of the VH region is set forth in SEQ ID NO:9, and
      (ii) a VL region, wherein the amino acid sequence of the VL region is set forth in SEQ ID NO:11,
   wherein the VH region and the VL region of one of the two anti-PD-1 single chain antibodies are linked by a first linker having the amino acid sequence set forth in SEQ ID NO:13, and the VH region and the VL region of the other of the two anti-PD-1 single chain antibodies are linked by a second linker having the amino acid sequence set forth in SEQ ID NO:13; and
   wherein one terminus of one of the two anti-PD-1 single chain antibodies is linked to the C-terminus of one of the two heavy chain polypeptides of the anti-VEGFA IgG1 immunoglobulin via a third linker having the amino acid sequence set forth in SEQ ID NO:13 and wherein one terminus of the other of the two anti-PD-1 single chain antibodies is linked to the C-terminus of the other of the two heavy chain polypeptides of the anti-VEGFA IgG1 immunoglobulin via a fourth linker having the amino acid sequence set forth in SEQ ID NO:13.

2. The bispecific antibody according to claim 1, wherein each of the two anti-PD-1 single chain antibodies comprises the amino acid sequence of:

(SEQ ID NO: 27)
EVQLVESGGGLVQPGGSLRLSCAASGFAFSSYDMSWVRQAPGKGLDWVAT

ISGGGRYTYYPDSVKGRFTISRDNSKNNLYLQMNSLRAEDTALYYCANRY

GEAWFAYWGQGTLVTVSSGGGGSGGGGSGGGGSGGGGSDIQMTQSPSSMS

ASVGDRVTFTCRASQDINTYLSWFQQKPGKSPKTLIYRANRLVSGVPSRF

SGSGSGQDYTLTISSLQPEDMATYYCLQYDEFPLTFGAGTKLELK.

3. The bispecific antibody according to claim 1, wherein: the VH region of one of the two anti-PD-1 single chain antibodies is linked to the C-terminus of one of the two heavy chain polypeptides of the anti-VEGFA IgG1 immunoglobulin via a linker having the amino acid sequence set forth in SEQ ID NO:13; and the VH region of the other of the two anti-PD-1 single chain antibodies is linked to the C-terminus of the other of the two heavy chain polypeptides of the anti-VEGFA IgG1 immunoglobulin via a linker having the amino acid sequence set forth in SEQ ID NO:13.

4. The bispecific antibody according to claim 1, wherein the VL region of one of the two anti-PD-1 single chain antibodies is linked to the C-terminus of one of the two heavy chain polypeptides of the anti-VEGFA IgG1 immunoglobulin via a linker having the amino acid sequence set forth in SEQ ID NO:13 and the VL region of the other of the two anti-PD-1 single chain antibodies is linked to the C-terminus of the other of the two heavy chain polypeptides of the anti-VEGFA IgG1 immunoglobulin via a linker having the amino acid sequence set forth in SEQ ID NO:13.

5. The bispecific antibody according to claim 1, wherein:
for one of the two anti-PD-1 single chain antibodies, the N-terminus of the VH region is linked to the C-terminus of one of the two heavy chain polypeptides of the anti-VEGFA IgG1 immunoglobulin via a linker having the amino acid sequence set forth in SEQ ID NO:13 and the C-terminus of the VH region of the anti-PD-1 single chain antibody is linked to the N-terminus of the VL region of the anti-PD-1 single chain antibody via a linker having the amino acid sequence set forth in SEQ ID NO:13; and
for the other of the two anti-PD-1 single chain antibodies, the N-terminus of the VH region is linked to the C-terminus of the other of the two heavy chain polypeptides of the anti-VEGFA IgG1 immunoglobulin via a linker having the amino acid sequence set forth in SEQ ID NO:13 and the C-terminus of the VH region of the anti-PD-1 single chain antibody is linked to the N-terminus of the VL region of the anti-PD-1 single chain antibody via a linker having the amino acid sequence set forth in SEQ ID NO:13.

6. A pharmaceutical composition comprising the bispecific antibody according to claim 1 and a pharmaceutically acceptable excipient.

7. A pharmaceutical composition comprising the bispecific antibody according to claim 5 and a pharmaceutically acceptable excipient.

8. A bispecific antibody in IgG-scFv form, wherein:
(a) the IgG portion of the bispecific antibody is an anti-human VEGFA immunoglobulin, wherein the anti-human VEGFA immunoglobulin comprises two pairs of polypeptide chains, wherein each of the two pairs of polypeptide chains comprises a heavy chain polypeptide and a light chain polypeptide, wherein:
(a)(i) the heavy chain polypeptide comprises a heavy chain variable region (VH region), wherein the amino acid sequence of the VH region is set forth in SEQ ID NO:5; and
(a)(ii) the light chain polypeptide comprises a light chain variable region (VL region), wherein the amino acid sequence of the VL region is set forth in SEQ ID NO:7; and
(b) the scFv portion of the bispecific antibody is two anti-human PD-1 single chain antibodies, wherein each of the two anti-human PD-1 single-chain antibodies comprises:
(b)(i) the amino acid sequence set forth in SEQ ID NO:9, linked via
(b)(ii) a linker to
(b)(iii) the amino acid sequence set forth in SEQ ID NO:11,
wherein one terminus of each of the two anti-human PD-1 single chain antibodies is linked to the C-terminus of one of the two heavy chain polypeptides of the anti-human VEGFA immunoglobulin via a linker, and
wherein the linker of (b)(ii) and the linker linking a terminus of an anti-human PD-1 single chain antibody to the C-terminus of one of the two heavy chain polypeptides are each independently a [GGGGS (SEQ ID NO: 14)]m linker, wherein m is 1, 2, 3, 4, 5, or 6.

9. The bispecific antibody according to claim 8, wherein the linker of (b)(ii) and the linker linking a terminus of an anti-human PD-1 single chain antibody to the C-terminus of one of the two heavy chain polypeptides are the same.

10. The bispecific antibody according to claim 8, wherein each of the two anti-human PD-1 single chain antibodies comprises the amino acid sequence of:

(SEQ ID NO: 27)
EVQLVESGGGLVQPGGSLRLSCAASGFAFSSYDMSWVRQAPGKGLDWVAT

ISGGGRYTYYPDSVKGRFTISRDNSKNNLYLQMNSLRAEDTALYYCANRY

GEAWFAYWGQGTLVTVSSGGGGSGGGGSGGGGSGGGGSDIQMTQSPSSMS

ASVGDRVTFTCRASQDINTYLSWFQQKPGKSPKTLIYRANRLVSGVPSRF

SGSGSGQDYTLTISSLQPEDMATYYCLQYDEFPLTFGAGTKLELK.

11. The bispecific antibody according to claim 8, wherein the amino acid sequence set forth in SEQ ID NO:9 is linked to the C-terminus of one of the two heavy chain polypeptides of the anti-human VEGFA immunoglobulin.

12. The bispecific antibody according to claim 8, wherein the amino acid sequence set forth in SEQ ID NO:11 is linked to the C-terminus of one of the two heavy chain polypeptides of the anti-human VEGFA immunoglobulin.

13. The bispecific antibody according to claim 8, wherein:
for one of the two anti-human PD-1 single chain antibodies, the N-terminus of the amino acid sequence set forth in SEQ ID NO:9 is linked to the C-terminus of one of the two heavy chain polypeptides of the anti-human VEGFA immunoglobulin and the C-terminus of the amino acid sequence set forth in SEQ ID NO:9 is linked to the N-terminus of the amino acid sequence set forth in SEQ ID NO:11;

for the other of the two anti-human PD-1 single chain antibodies, the N-terminus of the amino acid sequence set forth in SEQ ID NO:9 is linked to the C-terminus of the other of the two heavy chain polypeptides of the anti-human VEGFA immunoglobulin and the C-terminus of the amino acid sequence set forth in SEQ ID NO:9 is linked to the N-terminus of the amino acid sequence set forth in SEQ ID NO:11; and for each of the two anti-human PD-1 single chain antibodies, the same linker amino acid sequence links the amino acid sequence set forth in SEQ ID NO:9 to the amino acid sequence set forth in SEQ ID NO:11; and/or for each of the two anti-human PD-1 single chain antibodies, the same linker amino acid sequence links the amino acid sequence set forth in SEQ ID NO:9 to the C-terminus of a heavy chain polypeptide of the anti-human VEGFA immunoglobulin.

14. The bispecific antibody according to claim 10, wherein:

for one of the two anti-human PD-1 single chain antibodies, the N-terminus of the amino acid sequence set forth in SEQ ID NO:27 is linked to the C-terminus of one of the two heavy chain polypeptides of the anti-human VEGFA immunoglobulin; and for the other of the two anti-human PD-1 single chain antibodies, the N-terminus of the amino acid sequence set forth in SEQ ID NO:27 is linked to the C-terminus of the other of the two heavy chain polypeptides of the anti-human VEGFA immunoglobulin.

15. A pharmaceutical composition comprising the bispecific antibody according to claim 8 and a pharmaceutically acceptable excipient.

16. A pharmaceutical composition comprising the bispecific antibody according to claim 14 and a pharmaceutically acceptable excipient.

17. A bispecific antibody, comprising:
(a) an anti-VEGFA immunoglobulin that binds to human VEGFA, wherein the anti-VEGFA immunoglobulin comprises two pairs of polypeptide chains, wherein each of the two pairs of polypeptide chains comprises a heavy chain polypeptide and a light chain polypeptide, wherein:
(i) the heavy chain polypeptide comprises:
a heavy chain variable region (VH region), wherein the amino acid sequence of the VH region is set forth in SEQ ID NO:5, and
an immunoglobulin CH1-CH2-CH3; and
(ii) the light chain polypeptide comprises:
a light chain variable region (VL region), wherein the amino acid sequence of the VL region is set forth in SEQ ID NO:7, and
an immunoglobulin CL; and
(b) two anti-PD-1 single chain antibodies that bind to human PD-1, wherein each of the two anti-PD-1 single chain antibodies comprises:
(b)(i) the amino acid sequence set forth in SEQ ID NO:9 and
(b)(ii) the amino acid sequence set forth in SEQ ID NO:11,
wherein in one of the two anti-PD-1 single chain antibodies, a first linker links the amino acid sequences set forth in SEQ ID NOs:9 and 11 to one another, and in the other of the two anti-PD-1 single chain antibodies, a second linker links the amino acid sequences set forth in SEQ ID NOs:9 and 11 to one another, wherein one terminus of one of the two anti-PD-1 single chain antibodies is linked to the C-terminus of one of the two heavy chain polypeptides of the anti-VEGFA immunoglobulin via a third linker, and wherein one terminus of the other of the two anti-PD-1 single chain antibodies is linked to the C-terminus of the other of the two heavy chain polypeptides of the anti-VEGFA immunoglobulin via a fourth linker, and wherein the first linker and the second linker have the same amino acid sequence as one another, and wherein the third linker and the fourth linker have the same amino acid sequence as one another, and wherein the first linker and the second linker are a [GGGGS (SEQ ID NO:14)]m linker, wherein m is 1, 2, 3, 4, 5, or 6, and the third linker and the fourth linker are a [GGGGS (SEQ ID NO:14)]m linker, wherein m is 1, 2, 3, 4, 5, or 6.

18. The bispecific antibody according to claim 17, wherein each of the two anti-PD-1 single chain antibodies comprises the amino acid sequence of:

```
                                         (SEQ ID NO: 27)
EVQLVESGGGLVQPGGSLRLSCAASGFAFSSYDMSWVRQAPGKGLDWVAT

ISGGGRYTYYPDSVKGRFTISRDNSKNNLYLQMNSLRAEDTALYYCANRY

GEAWFAYWGQGTLVTVSSGGGGSGGGGSGGGGSGGGGSDIQMTQSPSSMS

ASVGDRVTFTCRASQDINTYLSWFQQKPGKSPKTLIYRANRLVSGVPSRF

SGSGSGQDYTLTISSLQPEDMATYYCLQYDEFPLTFGAGTKLELK.
```

19. The bispecific antibody according to claim 17, wherein the amino acid sequence set forth in SEQ ID NO:9 is linked to the C-terminus of one of the two heavy chain polypeptides of the anti-VEGFA immunoglobulin.

20. The bispecific antibody according to claim 17, wherein the amino acid sequence set forth in SEQ ID NO:11 is linked to the C-terminus of one of the two heavy chain polypeptides of the anti-human VEGFA immunoglobulin.

21. The bispecific antibody according to claim 17, wherein:

for one of the two anti-PD-1 single chain antibodies, the N-terminus of the amino acid sequence set forth in SEQ ID NO:9 is linked to the C-terminus of the other of the two heavy chain polypeptides of the anti-VEGFA immunoglobulin and the C-terminus of the amino acid sequence set forth in SEQ ID NO:9 is linked to the N-terminus of the amino acid sequence set forth in SEQ ID NO:11; and for the other of the two anti-PD-1 single chain antibodies, the N-terminus of the amino acid sequence set forth in SEQ ID NO:9 is linked to the C-terminus of one of the two heavy chain polypeptides of the anti-VEGFA immunoglobulin and the C-terminus of the amino acid sequence set forth in SEQ ID NO:9 is linked to the N-terminus of the amino acid sequence set forth in SEQ ID NO:11.

22. The bispecific antibody according to claim 18, wherein:

for one of the two anti-PD-1 single chain antibodies, the N-terminus of the amino acid sequence set forth in SEQ ID NO:27 is linked to the C-terminus of one of the two heavy chain polypeptides of the anti-VEGFA immunoglobulin; and for the other of the two anti-PD-1 single chain antibodies, the N-terminus of the amino acid sequence set forth in SEQ ID NO:27 is linked to the C-terminus of the other of the two heavy chain polypeptides of the anti-VEGFA immunoglobulin.

23. A pharmaceutical composition comprising the bispecific antibody according to claim 17 and a pharmaceutically acceptable excipient.

24. A pharmaceutical composition comprising the bispecific antibody according to claim 22 and a pharmaceutically acceptable excipient.

\* \* \* \* \*

UNITED STATES PATENT AND TRADEMARK OFFICE
CERTIFICATE OF CORRECTION

PATENT NO. : 12,195,527 B2
APPLICATION NO. : 18/316999
DATED : January 14, 2025
INVENTOR(S) : Baiyong Li et al.

Page 1 of 2

It is certified that error appears in the above-identified patent and that said Letters Patent is hereby corrected as shown below:

On the Title Page

<u>Item (63) Related U.S. Application Data:</u>
"(63) Continuation of application No. 17/272,121, filed as Application No. PCT/CN2019/103618 on Aug. 30, 2019"
Should read:
--(63) Continuation of application No. 17/272,121, filed on Feb. 26, 2021, which is a 371 of Application No. PCT/CN2019/103618, filed on Aug. 30, 2019.--.

<u>Item (56) References Cited/Other Publications:</u>
"Chothia et al., "Canonical Structures for the Hpervariable Regions of Immunoglobulins," *Journal of Molecular Biology* 196:901-917, Aug. 1987. (18 pages)"
Should read:
--Chothia et al., "Canonical Structures for the Hypervariable Regions of Immunoglobulins," *Journal of Molecular Biology* 196:901-917, Aug. 1987. (18 pages)--.

"Fitzgerald et al., "Rational engineering of antibody therapeutics targeting multipleoncogene pathways," *mAbs* 3(3):299-309; May/Jun. 2011. (11 pages)"
Should read:
--Fitzgerald et al., "Rational engineering of antibody therapeutics targeting multiple oncogene pathways," *mAbs* 3(3):299-309; May/Jun. 2011. (11 pages)--.

In the Specification

<u>Column 11, Lines 56-57:</u>
Delete "The amino acid sequences of the 3 CDR regions of its light chain variable region are as follows:".

Signed and Sealed this
Twenty-seventh Day of May, 2025

Coke Morgan Stewart
*Acting Director of the United States Patent and Trademark Office*

CERTIFICATE OF CORRECTION (continued)
U.S. Pat. No. 12,195,527 B2

Column 12, Line 5:
Insert --The amino acid sequences of the 3 CDR regions of its light chain variable region are as follows:--.

Column 13, Line 59:
Cancel the text beginning with "As used herein, when referring" to and ending with "(766 amino acids)." in Column 14, ending on Line 13.

Column 23, After (SEQ. ID NO: 4):
Midway on the page, the following line of the nucleotide sequence is incorrect:
"ATGCAGAGCAAGGTGCTGCTGGCCGTCGCCTTGTGGCTCTGCGTGGAGACCCGGGC"
Should read:
--ATGCAGAGCAAGGTGCTGCTGGCCGTCGCCCTGTGGCTCTGCGTGGAGACCCGGGC--.

Column 29, Line 29:
"Preparation Example 5; Preparation"
Should read:
--Preparation Example 5: Preparation--.

Column 31, Line 37:
"GGGGSGGGGGGGGSGGGGS (SEQ ID NO: 13)"
Should read:
--GGGGSGGGGSGGGGSGGGGS (SEQ ID NO: 13)--.

Column 39, Line 47:
"Example 5; Competitive"
Should read:
--Example 5: Competitive--.

Column 42, Line 45:
"200 L/well,"
Should read:
--200 μL/well,--.

In the Claims

Column 58, Claim 21, Line 47:
"C-terminus of the other of"
Should read:
--C-terminus of one of--.

Column 58, Claim 21, Line 55:
"C-terminus of one of"
Should read:
--C-terminus of the other of--.